US011898196B2

(12) United States Patent
Marziali et al.

(10) Patent No.: US 11,898,196 B2
(45) Date of Patent: *Feb. 13, 2024

(54) METHOD FOR ISOLATING TARGET NUCLEIC ACID USING HETERODUPLEX BINDING PROTEINS

(71) Applicant: Quantum-Si Incorporated, Guilford, CT (US)

(72) Inventors: Andrea Marziali, North Vancouver (CA); Milenko Despotovic, Richmond (CA); Matthew Wiggin, Vancouver (CA); Joel Pel, Vancouver (CA)

(73) Assignee: Quantum-Si Incorporated, Branford, CT (US)

(*) Notice: Subject to any disclaimer, the term of this patent is extended or adjusted under 35 U.S.C. 154(b) by 74 days.

This patent is subject to a terminal disclaimer.

(21) Appl. No.: 17/405,083

(22) Filed: Aug. 18, 2021

(65) Prior Publication Data
US 2022/0056506 A1 Feb. 24, 2022

Related U.S. Application Data

(63) Continuation of application No. 15/575,699, filed as application No. PCT/IB2016/000796 on May 19, 2016, now Pat. No. 11,130,986.

(60) Provisional application No. 62/291,222, filed on Feb. 4, 2016, provisional application No. 62/164,247, filed on May 20, 2015.

(51) Int. Cl.
| | | |
|---|---|---|
| C12Q 1/68 | (2018.01) | |
| C12Q 1/6811 | (2018.01) | |
| C12Q 1/6806 | (2018.01) | |
| C12Q 1/6869 | (2018.01) | |
| C12Q 1/686 | (2018.01) | |
| C12Q 1/6874 | (2018.01) | |

(52) U.S. Cl.
CPC .......... *C12Q 1/6811* (2013.01); *C12Q 1/6806* (2013.01); *C12Q 1/686* (2013.01); *C12Q 1/6869* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 4,148,703 A | 4/1979 | Trop et al. | |
| 4,390,403 A | 6/1983 | Batchelder | |
| 4,390,404 A | 6/1983 | Esho et al. | |
| 4,732,656 A | 3/1988 | Hurd | |
| 4,830,726 A | 5/1989 | Stamato et al. | |
| 4,911,817 A | 3/1990 | Kindlmann | |
| 4,971,671 A | 11/1990 | Slater et al. | |
| 5,084,157 A | 1/1992 | Clark et al. | |
| 5,185,071 A | 2/1993 | Serwer | |
| 5,286,434 A | 2/1994 | Slater | |
| 5,302,510 A | 4/1994 | Klevan | |
| 5,384,022 A | 1/1995 | Rajasekaran | |
| 5,453,162 A | 9/1995 | Sabanayagam et al. | |
| 5,609,743 A | 3/1997 | Sasagawa | |
| 5,641,628 A | 6/1997 | Bianchi | |
| 5,707,804 A | 1/1998 | Mathies et al. | |
| 5,851,840 A | 12/1998 | Sluka et al. | |
| 5,938,904 A | 8/1999 | Bader | |
| 6,033,861 A * | 3/2000 | Schafer | C12Q 1/6827 536/25.4 |
| 6,036,831 A | 3/2000 | Bishop | |
| 6,110,670 A | 8/2000 | Van Broeckhoven et al. | |
| 6,120,992 A * | 9/2000 | Wagner, Jr. | C12Q 1/6827 435/6.15 |
| 6,146,511 A | 11/2000 | Slater | |
| 6,153,442 A | 11/2000 | Pirio et al. | |
| 6,193,866 B1 | 2/2001 | Bader | |
| 6,235,480 B1 | 5/2001 | Shultz et al. | |
| 6,248,518 B1 | 6/2001 | Parkhurst et al. | |
| 6,255,083 B1 | 7/2001 | Williams | |
| 6,258,540 B1 | 7/2001 | Lo et al. | |
| 6,277,489 B1 | 8/2001 | Abbott et al. | |
| 6,333,153 B1 | 12/2001 | Fishel et al. | |

(Continued)

FOREIGN PATENT DOCUMENTS

| | | | |
|---|---|---|---|
| CA | 2552262 A1 | 8/2005 | |
| CA | 2523089 A1 | 4/2006 | |

(Continued)

OTHER PUBLICATIONS

Ansorge (New Biotechnology, vol. 25, No. 5, Apr. 2009, pp. 195-203) (Year: 2009).*
Extended European Search Report dated May 2, 2012 in connection with Application No. EP 11004417.9.
International Preliminary Report on Patentability dated Aug. 7, 2006 in connection with Application No. PCT/CA2005/000124.
International Preliminary Report on Patentability dated Aug. 7, 2007 in connection with Application No. PCT/CA2006/000172.
International Preliminary Report on Patentability dated Aug. 12, 2010 in connection with Application No. PCT/CA2009/000111.
International Search Report and Written Opinion dated Feb. 23, 2010 in connection with Application No. PCT/CA2009/001648.
International Search Report and Written Opinion dated Jun. 2, 2006 in connection with Application No. PCT/CA2006/000172.

(Continued)

Primary Examiner — Juliet C Switzer
(74) Attorney, Agent, or Firm — Wolf, Greenfield & Sacks, P.C.

(57) ABSTRACT

The invention includes methods and apparatus for separating mutations, especially rare and unknown mutations, using heteroduplex binding proteins. Nucleic acids may optionally be nicked at or near the mutation in order to promote heteroduplex binding protein recognition and binding. In particular, using the disclosed methods, it is possible to separate heteroduplexed nucleic acid strand pair from homoduplexed nucleic acid strand pairs having similar sequences and being at a much higher concentration. Once the heteroduplexed nucleic acids are isolated and recovered, it is straightforward to analyze the sequences of the heteroduplexed nucleic acids, e.g., using sequencing or hybrid assays.

16 Claims, 35 Drawing Sheets

Specification includes a Sequence Listing.

(56) References Cited

U.S. PATENT DOCUMENTS

| | | |
|---|---|---|
| 6,340,566 B1 | 1/2002 | McCutchen-Maloney |
| 6,403,367 B1 | 6/2002 | Cheng et al. |
| 6,693,620 B1 | 2/2004 | Herb |
| 6,762,048 B2 | 7/2004 | Williams |
| 6,787,308 B2 | 9/2004 | Balasubramanian et al. |
| 6,824,664 B1 | 11/2004 | Austin |
| 6,827,830 B1 | 12/2004 | Slater |
| 6,846,638 B2 | 1/2005 | Shipwash |
| 6,869,764 B2 | 3/2005 | Williams et al. |
| 6,881,317 B2 | 4/2005 | Huang et al. |
| 6,893,546 B2 | 5/2005 | Jullien |
| 6,927,028 B2 | 8/2005 | Dennis et al. |
| 6,936,702 B2 | 8/2005 | Williams et al. |
| 7,052,847 B2 | 5/2006 | Korlach et al. |
| 7,056,661 B2 | 6/2006 | Korlach et al. |
| 7,175,747 B2 | 2/2007 | Bayerl et al. |
| 7,198,702 B1 | 4/2007 | Washizu |
| 7,229,799 B2 | 6/2007 | Williams |
| 7,361,466 B2 | 4/2008 | Korlach et al. |
| 7,371,533 B2 | 5/2008 | Slater |
| 7,427,343 B2 | 9/2008 | Han |
| 7,442,506 B2 | 10/2008 | Dhallan |
| 7,452,668 B2 | 11/2008 | Boles et al. |
| 7,838,647 B2 | 11/2010 | Hahn et al. |
| 7,888,017 B2 | 2/2011 | Quake et al. |
| 7,935,484 B2 | 5/2011 | Gocke et al. |
| 7,960,159 B2 | 6/2011 | Barany et al. |
| 7,968,702 B2 | 6/2011 | Wegener et al. |
| 8,008,018 B2 | 8/2011 | Quake et al. |
| 8,034,623 B2 | 10/2011 | Oh et al. |
| 8,084,734 B2 | 12/2011 | Vertes et al. |
| 8,133,371 B2 | 3/2012 | Marziali et al. |
| 8,153,375 B2 | 4/2012 | Travers et al. |
| 8,182,666 B2 | 5/2012 | Marziali et al. |
| 8,192,961 B2 | 6/2012 | Williams |
| 8,195,415 B2 | 6/2012 | Fan et al. |
| 8,252,910 B2 | 8/2012 | Korlach et al. |
| 8,257,954 B2 | 9/2012 | Clark et al. |
| 8,309,330 B2 | 11/2012 | Travers et al. |
| 8,354,252 B2 | 1/2013 | Wegener et al. |
| 8,420,366 B2 | 4/2013 | Clark et al. |
| 8,455,193 B2 | 6/2013 | Travers et al. |
| 8,480,871 B2 | 7/2013 | Marziali et al. |
| 8,518,228 B2 | 8/2013 | Marziali et al. |
| 8,529,744 B2 | 9/2013 | Marziali et al. |
| 8,530,154 B2 | 9/2013 | Williams |
| 8,581,179 B2 | 11/2013 | Franzen |
| 8,846,881 B2 | 9/2014 | Korlach et al. |
| 8,906,614 B2 | 12/2014 | Wegener et al. |
| 8,927,212 B2 | 1/2015 | Kong et al. |
| 8,980,584 B2 | 3/2015 | Williams |
| 9,011,661 B2 | 4/2015 | Marziali et al. |
| 9,062,091 B2 | 6/2015 | Bjornson et al. |
| 9,186,685 B2 | 11/2015 | Marziali et al. |
| 9,404,146 B2 | 8/2016 | Travers et al. |
| 9,434,938 B2 | 9/2016 | Marziali et al. |
| 9,435,810 B2 | 9/2016 | Havranek et al. |
| 9,464,107 B2 | 10/2016 | Wegener et al. |
| 9,542,527 B2 | 1/2017 | Travers et al. |
| 9,551,031 B2 | 1/2017 | Korlach et al. |
| 9,551,660 B2 | 1/2017 | Kong et al. |
| 9,555,354 B2 | 1/2017 | Marziali et al. |
| 9,566,335 B1 | 2/2017 | Emili et al. |
| 9,582,640 B2 | 2/2017 | Travers et al. |
| 9,600,626 B2 | 3/2017 | Travers et al. |
| 9,678,080 B2 | 6/2017 | Bjornson et al. |
| 9,719,073 B2 | 8/2017 | Emig et al. |
| 9,845,501 B2 | 12/2017 | Williams |
| 9,879,319 B2 | 1/2018 | Korlach et al. |
| 9,910,956 B2 | 3/2018 | Travers et al. |
| 9,957,291 B2 | 5/2018 | Sebo et al. |
| 10,023,605 B2 | 7/2018 | Bjornson et al. |
| 10,066,258 B2 | 9/2018 | Kong et al. |
| 10,150,872 B2 | 12/2018 | Zheng et al. |
| 10,161,002 B2 | 12/2018 | Korlach et al. |
| 10,337,054 B2 | 7/2019 | Marziali et al. |
| 10,400,266 B2 | 9/2019 | Marziali et al. |
| 10,481,162 B2 | 11/2019 | Emili et al. |
| 10,544,449 B2 | 1/2020 | Shen et al. |
| 10,545,153 B2 | 1/2020 | Marcotte et al. |
| 10,570,445 B2 | 2/2020 | Kong et al. |
| 10,676,788 B2 | 6/2020 | Shen et al. |
| 10,738,351 B2 | 8/2020 | Marziali et al. |
| 10,745,750 B2 | 8/2020 | Korlach et al. |
| 10,787,573 B2 | 9/2020 | Zheng et al. |
| 10,829,800 B2 | 11/2020 | Marziali et al. |
| 10,975,421 B2 | 4/2021 | Marziali et al. |
| 11,130,986 B2 * | 9/2021 | Marziali ............ C12Q 1/686 |
| 2001/0045359 A1 | 11/2001 | Cheng |
| 2002/0036139 A1 | 3/2002 | Becker |
| 2002/0081280 A1 | 6/2002 | Becker |
| 2002/0119448 A1 | 8/2002 | Sorge |
| 2002/0179445 A1 | 12/2002 | Alajoki |
| 2003/0027178 A1 | 2/2003 | Vasmatzis |
| 2003/0215855 A1 | 11/2003 | Dubrow et al. |
| 2005/0042633 A1 | 2/2005 | Williams |
| 2005/0164241 A1 | 7/2005 | Hahn et al. |
| 2005/0164402 A1 | 7/2005 | Belisle |
| 2005/0247563 A1 | 11/2005 | Shuber |
| 2005/0247564 A1 | 11/2005 | Volkel |
| 2005/0266456 A1 | 12/2005 | Williams et al. |
| 2007/0072196 A1 | 3/2007 | Xu et al. |
| 2007/0215472 A1 | 9/2007 | Slater |
| 2007/0218494 A1 | 9/2007 | Slater |
| 2007/0219367 A1 | 9/2007 | Shchepinov et al. |
| 2008/0108063 A1 | 5/2008 | Lucero et al. |
| 2008/0314751 A1 | 12/2008 | Bukshpan et al. |
| 2009/0120795 A1 | 5/2009 | Marziali |
| 2009/0139867 A1 | 6/2009 | Marziali |
| 2009/0152116 A1 | 6/2009 | Boles et al. |
| 2009/0263802 A1 | 10/2009 | Drmanac |
| 2010/0009872 A1 | 1/2010 | Eid et al. |
| 2010/0029494 A1 | 2/2010 | Cherkasov et al. |
| 2010/0035254 A1 | 2/2010 | Williams |
| 2010/0233701 A1 | 9/2010 | Heng et al. |
| 2010/0273219 A1 | 10/2010 | May et al. |
| 2010/0285537 A1 | 11/2010 | Zimmermann |
| 2011/0003343 A1 | 1/2011 | Nikiforov et al. |
| 2011/0048950 A1 | 3/2011 | Marziali |
| 2011/0152111 A1 | 6/2011 | Fan et al. |
| 2011/0245482 A1 | 10/2011 | Hahn et al. |
| 2011/0272282 A1 | 11/2011 | Marziali |
| 2011/0281776 A1 | 11/2011 | Eshoo et al. |
| 2012/0035062 A1 | 2/2012 | Schultz et al. |
| 2012/0048735 A1 | 3/2012 | Marziali et al. |
| 2012/0160682 A1 | 6/2012 | Marziali et al. |
| 2012/0199481 A1 | 8/2012 | Marziali et al. |
| 2012/0295265 A1 * | 11/2012 | Marziali ............ B03C 7/023 435/6.12 |
| 2012/0322692 A1 | 12/2012 | Pham et al. |
| 2012/0329064 A1 * | 12/2012 | Marziali ............ B03C 5/026 435/6.12 |
| 2013/0224740 A1 | 8/2013 | Thierry et al. |
| 2013/0316912 A1 | 11/2013 | Bjornson et al. |
| 2013/0323742 A1 | 12/2013 | Marziali et al. |
| 2016/0289744 A1 | 10/2016 | Marziali et al. |
| 2017/0073742 A1 | 3/2017 | Marziali et al. |
| 2017/0136433 A1 | 5/2017 | Sun et al. |
| 2018/0211003 A1 | 7/2018 | Travers et al. |
| 2018/0299460 A1 | 10/2018 | Emili |
| 2018/0346507 A1 | 12/2018 | Sebo et al. |
| 2019/0010183 A1 | 1/2019 | Bjornson et al. |
| 2019/0185916 A1 | 6/2019 | Marziali et al. |
| 2019/0210641 A1 | 7/2019 | Marziali et al. |
| 2019/0249153 A1 | 8/2019 | Kamtekar et al. |
| 2019/0249234 A1 | 8/2019 | Marziali et al. |
| 2019/0338342 A1 | 11/2019 | Marziali et al. |
| 2020/0141944 A1 | 5/2020 | Emili et al. |
| 2020/0148727 A1 | 5/2020 | Tullman et al. |
| 2021/0121879 A1 | 4/2021 | Rothberg et al. |

(56) References Cited

U.S. PATENT DOCUMENTS

| | | |
|---|---|---|
| 2021/0164035 A1 | 6/2021 | Rothberg et al. |
| 2021/0238663 A1 | 8/2021 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| CA | 3 056 256 A1 | 10/2018 |
| EP | 356187 A2 | 2/1990 |
| EP | 1720636 A1 | 11/2006 |
| EP | 1859249 A1 | 11/2007 |
| EP | 2238434 A1 | 10/2010 |
| EP | 2458004 A1 | 5/2012 |
| GB | 2249395 A | 5/1992 |
| JP | 7-167837 | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 S | 3/2003 |
| JP | 2003-513240 S | 4/2003 |
| JP | 2003-215099 A | 7/2003 |
| JP | 2003-247980 A | 9/2003 |
| WO | WO 95/14923 A1 | 6/1995 |
| WO | WO 97/27933 A1 | 8/1997 |
| WO | WO 99/38874 A2 | 8/1999 |
| WO | WO 99/45374 A2 | 9/1999 |
| WO | WO 2001/31325 A1 | 5/2001 |
| WO | WO 2002/0242500 A2 | 5/2002 |
| WO | WO 2003/0019172 A2 | 3/2003 |
| WO | WO 2004/009622 A2 | 1/2004 |
| WO | WO 2005/044836 A2 | 5/2005 |
| WO | WO 2005/072854 A1 | 8/2005 |
| WO | WO 2006/063625 A1 | 6/2006 |
| WO | WO 2006/081691 A1 | 8/2006 |
| WO | WO 2007/070572 A2 | 6/2007 |
| WO | WO 2007/092473 A2 | 8/2007 |
| WO | WO 2009/094772 A1 | 8/2009 |
| WO | WO 2010/051649 A1 | 5/2010 |
| WO | WO 2010/065322 A1 | 6/2010 |
| WO | WO 2010/104798 A1 | 9/2010 |
| WO | WO 2010/115016 A2 | 10/2010 |
| WO | WO 2010/121381 A1 | 10/2010 |
| WO | WO 2013/002616 A2 | 10/2013 |
| WO | WO 2019/040825 A1 | 2/2019 |

OTHER PUBLICATIONS

Extended European Search Report dated May 19, 2011 in connection with Application No. EP 09706657.5.
Supplementary European Search Report for Application No. EP 05706448.7 dated May 22, 2012.
International Search Report and Written Opinion for Application No. PCT/CA2012/05057 dated Feb. 28, 2013.
International Search Report and Written Opinion for Application No. PCT/US2013/039553 dated Sep. 18, 2013.
International Search Report and Written Opinion for Application No. PCT/CA2005/000124 dated Jun. 2, 2005.
International Search Report and Written Opinion for Application No. PCT/IB2016/000796 dated Aug. 31, 2016.
International Search Report and Written Opinion for Application No. PCT/CA2009/00011 dated May 14, 2009.
Andersen et al., 2008, Combining a symptoms index with CA 125 to improve detection of ovarian cancer, Cancer,113(3):484-489.
Asbury et al., Trapping of DNA by dielectrophoresis, Electrophoresis, 2002, 23:2658-2666.
Asbury et al., Trapping of DNA in Nonuniform Oscillating Electric Fields, Biophysical Journal, 1998, 74:1024-1030.
Astumian et al., Fluctuation Driven Ratchets: Molecular Motors, Physical Review Letters, 1994, 72(11):1766-1769.
Baba et al., Capillary Affinity Gel Electrophoresis, Molecular Biotechnology, 1996, (9):1-11.
Bier et al., Biasing brownian motion in different directions in a 3-state fluctuating potential and an application for the separation of small particles, Physical Review Letters, 1996, 76(22):4277-4280.
Broemeling et al., An instrument for automated purification of nucleic acids from contaminated forensic samples, JALA, 2008,13:40-48.
Carle et al., Electrophoretic separation of large DNA molecules by periodic inversion of the electric field, Science, 1986, 232(4746):65-68.
Chacron et al., Particle trapping and self-focusing in temporarily asymmetric ratchets with strong field gradients, Physical Review E, 1997, 56(3):3446-3450.
Chakrabarti et al., Highly Selective Isolation of Unknown Mutations in Diverse DNA Fragments: Toward New Multiplex Screening in Cancer, American Association for Cancer Reserch, 2000, 60:3732-3737.
Chan et al., Size Distributions of Maternal and Fetal DNA in Maternal Plasma, Molecular Diagnostics and Genetics, Clinical Chemistry, 2004, 50(1):88-92.
Chu, Bag model for DNA migration during pulsed-field electrophoresis, Proc. Natl. Acad. Sci., 1991, 88:11071-11075.
Forshew et al., 2012, Noninvasive Identification and Monitoring of Cancer Mutations by Targeted Deep Sequencing of Plasma DNA, (Science Translational Medicine, 3(136) 136ra68, pp. 1-12 and supplemental material, pp. 1-19.
Frank, Somatic mosaicism and disease. Curr Biol. Jun. 16, 2014;24(12):R577-R581. doi: 10.1016/j.cub.2014.05.021.
Frumin et al., Anomalous size dependence of the non linear mobility of DNA, Phys Chem Commun, 2000, 11(3):61-63.
Frumin et al., Nonlinear focusing of DNA macromolecules, Physical Review E—Statistical, Nonlinear and Soft Matter Physics, 2001, 64(2 Part 1):021902-1-5.
Griess et al., Cyclic capillary electrophoresis, Electrophoresis, 2002, 23:2610-2617.
Jorgez et al., Quantity versus quality: Optimal methods for cell-free DNA isolation from plasma of pregnant women, American College of Medical Genetics, 2006, 8(10):615-619.
Kennedy et al., 2011, Somatic Mutations in Aging, Cancer and Neurodegeneration, Mech. Ageing Dev., doi:10.1016/j.mad.2011.10.009.
Kitzman et al., Noninvasive Whole-Genome Sequencing of a Human Fetus, Sci Transl Med 4, 137ra76 (2012); DOI: 10.1126/scitranslmed. 3004323, 9 pages.
Kopecka et al., Capillary electrophoresis sequencing of small ssDNA molecules versus the Ogston regime: fitting data and interpreting parameters, Electrophoresis, 2004, 25(14):2177-2185.
Koushik et al., Cerulean, Venus, and Venus Y67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Lalande et al., Pulsed-field electrophoresis: Application of a computer model to the separation of large DNA molecules, Proc. Natl. Acad. Sci. USA, 1987, 84:8011-8015.
Lun et al., Microfluidics Digital PCR Reveals a Higher than Expected Fraction of Fetal DNA in Maternal Plasma, Molecular Diagnostics and Genetics, Clinical Chemistry, 2008, 54(10):1664-1672.
Magnasco, Forced thermal ratchets, Physical Review Letters, 1993, 71(10):1477-1481.
Makridakis, PCR-free method detects high frequency of genomic instability in prostate cancer, Nucleic Acids Research, 2009, 37(22):7441-7446.
Marziali et al., Novel electrophoresis mechanism based on synchronous alternating drag perturbation, Electrophoresis, 2005, 26:82-90.
Nollau et al., Methods for detection of point mutations: performance and quality assessment, Department of Clinical Chemistry, 1997, 43(7):1114-1128.
Parsons et al., Evaluation of MutS as a tool for direct measurement of point mutations in genomic DNA. Mutat Res. Mar. 21, 1997;374(2):277-85. doi: 10.1016/s0027-5107(96)00245-x.

(56) References Cited

OTHER PUBLICATIONS

Pel et al,. Nonlinear electrophoretic response yields a unique parameter for separation of biomolecules, PNAS, 2009, 106(35):14796-14801.

Pel, A novel electrophoretic mechanism and separation parameter for selective nucleic acid concentration based on synchronous coefficient of drag alteration (SCODA), (Ph.D. Thesis published in 2009), Vancouver: University of British Columbia,2009.

Rousseau et al., Gel electrophoretic mobility of single-stranded DNA: The two reptation field-dependent factors, Electrophoresis, 2000, 21(8):1464-1470.

Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.

Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.

Sikora et al., Detection of Increased Amounts of Cell-Free DNA with Short PCR Amplicons, Clinical Chemistry, 2010, 56(1):136-138.

Slater et al., Recent developments in DNA electrophoretic separations, Electrophoresis, 1998, 19(10):1525-1541.

Slater et al., The theory of DNA separation by capillary electrophoresis, Current Opinion in Biotechnology, 2003, 14:58-64.

Slater et al., Theory of DNA electrophoresis: a look at some current challenges, Electrophoresis, 2000, 21:3873-3887.

So et al. ,Efficient genomic DNA extraction from low target concentration bacterial cultures using SCODA DNA extraction technology, Cold Spring Harb Protoc, 2010, 1150-1153.

Stanislawska-Sachadyn, MutS as a tool for mutation detection. Acta Biochim Pol. 2005;52(3):575-83. Epub Aug. 4, 2005.

Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

Tessier et al., Strategies for the separation of polyelectrolytes based on non-linear dynamics and entropic ratchets mple microfluidic device, Applied Physics A—Materials Science & Processing, 2002, 75:285-291.

Thompson et al., Winnowing DNA for Rare Sequences: Highly Specific Sequence and Methylation Based Enrichment, PLOS One, vol. 7, No. 2, Feb. 15, 2012.

Turmel et al., Molecular detrapping and band narrowing with high frequency modulation of pulsed field electrophoresis, Nucleic Acids Research, 1990, 18(3):569-575.

Viovy, Electrophoresis of DNA and other polyelectrolytes: Physical mechanisms, Review of Modern Physics, 2000, 72(3):813-872.

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

Wright, Cell-free fetal nucleic acids for non-invasive prenatal diagnosis, Report of the UK export working group, Jan. 2009, 64 pages.

Yobas et al., Nucleic Acid Extraction, Amplification, and Detection on Si-Based Microfluidic Platforms, IEEE Journal of Solid-State Circuits, vol. 42, No. 8, Aug. 2007, 12 pages.

Zhong et al., MutS-Mediated Enrichment of Mutated DNA Produced by Directed Evolution in Vitro. World J Microbiol Biotechnol, 2011;27:1367-72.

Office Action dated Dec. 27, 2010 for U.S. Appl. No. 11/815,760.
Office Action dated Aug. 19, 2011 for U.S. Appl. No. 11/815,760.
Elder et al., Automatic reading of DNA sequencing gel autoradiographs using a large format digital scanner. Nucleic Acids Res. Jan. 10, 1986;14(1):417-24. doi: 10.1093/nar/14.1.417.

Kelly, Southern blotting. Proc Nutr Soc. Mar. 1996;55(1B):591-7. doi: 10.1079/pns19960052.

U.S. Appl. No. 17/227,121, filed Apr. 9, 2021, Marziali et al.

\* cited by examiner

Heteroduplex Recovery

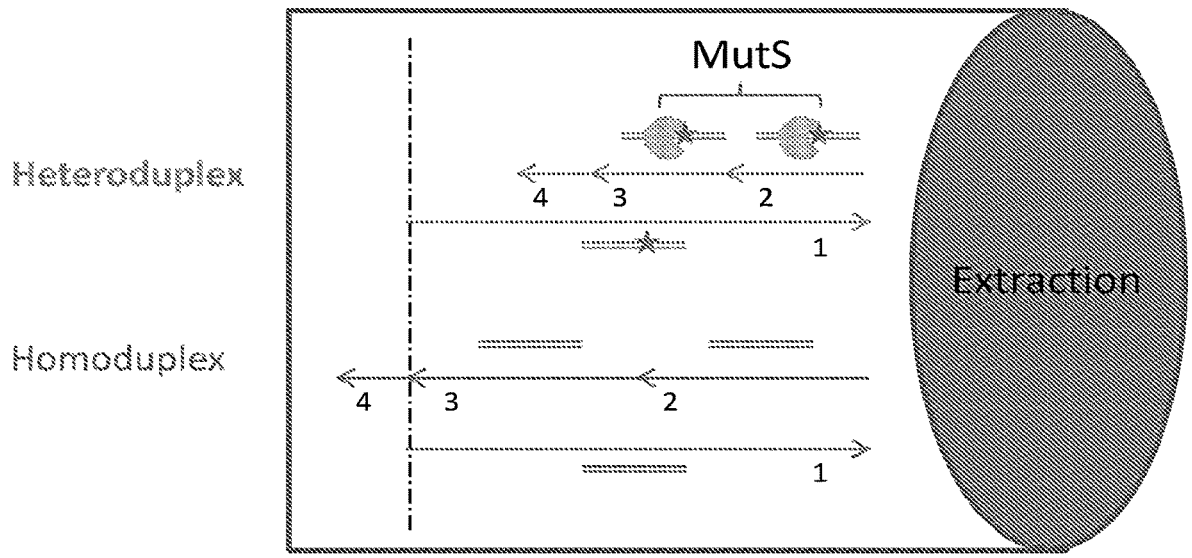

- Steps 1-3 integrate to zero net electric field (SCODA)
- Step 1, high field, high temperature
- Steps 2-3, low field, low temperature
- Step 4 is a wash field which pushes homoduplex and heteroduplex molecules backwards
- MutS binds preferentially to heteroduplex molecules at low temperature (in low field steps), reducing DNA mobility
- Heteroduplex has a net forward motion, and over many cycles will migrate towards an extraction chamber

FIGURE 10

SEQUENCE LISTING

<160> NUMBER OF SEQ ID NOS: 3

<210> SEQ ID NO 1
<211> LENGTH: 853
<212> TYPE: PRT
<213> ORGANISM: Escherichia coli

<400> SEQUENCE: 1

Met Ser Thr Pro Glu Asn Phe Asp Ala His Thr Pro Met Met Gln Gln
1               5                   10                  15

Tyr Leu Lys Leu Lys Ala Gln His Pro Glu Ile Leu Leu Phe Tyr Arg
                20                  25                  30

Met Gly Asp Phe Tyr Glu Leu Phe Tyr Asp Asp Ala Lys Arg Ala Ser
            35                  40                  45

Gln Leu Leu Asp Ile Ser Leu Thr Lys Arg Gly Ala Ser Ala Gly Glu
        50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

```
Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125

Gln Asp Asn Leu Leu Ala Ala Ile Trp Gln Asp Ser Lys Gly Phe Gly
    130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
                165                 170                 175

Glu Leu Leu Tyr Ala Glu Asp Phe Ala Glu Met Ser Leu Ile Glu Gly
            180                 185                 190

Arg Arg Gly Leu Arg Arg Pro Leu Trp Glu Phe Glu Ile Asp Thr
        195                 200                 205

Ala Arg Gln Gln Leu Asn Leu Gln Phe Gly Thr Arg Asp Leu Val Gly
    210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
                245                 250                 255

Ser Ile Thr Met Glu Arg Gln Gln Asp Ser Ile Ile Met Asp Ala Ala
            260                 265                 270

Thr Arg Arg Asn Leu Glu Ile Thr Gln Asn Leu Ala Gly Gly Ala Glu
        275                 280                 285

Asn Thr Leu Ala Ser Val Leu Asp Cys Thr Val Thr Pro Met Gly Ser
    290                 295                 300

Arg Met Leu Lys Arg Trp Leu His Met Pro Val Arg Asp Thr Arg Val
305                 310                 315                 320

Leu Leu Glu Arg Gln Gln Thr Ile Gly Ala Leu Gln Asp Phe Thr Ala
                325                 330                 335

Glu Leu Gln Pro Val Leu Arg Gln Val Gly Asp Leu Glu Arg Ile Leu
            340                 345                 350

Ala Arg Leu Ala Leu Arg Thr Ala Arg Pro Arg Asp Leu Ala Arg Met
        355                 360                 365

Arg His Ala Phe Gln Gln Leu Pro Glu Leu Arg Ala Gln Leu Glu Asn
    370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
                405                 410                 415

Val Leu Val Arg Asp Gly Gly Val Ile Ala Ser Gly Tyr Asn Glu Glu
            420                 425                 430

Leu Asp Glu Trp Arg Ala Leu Ala Asp Gly Ala Thr Asp Tyr Leu Glu
        435                 440                 445

Arg Leu Glu Val Arg Glu Arg Glu Arg Thr Gly Leu Asp Thr Leu Lys
    450                 455                 460

Val Gly Phe Asn Ala Val His Gly Tyr Tyr Ile Gln Ile Ser Arg Gly
465                 470                 475                 480

Gln Ser His Leu Ala Pro Ile Asn Tyr Met Arg Arg Gln Thr Leu Lys
                485                 490                 495

Asn Ala Glu Arg Tyr Ile Ile Pro Glu Leu Lys Glu Tyr Glu Asp Lys
            500                 505                 510
```

```
Val Leu Thr Ser Lys Gly Lys Ala Leu Ala Leu Glu Lys Gln Leu Tyr
            515                 520                 525

Glu Glu Leu Phe Asp Leu Leu Leu Pro His Leu Glu Ala Leu Gln Gln
530                 535                 540

Ser Ala Ser Ala Leu Ala Glu Leu Asp Val Leu Val Asn Leu Ala Glu
545                 550                 555                 560

Arg Ala Tyr Thr Leu Asn Tyr Thr Cys Pro Thr Phe Ile Asp Lys Pro
                565                 570                 575

Gly Ile Arg Ile Thr Glu Gly Arg His Pro Val Val Glu Gln Val Leu
                580                 585                 590

Asn Glu Pro Phe Ile Ala Asn Pro Leu Asn Leu Ser Pro Gln Arg Arg
            595                 600                 605

Met Leu Ile Ile Thr Gly Pro Asn Met Gly Gly Lys Ser Thr Tyr Met
610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
                660                 665                 670

Glu Met Thr Glu Thr Ala Asn Ile Leu His Asn Ala Thr Glu Tyr Ser
            675                 680                 685

Leu Val Leu Met Asp Glu Ile Gly Arg Gly Thr Ser Thr Tyr Asp Gly
690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                725                 730                 735

Glu Lys Met Glu Gly Val Ala Asn Val His Leu Asp Ala Leu Glu His
                740                 745                 750

Gly Asp Thr Ile Ala Phe Met His Ser Val Gln Asp Gly Ala Ala Ser
            755                 760                 765

Lys Ser Tyr Gly Leu Ala Val Ala Ala Leu Ala Gly Val Pro Lys Glu
770                 775                 780

Val Ile Lys Arg Ala Arg Gln Lys Leu Arg Glu Leu Glu Ser Ile Ser
785                 790                 795                 800

Pro Asn Ala Ala Ala Thr Gln Val Asp Gly Thr Gln Met Ser Leu Leu
                805                 810                 815

Ser Val Pro Glu Glu Thr Ser Pro Ala Val Glu Ala Leu Glu Asn Leu
                820                 825                 830

Asp Pro Asp Ser Leu Thr Pro Arg Gln Ala Leu Glu Trp Ile Tyr Arg
            835                 840                 845

Leu Lys Ser Leu Val
850

<210> SEQ ID NO 2
<211> LENGTH: 1360
<212> TYPE: PRT
<213> ORGANISM: Homo sapiens

<400> SEQUENCE: 2

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
                20                  25                  30
```

```
Arg Ala Ala Ala Ala Pro Glu Ala Ser Pro Ser Pro Gly Gly Asp Ala
        35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                    85                  90                  95

Trp Ala Lys Met Glu Gly Tyr Pro Trp Trp Pro Cys Leu Val Tyr Asn
                100                 105                 110

His Pro Phe Asp Gly Thr Phe Ile Arg Glu Lys Gly Lys Ser Val Arg
            115                 120                 125

Val His Val Gln Phe Phe Asp Asp Ser Pro Thr Arg Gly Trp Val Ser
        130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Glu Met
        195                 200                 205

Glu Val Gly Thr Thr Tyr Val Thr Asp Lys Ser Glu Glu Asp Asn Glu
    210                 215                 220

Ile Glu Ser Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
    290                 295                 300

Thr Gly Asn Gly Ser Leu Lys Arg Lys Ser Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
    370                 375                 380

Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
                405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445
```

```
Leu Val Phe Met Lys Gly Asn Trp Ala His Ser Gly Phe Pro Glu Ile
450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
                500                 505                 510

Ile Cys Arg Ile Ile Thr Lys Gly Thr Gln Thr Tyr Ser Val Leu Glu
                515                 520                 525

Gly Asp Pro Ser Glu Asn Tyr Ser Lys Tyr Leu Leu Ser Leu Lys Glu
530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
                580                 585                 590

Gln Val Leu Phe Glu Lys Gly Asn Leu Ser Lys Glu Thr Lys Thr Ile
                595                 600                 605

Leu Lys Ser Ser Leu Ser Cys Ser Leu Gln Glu Gly Leu Ile Pro Gly
610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
                660                 665                 670

Pro Gly Glu Lys Ser Glu Leu Ala Leu Ser Ala Leu Gly Gly Cys Val
                675                 680                 685

Phe Tyr Leu Lys Lys Cys Leu Ile Asp Gln Glu Leu Leu Ser Met Ala
690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
                740                 745                 750

Ser Thr Glu Gly Thr Leu Leu Glu Arg Val Asp Thr Cys His Thr Pro
                755                 760                 765

Phe Gly Lys Arg Leu Leu Lys Gln Trp Leu Cys Ala Pro Leu Cys Asn
770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                805                 810                 815

Asp Leu Glu Arg Leu Leu Ser Lys Ile His Asn Val Gly Ser Pro Leu
                820                 825                 830

Lys Ser Gln Asn His Pro Asp Ser Arg Ala Ile Met Tyr Glu Glu Thr
                835                 840                 845

Thr Tyr Ser Lys Lys Ile Ile Asp Phe Leu Ser Ala Leu Glu Gly
850                 855                 860

Phe Lys Val Met Cys Lys Ile Ile Gly Ile Met Glu Glu Val Ala Asp
```

```
865                 870                 875                 880
Gly Phe Lys Ser Lys Ile Leu Lys Gln Val Ile Ser Leu Gln Thr Lys
                885                 890                 895
Asn Pro Glu Gly Arg Phe Pro Asp Leu Thr Val Glu Leu Asn Arg Trp
            900                 905                 910
Asp Thr Ala Phe Asp His Glu Lys Ala Arg Lys Thr Gly Leu Ile Thr
            915                 920                 925
Pro Lys Ala Gly Phe Asp Ser Asp Tyr Asp Gln Ala Leu Ala Asp Ile
        930                 935                 940
Arg Glu Asn Glu Gln Ser Leu Leu Glu Tyr Leu Glu Lys Gln Arg Asn
945                 950                 955                 960
Arg Ile Gly Cys Arg Thr Ile Val Tyr Trp Gly Ile Gly Arg Asn Arg
                965                 970                 975
Tyr Gln Leu Glu Ile Pro Glu Asn Phe Thr Thr Arg Asn Leu Pro Glu
            980                 985                 990
Glu Tyr Glu Leu Lys Ser Thr Lys Lys Gly Cys Lys Arg Tyr Trp Thr
        995                 1000                1005
Lys Thr Ile Glu Lys Lys Leu Ala Asn Leu Ile Asn Ala Glu Glu
        1010                1015                1020
Arg Arg Asp Val Ser Leu Lys Asp Cys Met Arg Arg Leu Phe Tyr
        1025                1030                1035
Asn Phe Asp Lys Asn Tyr Lys Asp Trp Gln Ser Ala Val Glu Cys
        1040                1045                1050
Ile Ala Val Leu Asp Val Leu Leu Cys Leu Ala Asn Tyr Ser Arg
        1055                1060                1065
Gly Gly Asp Gly Pro Met Cys Arg Pro Val Ile Leu Leu Pro Glu
        1070                1075                1080
Asp Thr Pro Pro Phe Leu Glu Leu Lys Gly Ser Arg His Pro Cys
        1085                1090                1095
Ile Thr Lys Thr Phe Phe Gly Asp Asp Phe Ile Pro Asn Asp Ile
        1100                1105                1110
Leu Ile Gly Cys Glu Glu Glu Gln Glu Asn Gly Lys Ala Tyr
        1115                1120                1125
Cys Val Leu Val Thr Gly Pro Asn Met Gly Gly Lys Ser Thr Leu
        1130                1135                1140
Met Arg Gln Ala Gly Leu Leu Ala Val Met Ala Gln Met Gly Cys
        1145                1150                1155
Tyr Val Pro Ala Glu Val Cys Arg Leu Thr Pro Ile Asp Arg Val
        1160                1165                1170
Phe Thr Arg Leu Gly Ala Ser Asp Arg Ile Met Ser Gly Glu Ser
        1175                1180                1185
Thr Phe Phe Val Glu Leu Ser Glu Thr Ala Ser Ile Leu Met His
        1190                1195                1200
Ala Thr Ala His Ser Leu Val Leu Val Asp Glu Leu Gly Arg Gly
        1205                1210                1215
Thr Ala Thr Phe Asp Gly Thr Ala Ile Ala Asn Ala Val Val Lys
        1220                1225                1230
Glu Leu Ala Glu Thr Ile Lys Cys Arg Thr Leu Phe Ser Thr His
        1235                1240                1245
Tyr His Ser Leu Val Glu Asp Tyr Ser Gln Asn Val Ala Val Arg
        1250                1255                1260
Leu Gly His Met Ala Cys Met Val Glu Asn Glu Cys Glu Asp Pro
        1265                1270                1275
```

```
Ser Gln Glu Thr Ile Thr Phe Leu Tyr Lys Phe Ile Lys Gly Ala
    1280                1285                1290

Cys Pro Lys Ser Tyr Gly Phe Asn Ala Ala Arg Leu Ala Asn Leu
    1295                1300                1305

Pro Glu Glu Val Ile Gln Lys Gly His Arg Lys Ala Arg Glu Phe
    1310                1315                1320

Glu Lys Met Asn Gln Ser Leu Arg Leu Phe Arg Glu Val Cys Leu
    1325                1330                1335

Ala Ser Glu Arg Ser Thr Val Asp Ala Glu Ala Val His Lys Leu
    1340                1345                1350

Leu Thr Leu Ile Lys Glu Leu
    1355                1360

<210> SEQ ID NO 3
<211> LENGTH: 819
<212> TYPE: PRT
<213> ORGANISM: Thermus thermophilus

<400> SEQUENCE: 3

Met Gly Gly Tyr Gly Gly Val Lys Met Glu Gly Met Leu Lys Gly Glu
1               5                   10                  15

Gly Pro Gly Pro Leu Pro Pro Leu Leu Gln Gln Tyr Val Glu Leu Arg
                20                  25                  30

Asp Arg Tyr Pro Asp Tyr Leu Leu Leu Phe Gln Val Gly Asp Phe Tyr
                35                  40                  45

Glu Cys Phe Gly Glu Asp Ala Glu Arg Leu Ala Arg Ala Leu Gly Leu
    50                  55                  60

Val Leu Thr His Lys Thr Ser Lys Asp Phe Thr Thr Pro Met Ala Gly
65                  70                  75                  80

Ile Pro Ile Arg Ala Phe Asp Ala Tyr Ala Glu Arg Leu Leu Lys Met
                85                  90                  95

Gly Phe Arg Leu Ala Val Ala Asp Gln Val Glu Pro Ala Glu Glu Ala
                100                 105                 110

Glu Gly Leu Val Arg Arg Glu Val Thr Gln Leu Leu Thr Pro Gly Thr
                115                 120                 125

Leu Thr Gln Glu Ala Leu Leu Pro Arg Glu Ala Asn Tyr Leu Ala Ala
    130                 135                 140

Ile Ala Thr Gly Asp Gly Trp Gly Leu Ala Phe Leu Asp Val Ser Thr
145                 150                 155                 160

Gly Glu Phe Lys Gly Thr Leu Leu Lys Ser Lys Ser Ala Leu Tyr Asp
                165                 170                 175

Glu Leu Phe Arg His Arg Pro Ala Glu Val Leu Leu Ala Pro Glu Leu
                180                 185                 190

Arg Glu Asn Glu Ala Phe Val Ala Glu Phe Arg Lys Arg Phe Pro Val
                195                 200                 205

Met Leu Ser Glu Ala Pro Phe Gly Pro Gln Gly Glu Gly Pro Leu Ala
    210                 215                 220

Leu Arg Arg Ala Gln Gly Ala Leu Leu Ala Tyr Ala Arg Ala Thr Gln
225                 230                 235                 240

Gly Gly Ala Leu Ser Val Arg Pro Phe Arg Leu Tyr Asp Pro Gly Ala
                245                 250                 255

Phe Val Arg Leu Pro Glu Ala Ser Leu Lys Ala Leu Glu Val Phe Glu
                260                 265                 270

Pro Leu Arg Gly Gln Asp Thr Leu Phe Gly Val Leu Asp Glu Thr Arg
```

```
                275                 280                 285
Thr Ala Pro Gly Arg Arg Leu Leu Gln Ala Trp Leu Arg His Pro Leu
290                 295                 300
Leu Glu Arg Gly Pro Leu Glu Ala Arg Leu Asp Arg Val Glu Arg Phe
305                 310                 315                 320
Val Arg Glu Gly Ala Leu Arg Glu Gly Val Arg Arg Leu Leu Phe Arg
                325                 330                 335
Leu Ala Asp Leu Glu Arg Leu Ala Thr Arg Leu Glu Leu Ser Arg Ala
                340                 345                 350
Ser Pro Arg Asp Leu Ala Ala Leu Arg Arg Ser Leu Glu Ile Leu Pro
                355                 360                 365
Glu Leu Lys Gly Leu Leu Gly Glu Val Gly Leu Pro Asp Leu Ser
370                 375                 380
Gly Leu Leu Glu Glu Leu Arg Ala Ala Leu Val Glu Asp Pro Pro Leu
385                 390                 395                 400
Lys Val Ser Glu Gly Gly Leu Ile Arg Glu Gly Tyr Asp Pro Asp Leu
                405                 410                 415
Asp Ala Leu Arg Arg Ala His Ala Glu Gly Val Ala Tyr Phe Leu Asp
                420                 425                 430
Leu Glu Ala Arg Glu Lys Glu Arg Thr Gly Ile Pro Thr Leu Lys Val
                435                 440                 445
Gly Tyr Asn Ala Val Phe Gly Tyr Tyr Leu Glu Val Thr Arg Pro Tyr
450                 455                 460
Tyr Glu Lys Val Pro Gln Glu Tyr Arg Pro Val Gln Thr Leu Lys Asp
465                 470                 475                 480
Arg Gln Arg Tyr Thr Leu Pro Glu Met Lys Glu Arg Glu Arg Glu Leu
                485                 490                 495
Tyr Arg Leu Glu Ala Leu Ile Lys Arg Glu Glu Glu Val Phe Leu
                500                 505                 510
Ala Leu Arg Glu Arg Ala Arg Lys Glu Ala Glu Ala Leu Arg Glu Ala
                515                 520                 525
Ala Arg Ile Leu Ala Glu Leu Asp Val Tyr Ala Ala Leu Ala Glu Val
                530                 535                 540
Ala Val Arg His Gly Tyr Thr Arg Pro Arg Phe Gly Glu Arg Leu Arg
545                 550                 555                 560
Ile Arg Ala Gly Arg His Pro Val Val Glu Arg Arg Thr Ala Phe Val
                565                 570                 575
Pro Asn Asp Leu Glu Met Ala His Glu Leu Val Leu Val Thr Gly Pro
                580                 585                 590
Asn Met Ala Gly Lys Ser Thr Phe Leu Arg Gln Thr Ala Leu Ile Ala
                595                 600                 605
Leu Leu Ala Gln Ile Gly Ser Phe Val Pro Ala Glu Ala Glu Leu
                610                 615                 620
Pro Leu Phe Asp Gly Ile Tyr Thr Arg Ile Gly Ala Ser Asp Leu
625                 630                 635                 640
Ala Gly Gly Lys Ser Thr Phe Met Val Glu Met Glu Glu Val Ala Leu
                645                 650                 655
Val Leu Lys Glu Ala Thr Glu Arg Ser Leu Val Leu Leu Asp Glu Val
                660                 665                 670
Gly Arg Gly Thr Ser Ser Leu Asp Gly Val Ala Ile Ala Thr Ala Leu
                675                 680                 685
Ala Glu Ala Leu His Glu Arg Arg Cys Tyr Thr Leu Phe Ala Thr His
                690                 695                 700
```

```
Tyr Phe Glu Leu Thr Ala Leu Ala Leu Pro Arg Leu Lys Asn Leu His
705                 710                 715                 720

Val Ala Ala Lys Glu Glu Gly Gly Leu Val Phe Tyr His Gln Val
            725             730             735

Leu Pro Gly Pro Ala Ser Lys Ser Tyr Gly Val Glu Val Ala Glu Met
            740             745             750

Ala Gly Leu Pro Lys Glu Val Val Glu Arg Ala Arg Ala Leu Leu Ser
        755             760             765

Ala Met Ala Ala Arg Arg Glu Gly Ala Leu Glu Glu Val Leu Glu Arg
    770             775             780

Leu Leu Ala Leu Asp Pro Asp Arg Leu Thr Pro Leu Glu Ala Leu Arg
785             790             795                 800

Phe Leu His Glu Leu Lys Ala Leu Ala Leu Gly Leu Pro Leu Gly Ser
            805             810             815

Met Lys Gly
```

METHOD FOR ISOLATING TARGET NUCLEIC ACID USING HETERODUPLEX BINDING PROTEINS

RELATED APPLICATIONS

This Application is a continuation of U.S. application Ser. No. 15/575,699, filed Nov. 20, 2017, which is a national stage filing under 35 U.S.C. 371 of International Patent Application No. PCT/IB2016/000796, filed May 19, 2016, which claims priority to and the benefit of U.S. Provisional Application No. 62/164,247, filed May 20, 2015, and U.S. Provisional Application No. 62/291,222, filed Feb. 4, 2016. The entire contents of these applications are incorporated herein by reference.

TECHNICAL FIELD

The invention relates to methods and apparatus for isolating target nucleic acid from background nucleic acid, such as isolating mutant nucleic acid from wild-type nucleic acid. The invention also relates to enriching a sample for nucleic acid mutations as part of a diagnostic workflow.

BACKGROUND

Standard nucleic acid separation techniques limit researchers' abilities to analyze samples for nucleic acids that are present in low abundance, such as nucleic acids having point mutations. In particular, it is difficult to resolve rare nucleic acids that are present at low concentrations in the presence of closely-related nucleic acids, e.g., wild-type DNA. The difficultly of separating nucleic acids in low abundance from background nucleic acids has limited the use of techniques, such as circulating tumor DNA analysis, to instances where the mutant DNA is present in sufficient concentration to be resolved amid the background. However, in the case of a solid tumor, the tumor may have to grow to an appreciable size to produce enough circulating DNA to be resolved from the background in a serum sample. Better methods of resolving rare nucleic acids will allow for detection and treatment at earlier stages of a disease.

When the exact nature of the mutation(s) in the rare nucleic acids is known, it is possible to separate rare nucleic acid from background nucleic acid by binding with highly-specific ligands, such as hybridization probes or antibodies raised against the sequence. However, such methods are not generally applicable to resolving unknown target nucleic acid amid a background of similar nucleic acid because the probes or antibodies are only useful for recovering specific targets. As a consequence, a variety of specialty probes must be used to screen for even a small number of target nucleic acids. As a result, previously uncategorized mutations may not be isolated from the background nucleic acids at all. Additionally, even when the desired mutations are known, it is difficult to search for many known mutations at once, as individual probes (or probe sets) are required for each mutation.

Thus, there is a need for techniques that can generally separate closely-related nucleic acids for sequencing or other characterization, especially over a large range of mutations or genes. In particular, there is a need for techniques to isolate nucleic acids having unknown mutations in a nucleic acid sample.

SUMMARY OF THE INVENTION

The invention is a method for separating target nucleic acid from background nucleic acid using heteroduplex binding proteins, such as MutS. The heteroduplex binding protein preferentially binds to heteroduplexed nucleic acids, creating a heteroduplex binding protein-nucleic acid complex that has a different mobility in a separation medium as compared to homoduplex nucleic acids. When coupled with the described separation techniques, it is possible to isolate and recover target nucleic acid from background nucleic acids when only one target nucleic acid is present for each 100,000 background nucleic acids. Additionally, using the disclosed apparatus, the isolated heteroduplexes are recovered in a concentrated aqueous product, making additional analysis, e.g., sequencing, quite straightforward.

While MutS binding protein recognizes certain heteroduplexes, it fails to recognize certain other heteroduplexes. It is thought that this is in part due to a lack of flexibility in certain heteroduplexes preventing binding of the MutS protein. Some aspects of the invention relate to the nicking of heteroduplex nucleic acids at a mismatch site to increase flexibility and promote MutS recognition and binding during separation in a separation medium of the invention.

In some embodiments, the target nucleic acid includes a mutation, for example a known or an unknown mutation, such as a polymorphism, insertion, or deletion. In some embodiments, the background nucleic acids are wild-type sequences. The methods of the invention are well-suited for the isolation of mutations in oncogenes, e.g., for the detection of cancer, cancer typing, or to determine the progression of cancer in humans. Typically a sample from a subject, such as cell-free DNA from blood serum, blood plasma, urine, or tears, is processed to isolate nucleic acids, and the nucleic acids are amplified with primers selected to increase the number of nucleic acids for separation. The amplified products are denatured and then allowed to reanneal with a molar excess of reference nucleic acid to create a mixture of homoduplexed and heteroduplexed nucleic acid. The reference nucleic acid may comprise, e.g., capture probes including sequences that arc biomarkers for disease. Such reference nucleic acids are available from a variety of suppliers, such as Integrated DNA Technologies (Coralville, Iowa). The mixture of homoduplexed and heteroduplexed nucleic acids is then loaded on a separation medium comprising a heteroduplex binding protein. Because of the heteroduplex binding proteins, the mobility of the heteroduplexed nucleic acid is markedly different from the homoduplexed nucleic acids, allowing the heteroduplex nucleic acids to be easily separated from the homoduplexed nucleic acid using combined time-varying driving fields and time-varying mobility varying fields. Once separated, the heteroduplex nucleic acid can be denatured and the target nucleic acid sequenced, giving key information about the structure of the target nucleic acid.

In another aspect, the invention provides methods for recovering target nucleic acid from a sample by enriching the sample for heteroduplexes containing the target nucleic acid. Using these methods, the invention facilitates creation of a subsample in which the target that was present in only a small amount in the original sample becomes the dominant nucleic acid species in the subsample. Furthermore, it is not necessary to know the sequence of the target nucleic acid prior to performing the enrichment. As a result, unknown mutations are readily separated for further analysis. Such techniques are especially useful in rapidly isolating mutated sequences in pathogens, e.g., pathogenic bacteria or viruses.

In some embodiments, the invention provides the additional benefit of allowing isolation and recovery of target mutations without the need to amplify a nucleic acid sample prior to the isolation. This technique reduces the likelihood that mutations detected at low concentration are merely transcription errors introduced during amplification, e.g., PCR. Furthermore, when determining ratios of mutant to wild-type nucleic acids, the accuracy of the determined ratio is improved when the sample is not amplified. The type and amount of mutant nucleic acids in a sample can be used to identify the presence of a disease, the stage of a disease, and/or to evaluate the efficacy of a treatment for the disease.

Further aspects of the invention and features of specific embodiments of the invention are described below.

BRIEF DESCRIPTION OF THE DRAWINGS

FIG. 10 depicts mobility differences with temperature for a heteroduplex-binding protein nucleic acid complex and a homoduplexed nucleic acid. The choice of low and high field temperatures allows separation of the heteroduplex nucleic acid complex;

In FIG. 19A the target nucleic acid includes a star indicating the location of a mutation;

In FIG. 22A the target nucleic acid includes a star indicating the location of a mutation.

DESCRIPTION

Figure 1A:
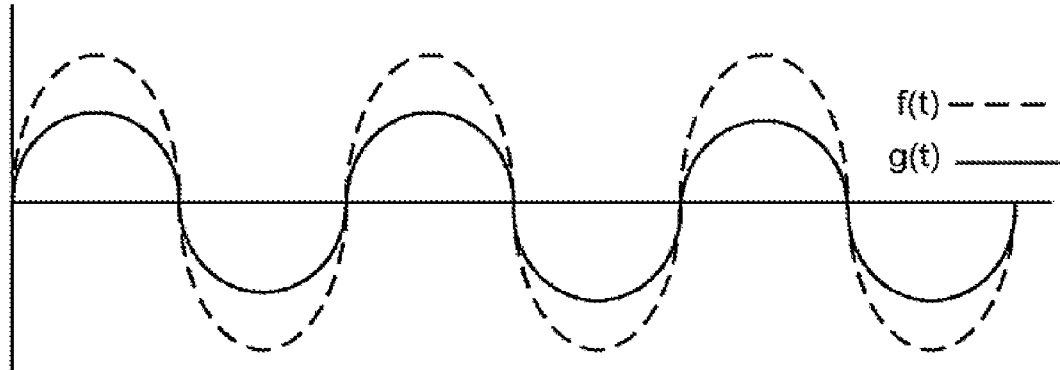
FIG. 1A shows an exemplary waveform for driving and mobility-modifying fields.

The invention includes methods and apparatus for isolating target nucleic acids by combining the target nucleic acid with reference nucleic acid to produce mixture of heteroduplex and homoduplex nucleic acid, introducing the mixture of heteroduplex and homoduplex nucleic acid to a separation medium comprising heteroduplex-binding protein, and then separating the heteroduplex and homoduplex nucleic acids using time varying separation fields. Typically a sample comprising nucleic acid will be amplified, denatured, and then mixed with a molar excess of related target capture probes (e.g., synthetic reference strands) to allow heteroduplexed and homoduplex nucleic acids to form. In certain embodiments, target nucleic acids may be modified or nicked at one or more mismatch sites prior to separation in order to promote recognition and binding of the heteroduplex-binding protein. The sample may originate from a biological sample such as a cell-free DNA sample recovered from human serum or plasma. Other nucleic acid manipulations such as amplification and addition of adapters and/or unique molecular bar codes may also be included in the work flow. The post-separation analysis may include amplification, sequencing, and/or detection. Accordingly, the invention is a powerful bioanalytical tool that can be used for advanced separation or used as part of a broader diagnostic or research workflow.

Methods of the invention additionally provide the ability to isolate low-abundance biological molecules, such as mutant nucleic acids, from a sample. The methods described can resolve a target nucleic acid present at 1:100,000 against a background of similar nucleic acid. Additionally, the method is not dependent upon the target having a predetermined sequence. Rather, the method is generally applicable to resolve rare nucleic acids with small differences from the background. The invention provides for enriching low-abundance variants of a biological molecule relative to more common, or wild-type, variants of the molecule. In preferred embodiments, methods of the invention are used to create a subsample in which a mutant that was present in the original sample in low-abundance relative to a more common species (e.g., a mutated nucleic acid and its wild-type equivalent) is present in relative high abundance in the subsample.

The invention described may be used to resolve a large number of different mutations in a single sample and/or when the mutations are substantially outnumbered by wild-type or other nucleic acid. Such applications are especially valuable when doing "liquid biopsy" or non-invasive prenatal testing (NIPT), i.e., where the target sequences may be a small fraction of the nucleic acids recovered. While it is possible to simply amplify, denature, and reanneal the sample to form a mixture of hetero- and homoduplex nucleic acids, the majority of the reannealed target nucleic acids end up with non-specific hybridization matches; i.e., because a mutant allele can't "find" its corresponding match before annealing. Once in a non-specific hybridization complex, the target nucleic acids are difficult to separate from the background because all of the non-specific hybridization matches have roughly equal electrophoretic mobility. By adding a molar excess of capture probes that create specific-binding heteroduplexes or homoduplexes, there is a much greater chance that the resulting double-stranded nucleic acids will have only one (or no) mismatch(es). Having made such a mixture, it is straightforward to resolve the heteroduplexes from the homoduplexes using the described methods.

Often the methods of the invention are used on a mixture of heteroduplexed and homoduplexed nucleic acid strand pairings resulting from targeted amplification of a gene of interest. In this embodiment, nucleic acid from a sample, e.g., genomic DNA, is amplified with primers targeted for a sequence of interest. After several amplification cycles, e.g., two or more amplification cycles, e.g., three or more amplification cycles, e.g., four or more amplification cycles, e.g., less than five amplification cycles, the amplicons are denatured, mixed with a molar excess of capture probes, and reannealed to create a mixture of homoduplexed and heteroduplexed nucleic acid strand pairings. In some embodiments, a greater number of amplification cycles are used prior to reannealing, e.g., 20 cycles or more, e.g., 40 cycles or more, e.g., 60 cycles or more, e.g., 80 cycles or more, e.g., 100 cycles or more. The sample may be any biological sample comprising nucleic acids, such as blood, plasma, serum, sweat, saliva, sputum, urine, stool, tears, hair, tissue, exhaled breath, or a buccal swab. In some instances, the invention allows resolution of target nucleic acids without amplification, and without regard for the sequence difference between a nucleic acid and a variant of it.

Accordingly, use of the invention allows detection and analysis of nucleic acids present in low abundance in biological samples. The ability to interrogate low-abundance nucleic acids is especially important in cancer diagnostics, where early detection enables effective treatment. For example, identification of the presence of a specific mutation may suggest a particular treatment regimen (e.g., surgery versus radiation therapy) or suggest that a first line treatment is likely to be ineffective, (e.g., the cancer is resistant to docetaxel). Additionally, when mutational events are detected earlier, patients typically have more options for treatment, as well as the time to identify a preferred treatment provider. The methods of the invention are especially useful for recovering cell-free DNA, such as DNA that is circulating in the blood serum or found in urine.

Methods of the invention are useful in many types of samples. Preferred samples are derived from tissue or body fluid, for example, tissues, blood, plasma, sputum, serum, sweat, urine, tears, feces, aspirates, or a combination thereof. Typically, the biological sample will be from a human, however the methods of the invention may be used to recover nucleic acids from many organisms, including, mammals. In other applications, the methods can be used to identify variations in organism such as plants, fungi, bacteria, or viruses. Thus, the invention allows for rapid detection of mutations that may be responsible for crop failures, epidemics, or a biological weapon attack.

Once a sample is enriched for a target, it will typically be useful to identify the target using sequencing, hybrid capture, antibodies or other known techniques. Once the target nucleic acid is identified, it will be possible to correlate its presence in the sample with a condition, or a likely outcome for the subject from which the sample was taken. For example, the presence of the target nucleic acid may be indicative of a genetic disorder or cancer. Additionally, because the methods of the invention can be used to enrich a sample for multiple targets (serially or in parallel), the invention lends itself to diagnosing diseases by identifying specific biomarker panels that correlate with specific diseases. In some instances the invention will allow the identification of 5 or more targets, e.g., 10 or more targets, e.g., 20 or more targets, e.g., 50 or more targets, e.g., 100 or more targets. Furthermore, when screening panels comprising multiple biomarkers are used, the confidence in the resulting diagnosis is increased. That is, a diagnosis based upon identifying one target nucleic acid may be the result of noise or error, but when a diagnosis is based upon identifying 10 or more targets simultaneously, it is very likely not the result of noise or error.

The skilled artisan will appreciate that there are numerous ways to practice the invention described and claimed herein. However, one preferred embodiment is exemplified below using a technique called scodaphoresis or SCODA (Synchronous Coefficient of Drag Alteration). Scodaphoresis refers to methods for moving and/or concentrating particles in a medium. Scodaphoresis involves exposing particles that are to be moved and/or concentrated to two time-varying fields or stimuli. A first one of the fields results in a force f(t) that drives motion of the particles in the medium. The direction of particle motion caused by the interaction of the particle with the first field varies in time. The first field may provide a driving force that averages to zero over an integral number of cycles of the first field.

A second one of the fields alters the mobility of the particles in the medium according to a function g(t). The first and second fields are such that f(t) and g(t) have a non-zero correlation over a time period of interest. Achieving such a non-zero correlation can be achieved in various ways. In some embodiments, f(t) and g(t) are each time varying at the same frequency and f(t) and g(t) are synchronized so that there is a substantially constant phase relationship between f(t) and g(t). In other embodiments, f(t) has a frequency that is twice that of g(t).

Application of the fields to the particles causes a net drift of the particles. This net drift can be harnessed to separate particles of different types or to concentrate (enrich) particles in selected areas, or both. As discussed below, the first and second fields may be of the same type (homogeneous SCODA) or of different types (heterogeneous SCODA).

As a demonstration of SCODA, consider the case where:

$$f(t)=\sin(\omega t), g(t)=\sin(\omega t), \text{ and } v(f(t), g(t))=f(t)\times(\mu_0+\mu_1 g(t)) \quad (1)$$

where $\mu_0$, is the unperturbed mobility of the particle in the medium and $\mu_1$ is the susceptibility of the mobility to g(t). It can be seen that in the absence of g(t), the velocity of the particle is given simply by $\mu_0 f(t)$. Where f(t) is given by Equation (1) there is no net displacement of the particle over a cycle of f(t). Where g(t) is as given above, however, over one cycle, the velocity integrates to yield a distance, d, traveled by the particle of:

$$d = \int_{t=0}^{2\pi/\omega} \mu_1 \sin^2(\omega t)dt = \frac{\mu_1 \pi}{\omega} \quad (2)$$

Thus, the simultaneous application of the two fields imparts a net motion to the particle. In this example, the net motion is independent of $\mu_0$.

"Particle" is used herein to mean any microscopic or macroscopic thing that can be moved by scodaphoresis.

The correlation of f(t) and g(t) may be computed according to a suitable correlation function such as:

$$C_{f(t),g(t)} = \int_T f(t)g(t+\lambda)dt \quad (3)$$

where C is the correlation, T is a period of interest, and $\lambda$ is a constant time shift. C must have a non-zero value for some value of $\lambda$.

Ideally f(t) and g(t) have a large correlation for efficient operation of SCODA, but some SCODA motion can occur even in cases where the chosen functions f(t) and g(t) and the chosen value of $\lambda$ result in small values of C. The velocity of the particle undergoing SCODA motion must be a function of both f(t) and g(t). Further, the velocity of the particle as a result of the application of f(t) and g(t) together must not be the same as the sum of the velocities resulting from application of f(t) and g(t) independently. That is:

$$\vec{v}(f(t),g(t)) \neq \vec{v}(f(t),0) + \vec{v}(0,g(t+\lambda)) \quad (4)$$

One set of conditions which is convenient, but not necessary, for scodaphoresis is:

$$\int_{-\infty}^{\infty} f(t)dt = 0, \int_{-\infty}^{\infty} g(t)dt = 0, \quad (5)$$

$$\int_{-\infty}^{\infty} v(f(t), 0)dt = 0, \text{ and } \int_{-\infty}^{\infty} v(0, g(t))dt = 0$$

where v(f(t),0) is the velocity of a particle as a function of time when the particle is interacting only with the driving field f(t); v(0,g(t)) is the velocity of a particle as a function of time when the particle is interacting only with the mobility-varying field g(t); and, $$\int_{-\infty}^{\infty} v(f(t), g(t))dt \neq 0 \quad (6)$$

in this case, the two fields, acting independently, do not produce any net motion of the particle. However, the combined effect of the first and second fields does result in the particle being moved with a net velocity.

To optimize SCODA one can select functions f(t) and g(t) so that the first order velocity of the particles caused by either f(t) or g(t) is zero (so particles have no net drift), and so that the combination of f(t) and g(t) acts on the particles to provide a maximum velocity. One can select f(t) and g(t) and a phase shift $\lambda$ to maximize the integral:

$$\int_0^T \vec{v}(f(t), g(t+\lambda))dt \quad (7)$$

The process in this case runs from time 0 to time T or possibly for multiple periods wherein t runs from 0 to T in each period.

It is not necessary that f(t) and g(t) be represented by sinusoidal functions, by the same functions, or even by periodic functions. In some embodiments of the invention, f(t) and g(t) are different functions. In some embodiments of the invention, f(t) and g(t) are not periodic. FIGS. 1A through 1H show some examples of functions f(t) and g(t) that could be used in specific embodiments of the invention.

Figure 1B:
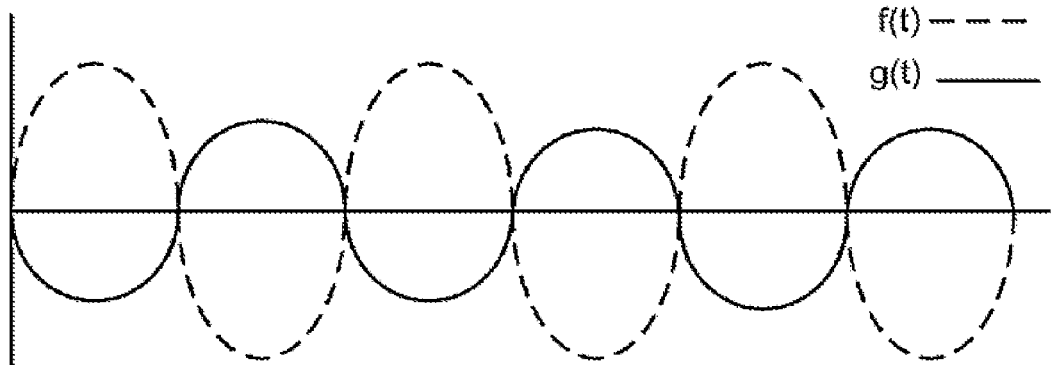
FIG. 1B shows an exemplary waveform for driving and mobility-modifying fields.

FIG. 1A shows a case wherein f(t) and g(t) are both sine functions with f(t) and g(t) in phase. FIG. 1B shows a case where f(t) and g(t) are both sine functions with f(t) and g(t) out of phase. As described below, the direction in which particles are caused to move can be reversed by altering the relative phase of f(t) and g(t).

Figure 1C:
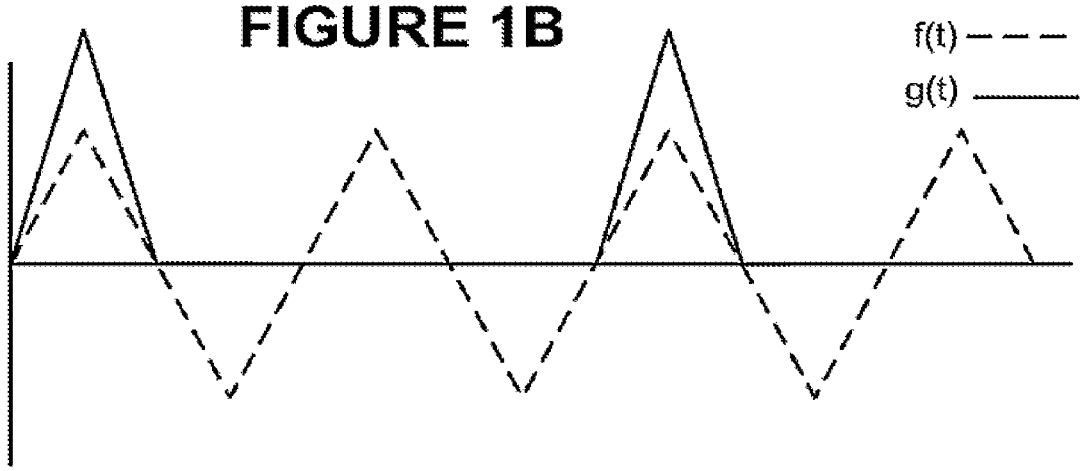
FIG. 1C shows an exemplary waveform for driving and mobility-modifying fields.
Figure 1D:
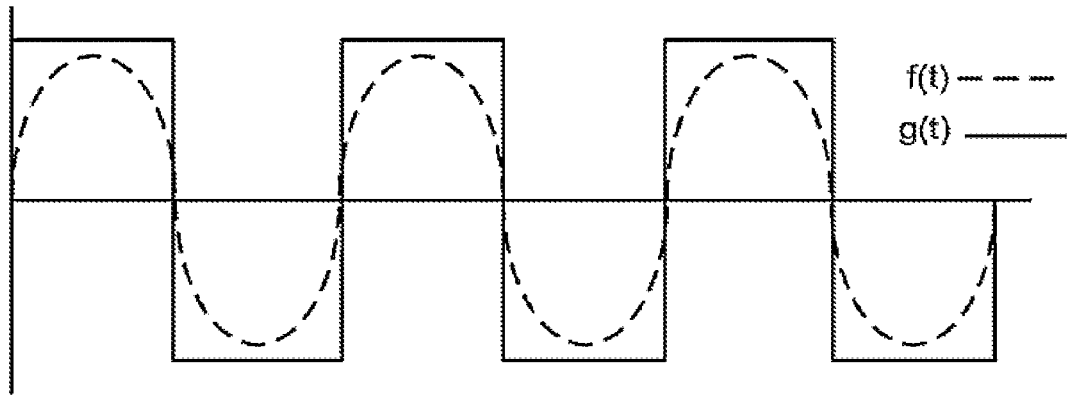
FIG. 1D shows an exemplary waveform for driving and mobility-modifying fields.
Figure 1E:
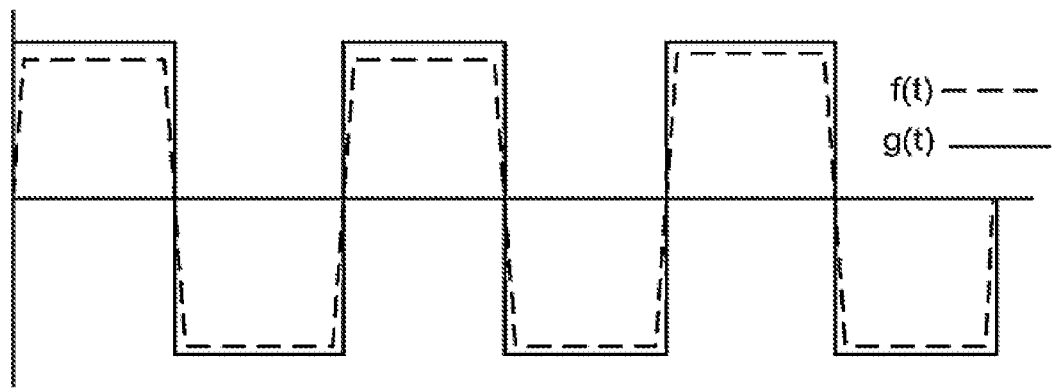
FIG. 1E shows an exemplary waveform for driving and mobility-modifying fields.
Figure 1F:
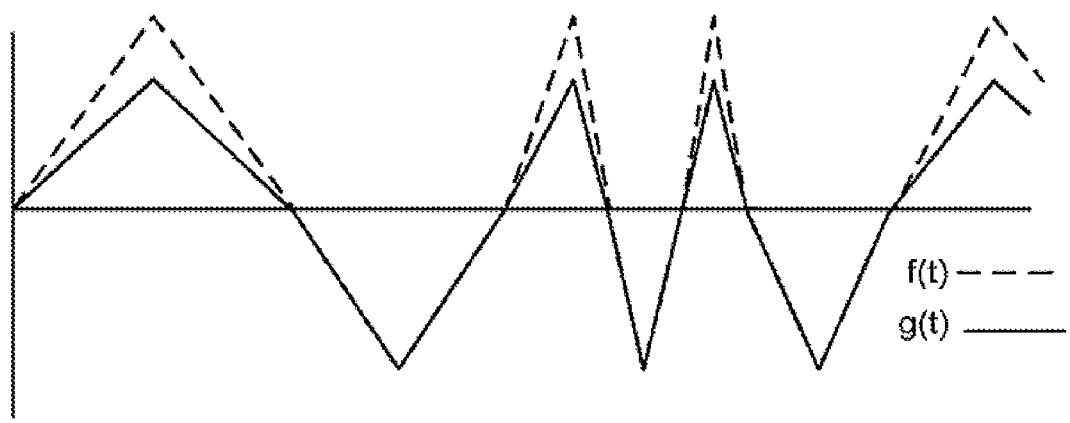
FIG. 1F shows an exemplary waveform for driving and mobility-modifying fields.
Figure 1G:
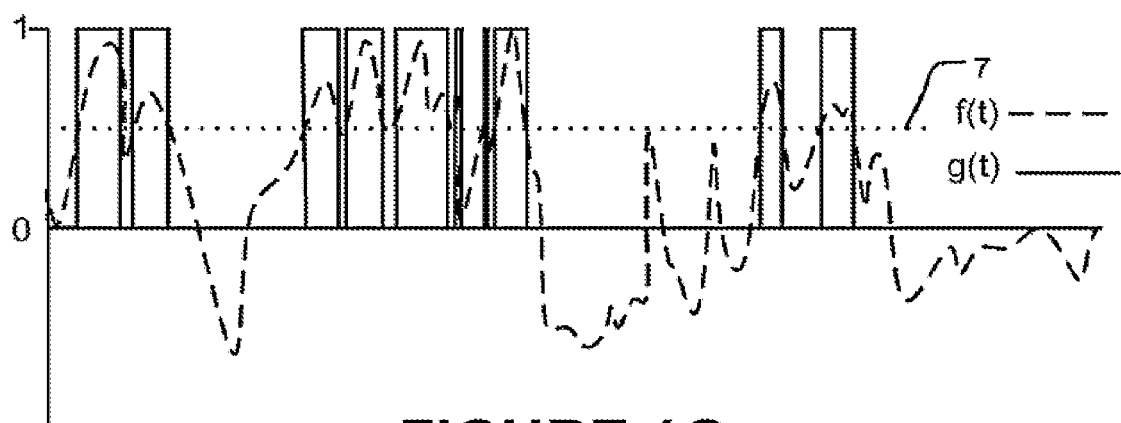
FIG. 1G shows an exemplary waveform for driving and mobility-modifying fields.
Figure 1H:
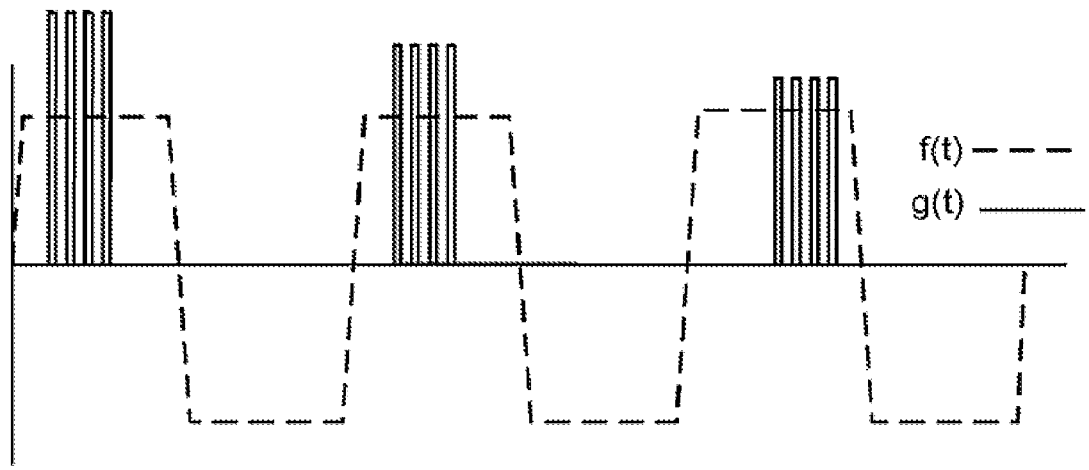
FIG. 1H shows an exemplary waveform for driving and mobility-modifying fields.

FIG. 1C shows a case where g(t) is unbalanced. In FIG. 1C, f(t) and g(t) are both triangular functions. In FIG. 1C g(t) has a frequency half of that of f(t). In FIG. 1D, f(t) has a square waveform while g(t) has a sinusoidal waveform. In FIG. 1E, f(t) and g(t) both have substantially square waveforms. In FIG. 1F, f(t) and g(t) have varying frequencies. In FIG. 1G, f(t) is essentially random noise and g(t) has a value of 1 (in arbitrary units) when f(t) exceeds a threshold 7 and has a value of 0 otherwise. In FIG. 1H, g(t) has the form of a series of short-duration impulses.

As another example, $$f(t) = \sin(\omega t), \; g(t) = 1 \; \text{for} \; \frac{2n\pi}{\omega} < t < \frac{(2n+1)\pi}{\omega} \quad (8)$$

where n is any integer or set of integers (e.g. $n \in \{1, 2, 3, \ldots\}$ or $n \in \{2, 4, 6, \ldots\}$ or $n \in \{1, 4, 7, \ldots\}$. The integers n do not need to be regularly spaced apart. For example, the methods of the invention could be made to work in a case wherein the set of integers n consists of a non-periodic series. An otherwise periodic waveform f(t) or g(t) could be made aperiodic by randomly omitting troughs (or peaks) of the waveform, for example.

Figure 1I:
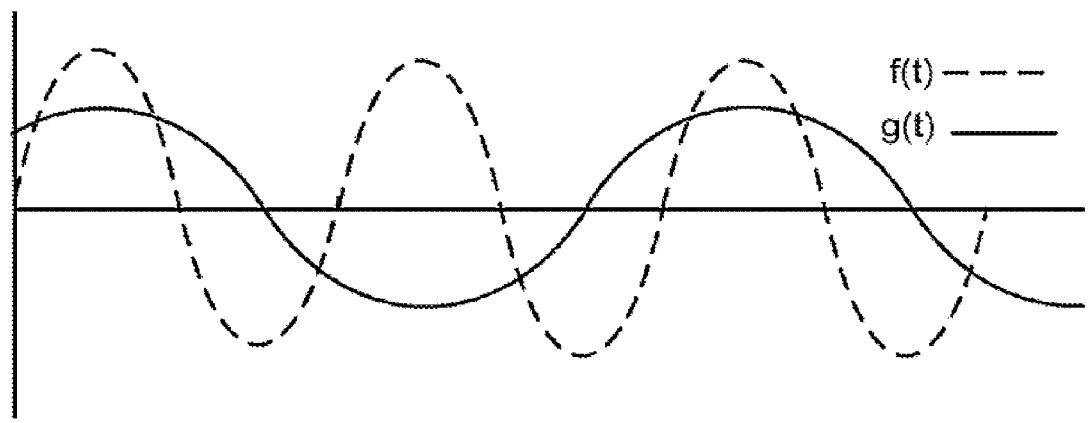
FIG. 1I shows an exemplary waveform for driving and mobility-modifying fields.

FIG. 1I illustrates a case where f(t) has a frequency twice that of g(t). The waveforms of FIG. 1I can produce SCODA motion, for example, where the mobility of particles varies in response to |g(t)|. It can be seen that |g(t)| has larger values for positive-going peaks of f(t) than for negative-going peaks of f(t).

While the waveforms shown in most of FIGS. 1A to 1I are symmetrical (i.e. they have the same overall form if inverted in spatial direction) this is not mandatory. f(t) could, in general, be asymmetrical.

Driving Fields f(t) is referred to herein as a driving function because it drives motion of the particles in the medium. In different embodiments of the invention, f(t) is produced by fields of different types. For example, f(t) may be produced by any of:
  a time-varying electric field;
  a time-varying magnetic field;
  a time-varying flow in the medium;
  a time-varying density gradient of some species in the medium;
  a time-varying gravitational or acceleration field (which may be obtained, for example by accelerating a medium containing particles and periodically changing an orientation of the medium relative to the direction of the gravitational or acceleration field);
  or the like.

In some embodiments, f(t) applies a force to particles that alternates in direction wherein the magnitude of the force is the same in each direction. In other embodiments, f(t) combines a component that alternates in direction and a bias component that does not alternate in direction such that the magnitude of the force applied to particles is larger in one direction than in the other. The bias component may be termed a DC component while the alternating component may be termed an AC component.

The driving field is selected to interact with the particles of interest. For example:

Where the particles are electrically charged particles (ions for example), an electric field may be used for the driving field. Electrically neutral particles may be made responsive to an electric field by binding charged particles to the electrically neutral particles. In some cases an electrically neutral particle, such as a neutral molecule, can be carried by a charged particle, such as a charged molecule. For example, neutral proteins that interact with charged micelles may be driven by an electrical driving field through the interaction with the driving field and the micelles.

Where the particles have dielectric constants different from that of the medium, an electric field having a time-varying gradient can drive motion of the particles through the medium by dielectrophoresis.

Where the particles contain magnetic material (for example, where particles of interest can be caused to bind to small beads of a type affected by magnetic forces, for example ferromagnetic beads) a magnetic field may be used for the driving field.

Where the particles have magnetic susceptibilities different from that of the medium then a gradient in a magnetic field may be used to drive motion of the particles relative to the medium by magnetophoresis.

Where the particles have densities different from that of the medium then a gravitational or other acceleration acting on the particles may drive motion of the particles relative to the medium. An AC acceleration is provided in some embodiments by exposing the medium to an acoustic field.

The driving field may directly apply a force to the particles or may indirectly cause motion of the particles. As an example of the latter, the driving field may cause living particles (mobile bacteria for example) to move in response to their own preference for certain environments. For example, some organisms will swim toward light, chemical gradients, or magnetic fields (these phenomena are known as chemotaxis, phototaxis, and magnetotaxis respectively).

Mobility-Varying Fields

The mobility of particles may by altered according to any of a wide variety of mechanisms. For example:
  changing a temperature of the medium;
  exposing the particles to light or other radiation having an intensity and/or polarization and/or wavelength that varies in time with the driving field;
  applying an electric field to the portion of the medium through which the particles are passing;
  applying a magnetic field to the medium through which the particles are passing (the magnetic field may, for example, alter an orientation of a magnetic dipole associated with the particle and thereby affect a coefficient of drag of the particle or alter a viscosity of the medium which may comprise a suitable magneto-rheological fluid);
  applying an acoustic signal to the portion of the medium through which the particles are passing;
  causing a cyclic change in concentration of a species in the medium;
  exploiting electroosmotic effects;
  causing cyclic chemical changes in the medium;
  causing the particles to cyclically bind and unbind to other particles in or components of the medium;

varying a hydrostatic pressure experienced by the medium;

varying physical dimensions of the medium to cause a change in an effective drag experienced by particles in the medium;

applying magnetic fields to the medium.

Any effect that varies the mobility of a particle in response to a driving field, such as an electrophoretic driving field, can be used.

In some embodiments of the invention, the mobility of particles is varied by exploiting non-linearities in the relationship between the velocity of a particle and the intensity of the driving field. Some embodiments apply a second driving field having a component acting perpendicular to the direction of the first driving field but a frequency half that of the first driving field. Applied by itself, such a second driving field would simply cause particles to oscillate back and forth in a direction perpendicular to the direction of the main driving field. When applied together with the main driving field, however, such a second driving field can cause particles to have higher average speeds relative to the medium for one direction of the main driving field than for the other direction of the main driving field. This results in a net drift of the particles because of the non-linear relationship between particle mobility and particle speed. In some embodiments the main driving field has a symmetrical waveform, such as a sinusoidal, triangular or square waveform.

A temperature of the medium in which the particles are situated may be altered in time with the driving field. The changing temperature may result in a change in one or more of a conformation of the particles, a viscosity of the medium, a strength of interaction between the particles and the medium, some combination of these, or the like. The result is that the mobility of the particles is altered by the change in temperature. The temperature of regions in a medium may be controlled in any suitable manner including:

directing radiation at the portion of the medium to heat that portion of the medium;

energizing heaters or coolers in thermal contact with the portion of the medium;

causing endothermic or exothermic chemical reactions to occur in the portion of the medium (or in a location that is in thermal contact with the portion of the medium); and, the like.

In some embodiments of the invention the medium comprises a material that absorbs radiation and releases the absorbed radiation energy as heat. In some embodiment, localized heating of the medium in the vicinity of the particles being moved is achieved by irradiating the particles with electromagnetic radiation having a wavelength that is absorbed by the particles themselves and released as heat. In such embodiments it can be advantageous to select a wavelength for the radiation that is not absorbed or converted to heat significantly by constituents of the medium so that heating is local to the particles.

Some examples of particles that have mobilities that vary with temperature are: proteins that can be cyclically denatured or caused to fold in different ways by cyclically changing the temperature; and DNA that can be cyclically denatured.

Exposing the area of the medium in which the particles are travelling to radiation changes one or more of: a conformation of the particles, a viscosity of the medium, a strength of interaction between the particles and the medium, some combination of these, or the like. The result is that the mobility of the particles is altered by changes in the intensity and/or polarization and/or wavelength of the applied radiation. Some examples of particles that have mobilities that can be caused to change by applying light are molecules such as azobenzene or spiro-pyrans, that can be caused to undergo reversible changes in conformation by applying light. Another example of the use of light to vary the mobilities of particles in a medium is the application of light to cause partial cross-linking of polymers in a medium containing polymers.

The intensity of an electric field applied to the medium may be varied in time with the driving field. In some media the mobility of particles of certain types varies with the applied electric field. In some media the particle velocity varies non-linearly with the applied electric field.

The mobility of particles in a medium may vary with the intensity of an acoustic field applied to the medium. In some cases, an acoustic standing waves in a solution or other medium may cause transient differences in local properties of the medium (e.g. electrical resistivity) experienced by particles in the medium thus leading to local inhomogeneity in the driving field (e.g. a driving electric field).

Where mobility of particles is controlled by altering a concentration of a species, the species having the varying concentration may, for example, be a species that binds to the particles or a species that affects binding of the particles to some other species or to a surface or other adjacent structure. The species may directly affect a viscosity of the medium.

As an example of the use of electroosmotic effects to control particle mobility, consider the case where the medium in which the particles are moving is a solution containing one or more polymers. In such solutions, an applied electric field can cause bulk fluid flow. Such a flow could be controlled to provide a perturbing stimulus to a pressure or flow induced driving force, or as a perturbation to an electrical driving force, possibly exploiting non-linearities in the onset of electroosmotic flow.

Chemical changes that are exploited to control particle mobility may, for example, induce changes in one or more of:

a conformation of the particles;

a conformation of some other species;

binding of the particles to one another or to other species or structures in the medium;

binding of species in the medium to one another;

viscosity of the medium; or the like.

The chemical changes may be induced optically, for example, by optically inducing cross-linking or by optically inducing oxidation or reduction of photoactive molecules such as ferrocene. The chemical changes may be induced by introducing chemical species into the medium. The chemical changes may include one or more of changes: that alter the pH of the medium; changes that result in changes in the concentration of one or more chemical species in the medium; or the like.

Particle mobility may be affected by applied magnetic fields according to any of a variety of mechanisms. For example:

The medium may contain small magnetic beads. The beads may be linked to polymers in a polymer matrix. By applying a magnetic field, the beads may be pulled away from a path of the particles, thereby reducing an effective viscosity of the medium experienced by the particles.

The medium could be a magneto-rheological fluid having a viscosity that varies with applied magnetic field.

A magnetic field may be used to cause medium viscosity to vary according to a two-dimensional pattern. The magnetic field could change in time in such a manner that the viscosity of the medium varies with position and varies in time in a manner that provides a synchronous perturbation to a periodic driving force. As another example, where the particles themselves are magnetic, transport and concentration of the particles could be affected by a magnetic field. The particles could be driven electrophoretically. The magnetic field could be switched on periodically to drive the particles toward a drag-inducing surface, or release them from such a surface. The magnetic field could also be used to make the particles aggregate.

Particles

The methods of the invention may be applied to particles of virtually any kind including molecules, ions, and larger particulates. Some non-limiting examples of particles which may be moved, concentrated and/or extracted through use of the methods of the invention are:

- electrically charged or neutral biomacromolecules such as proteins, nucleic acids (single-stranded and double-stranded RNA, DNA), and suitable lipids; long polymers; polypeptides;
- aggregations of molecules such as micelles or other supramolecular assemblies;
- any particles to which magnetic beads or electrically-charged beads can be attached;
- living microorganisms; and,
- the like.

In particular the invention is effective at separating nucleic acids, which may be single-stranded or double stranded, and may vary in length from thousands of bases, to hundreds of bases, to tens of bases. The invention may also be used to separate homoduplexes of double stranded nucleic acids from heteroduplexes of nucleic acids. In one instance, the invention is used to separate or enrich so called short nucleic acids, having 500 or fewer, e.g., 200 or fewer, e.g., 100 or fewer, e.g., 50 or fewer bases. Short nucleic acids are commonly the result of cellular breakdown, and may be found, for example, in cell-free samples (e.g., blood plasma, urine), formalin-fixed samples, or forensic samples.

For any particular type of particle, one can attempt to identify a suitable driving field, medium, and mobility-altering field. Since many biomacromolecules can be electrically charged, it is often suitable to use a time-varying electrical field as the driving field when applying the invention to moving and/or concentrating such particles. Further, there are well developed techniques for causing magnetic beads to bond to specific biological materials. Where it is desired to move and/or concentrate materials which can be caused to bond to magnetic beads then magnetic fields may be used as driving fields.

Media

The medium is selected to be a medium through which the particles can move and also a medium wherein the mobility of the particles can be altered by applying a suitable mobility-altering field. The medium may comprise, for example:

- a gel, such as an agarose gel or a performance optimized polymer (POP) gel (available from Perkin Elmer Corporation);
- a solution, aqueous or otherwise;
- entangled liquid solutions of polymers;
- viscous or dense solutions;
- solutions of polymers designed to bind specifically to the molecules (or other particles) whose motion is to be directed;
- acrylamide, linear poly-acrylamide;
- micro-fabricated structures such as arrays of posts and the like, with spacing such that the particles of interest can be entangled or retarded by frequent collision or interaction with the micro-fabricated structure;
- structures designed to interact with molecules by means of entropic trapping (see, e.g. Craighead et al., in *Science* 12 May 2000 Vol. 288);
- high viscosity fluids such as PLURONIC™ F127 (available from BASF);
- water; or
- the like.

The medium is chosen to have characteristics suitable for the particles being moved. Where the particles are particles of DNA then suitable polymer gels are the media currently preferred by the inventors. In some specific embodiments of the invention the particles comprise DNA and the medium comprises an agarose gel or a suitable aqueous solution. In some embodiments the aqueous solution is a bacterial growth medium mixed with a gel such as an agarose gel.

In preferred embodiments, the media will include hetero-duplex-binding proteins, such as MutS, discussed in greater detail below.

2D Scodaphoresis

In some embodiments, the particles are constrained to move on a two-dimensional (2D) surface. In some embodiments the 2D surface is planar. The 2D surface is not necessarily planar. In some embodiments, the 2D surface comprises a relatively thin layer of a medium, such as a gel. In some embodiments the medium is free-standing. The medium may be supported on a substrate. The substrate may comprise a sheet of glass or a suitable plastic such as mylar, for example. In some embodiments the 2D layer of medium is sandwiched between the surfaces of two substrates. Where the medium has an exposed surface, the surface may be in air or another gaseous atmosphere or submerged in a liquid such as a suitable buffer, an oil, or the like. In some currently preferred embodiments, the medium comprises a layer of a gel sandwiched between two layers of thicker gel. In an example embodiment, particles move in a layer of a 1% w/v agarose gel sandwiched between two layers of 3% w/v agarose gel.

In some embodiments of the invention, a 2D surface in which particles travel may be provided by a layer within a medium which has a non-uniform viscosity or a non-uniform concentration of a species that reduces (or increases) a mobility of the particles. The viscosity or concentration gradient cause particles to remain in the relatively thin layer within the medium or on a surface of the medium.

3D Scodaphoresis

SCODA may be used to concentrate particles in three dimensions. This may be achieved in various ways. In some embodiments, 2D SCODA is performed in a plane. The 2D SCODA may be performed using the electrophoretic SCODA method described below, for example, Z electrodes placed above and below the plane could apply an electric field that tends to drive any particles that begin to move out of the plane back into the plane.

3D SCODA could also be performed by providing a 6 electrode arrangement, where each electrode is placed on the surface of a body of a medium such as a gel. Defining X Y and Z axes of such a cube, 2D SCODA would then be run on the 4 electrodes in the XY plane, then the 4 electrodes in the YZ plane, then the 4 electrodes in the XZ plane, then repeating in the XY plane and so forth. This would produce a net 3D focusing effect, with a net SCODA force that is radial in three dimensions, but about ¼ as strong as the 2D SCODA force for the same electrode voltages.

Samples

A variety of fluidic samples can be enriched using methods of the invention. Additionally, solid samples may be solubilized or suspended and then enriched. Suitable biological samples may include, but are not limited to, cultures, blood, plasma, serum, saliva, cerebral spinal fluid, pleural fluid, milk, lymph, sputum, semen, urine, stool, tears, saliva, sweat, needle aspirates, external sections of the skin, respiratory, intestinal, and genitourinary tracts, tumors, organs, cell cultures or cell culture constituents, or tissue sections. In some embodiments, the biological sample may be analyzed as is, that is, without additional preparation. In an alternate embodiment, harvest and/or isolation of materials of interest may be performed prior to analysis.

A sample may include any of the aforementioned samples regardless of their physical condition, such as, but not limited to, being frozen or stained or otherwise treated. In some embodiments, a biological sample may include compounds which are not naturally intermixed with the sample such as preservatives, anticoagulants, buffers, fixatives, nutrients, antibiotics, or the like.

In some embodiments, a biological sample may include a tissue sample, a whole cell, a cell constituent, a cytospin, or a cell smear. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines. In some embodiments, a biological sample includes tissue sections from healthy or diseased tissue samples (e.g., tissue section from colon, breast tissue, prostate, lung, etc.). A tissue section may include a single part or piece of a tissue sample, for example, a thin slice of tissue or cells cut from a tissue sample.

In some embodiments, a biological sample may be recovered from a solid support and suspended or solubilized prior to being used with methods of the invention. A solid support may include microarrays (e.g., DNA or RNA microarrays), gels, blots, glass slides, beads, swabs or ELISA plates. In some embodiments, a biological sample may be adhered to a membrane selected from nylon, nitrocellulose, and polyvinylidene difluoride. In some embodiments, the solid support may include a plastic surface selected from polystyrene, polycarbonate, and polypropylene. In some embodiments the biological sample is recovered from a formalin-fixed sample, e.g., a formalin-fixed paraffin-embedded (FFPE) sample.

A biological sample may be of prokaryotic origin or eukaryotic origin (e.g., insects, protozoa, birds, fish, reptiles). In some embodiments, the biological sample is mammalian (e.g., rat, mouse, cow, horse, pig, dog, cat, donkey, guinea pig, or rabbit). In certain embodiments the biological sample is of primate origin (e.g., example, chimpanzee, or human). The samples may be forensic samples including, but not limited to, blood samples, saliva samples, urine samples, feces samples, microbial samples, pathogen samples, forensic biological samples, crime scene biological samples, drug/alcohol samples, chemicals (e.g., explosives), and residues.

Additional Analysis of Particles

In some instances, enriched samples produced with the methods and apparatus of the invention will be additionally analyzed or processed. For example, the resultant enriched sample may be amplified, hybridized, stored, lyophilized, or sequenced.

Where the enriched sample contains nucleic acids, the sample may be amplified using Polymerase Chain Reaction (PCR) technologies. A typical PCR reaction includes multiple amplification steps, or cycles that selectively amplify a targeted nucleic acid species. Additional references describe the PCR process, and common variations thereof, such as quantitative PCR (QPCR), real-time QPCR, reverse transcription PCR (RT-PCR) and quantitative reverse transcription PCR (QRT-PCR). PCR instruments and reagents are commercially available from suppliers such as Roche Molecular Diagnostics (Pleasanton, Calif.).

A typical PCR reaction includes three steps: a denaturing step in which a targeted nucleic acid is denatured; an annealing step in which a set of PCR primers (forward and backward primers) anneal to complementary DNA strands; and an elongation step in which a thermostable DNA polymerase elongates the primers. By repeating this step multiple times, a DNA fragment is amplified to produce an amplicon, corresponding to the targeted DNA sequence. Typical PCR reactions include 30 or more cycles of denaturation, annealing and elongation. In many cases, the annealing and elongation steps can be performed concurrently, in which case the cycle contains only two steps. Using PCR amplification, it is possible to amplify the targeted nucleic acid exponentially.

However, as discussed in the background of this application, PCR amplification introduces errors into the amplified nucleic acid products. In some instances, the error rate is of the same magnitude as the incidence of target nucleic acids in the sample. In these instances if PCR amplification is used, it is done after enrichment to avoid creating erroneous target nucleic acids. In some embodiments, where the PCR error rate is acceptable compared to the incidence of target nucleic acids in the sample, it is beneficial to do some PCR on the sample prior to enrichment, to boost the total number of target nucleic acids in the sample. In practice, PCR prior to enrichment is limited to fewer than 20 cycles, e.g., 15 or fewer cycles, e.g., 10 or fewer cycles, e.g., 5 or fewer cycles, in order to limit the introduction of errors. After enrichment, the enriched target nucleic acids may be amplified for further processing with 20 or more, e.g., 25 or more, e.g., 30 or more, e.g., 40 or more PCR cycles.

Several methods are available to identify target nucleic acids (e.g., variant nucleic acids, e.g., mutations) that have been enriched using methods and apparatus of the invention. In some instances an enriched sample may be analyzed with a hybridization probe. Typically, a labeled single stranded polynucleotide, which is complementary to all or part of the targeted sequence, is exposed to the sample, a wash step is performed, and then the sample is observed for the presence of the label. In some instances, amplification and hybrid probe analysis may be performed simultaneously, e.g., using quantitative PCR.

In other instances the complementary polynucleotide probes may be immobilized on a solid support. In this instance, hybrid probe analysis typically includes (1) labeling nucleic acids in the enriched sample, (2) pre-hybridization treatment to increase accessibility of support-bound probes and to reduce nonspecific binding; (3) hybridization of the labeled nucleic acids to the surface-bound polynucleotides, typically under high stringency conditions; (4) post-hybridization washes to remove nucleic acid fragments not bound to the solid support polynucleotides; and (5) detection of the hybridized, labeled nucleic acids. Detection may be done, for example by fluorescence detection, however other methods may be used, depending upon the nature of the label.

In some embodiments, an enriched sample containing multiple target nucleic acids may be identified with a multiplex protocol designed to identify multiple specific mutations of interest. For example, single nucleotide polymorphisms (SNPs) among the target nucleic acids may be determined with a single base extension kit, such as SNAPSHOT™ available from Applied Biosystems (Life Technologies, Carlsbad, Calif.). Using this kit, the enriched sample will be mixed with a set of primers of varying length and sequence, each primer being complementary to different loci on the target nucleic acids. Upon mixing, the primers will hybridize with a specific target nucleic acid, forming a duplex with a 3' terminus adjacent to the SNP. In the presence of a polymerase, a single fluorescently-labeled base is added to the duplex and the resulting populations of fluorescently-labeled moieties can be characterized by length and label color (e.g., using Sanger sequencings, for example GENESCAN™ analysis, Applied Biosystems) to determine the presence and amount of the mutations.

Another method that can be used to identify nucleic acids in the enriched sample is genetic sequencing. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454™ sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD™ sequencing.

In preferred embodiments, the next-generation sequencing is ILLUMINA™ sequencing, available from Illumina, Inc., (San Diego, Calif.). ILLUMINA™ sequencing amplifies DNA on a solid surface using fold-back PCR and anchored primers. The DNA is then fragmented, and adapters are added to the 5' and 3' ends of the fragments. Next, fragments are attached to the surface of flow cell channels, and the DNA is extended and bridge amplified. This process results in several million clusters of approximately 1,000 copies of single-stranded DNA molecules of the same template in each channel of the flow cell. Using primers, DNA polymerase, and four fluorophore-labeled, reversibly-terminating nucleotides, the copies are then sequentially sequenced and fluorescence-imaged to determine the added nucleotide. The 3' terminators and fluorophores from each incorporated base are subsequently removed, and the incorporation, detection and identification steps are repeated to read out the next nucleotide. The methods of the invention include the addition of sequencing adapters before and/or after the separation of target nucleic acid from background nucleic acid. In some embodiments, sequencing adapters will be added to all of the nucleic acid from a sample prior to amplification of the nucleic acid. Commercial work flows and equipment, such as HiSeq™ Cluster Kits (Illumina), may be used to prepare the nucleic acids prior to separation and/or sequencing.

In other embodiments, nucleic acids enriched with methods of the invention may be sequenced using next-generation sequencing. For example, 454™ sequencing, available from Roche (Branford, Conn.), may be used to quickly and accurately sequence enriched nucleic acid samples. (See Margulies, M et al. 2005, Nature, 437, 376-380, incorporated herein by reference in its entirety.) 454™ sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to DNA capture beads, e.g., streptavidin-coated beads using, e.g., Adaptor B, which contains 5'-biotin tag. The fragments attached to the beads are PCR amplified within droplets of an oil-water emulsion to make multiple copies of DNA fragments on each bead. In the second step, the beads are captured in picoliter wells. Finally, pyrosequencing is performed on each DNA fragment in parallel. As nucleotides are added, a light signal is generated and recorded by a CCD camera in the instrument. The signal strength is proportional to the number of nucleotides incorporated. The signals are then analyzed and correlated to determine the sequence.

Alternatively, ION TORRENT™ sequencing systems, available from Life Technologies (Carlsbad, Calif.) may be used to directly obtain the sequences of the enriched nucleic acids. Among other references, the methods and devices of ION TORRENT™ sequencing are disclosed in U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In ION TORRENT™ sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are then attached to a surface at a concentration such that the fragments are individually resolvable. Addition of one or more nucleotides releases a proton ($H^+$), which is detected and recorded in a sequencing instrument. The signal strength is proportional to the number of nucleotides incorporated. The signals are then analyzed and correlated to determine the sequence.

In some instances, the enriched nucleic acids will be identified using mass spectrometry. Mass spectrometry uses a combination of electric and/or magnetic fields to cause nucleic acid ions (or pieces of) to follow specific trajectories (or to have specific flight times) depending on their individual mass (m) and charge (z). In addition, by arranging collisions of a parent molecular ion with other particles (e.g. argon atoms), the molecular ion may be fragmented forming secondary ions by the so-called collision induced dissociation (CID). The fragmentation pattern/pathway very often allows the derivation of detailed structural information. The structural information may be used to determine the sequence of the nucleic acid. Nucleic acids are difficult to volatilize, however. Using techniques such as electrospray/ionspray (ES) and matrix-assisted laser desorption/ionization (MALDI), nucleic acids can be volatilized, ionized, and characterized by their mass-to-charge profile. Additionally, DNA massarrays, such as offered by Sequenom (San Diego, Calif.), can be used to facilitate MALDI mass spectrometric analysis by tagging complementary nucleic acids with easily-detected mass labels.

Control Systems

Any suitable control mechanism may be used to cause a driving field and a mobility-varying field to be applied in a coordinated manner to cause particles to move by SCODA. In some embodiments of the invention, the time-variation of the driving field and the mobility-varying field are derived directly from a common source such that their effects on the particles are correlated. In other embodiments of the invention the driving and mobility-varying fields are generated under the control of a controller such as a hard-wired controller, a programmable controller, a general purpose computer equipped with suitable interface electronics or the like. Any suitable control mechanism including those known to those skilled in the art of designing scientific equipment may be applied.

Electrophoretic Concentration of Particles by SCODA

Consider an electrically charged particle that has an electrophoretic mobility, μ in an electric field given by $\vec{E}=\cos(\omega t)E\hat{E}$ where $\hat{E}$ is a unit vector. By definition, the particle will move with a velocity given by:

$$\vec{v} = \mu \cos(\omega t) E_0 \hat{E} \quad (9)$$

From Equation (9), $\vec{v}$ has a time average of zero. If μ varies as a function of time and the Fourier transform of μ has a component proportional to $\cos(\omega t)$ then the time average of v(t) may not be zero. As a simple example, consider the case where:

$$\mu(t) = \mu_0 + \mu_1 \cos(\omega t) \quad (10)$$

In this case, the time average of v(t) is:

$$\vec{v} = \frac{1}{2}\mu_1 E_0 \hat{E} \quad (11)$$

This demonstrates the basic principle that there can be a non-zero electrophoretic drift even if the time average of the applied electric field is zero.

Now consider the case where the mobility of a particle is a function of electric field strength. While virtually any nonlinearity can be employed, consider the case where a particle's velocity is parallel to the direction of a driving electric field and the particle's speed is given by:

$$v = kE^2 \quad (12)$$

where k is a constant and E is the magnitude of the electric field. In this case, the particle's speed is proportional to the square of the magnitude of the electric field. The effective mobility of the particle (i.e. the relationship between small changes in drift velocity, $d\vec{v}$, and small changes in the electric field, $d\vec{E}$) varies with the magnitude of the applied electric field.

In Cartesian coordinates:

$$dv_x = \frac{\partial v_x}{\partial E_x}dE_x + \frac{\partial v_x}{\partial E_y}dE_y \text{ and } dv_y = \frac{\partial v_y}{\partial E_x}dE_x + \frac{\partial v_y}{\partial E_y}dE_y$$

Where the particle speed varies with the electric field as in Equation (12), Equation (13) reduces to:

$$dv_x = k\left[\left(E + \frac{E_x^2}{E}\right)dE_x + \left(\frac{E_x E_y}{E}\right)dE_y\right], \quad (14)$$

and $$dv_y = k\left[\left(\frac{E_x E_y}{E}\right)dE_x + \left(E + \frac{E_y^2}{E}\right)dE_y\right] \quad (15)$$

To help interpret this, consider the case where $E_y=0$ such that $E_x=E$. In this case Equations (14) and (15) become:

$$dv_x = 2kEdE_x \text{ and } dv_y = kEdE_y \quad (16)$$

From Equation (16) one can see that the influence on the particle velocity of perturbations of the electric field has a magnitude proportional to that of the ambient field. A perturbation having the same direction as the electric field has twice the influence on the particle velocity as a perturbation perpendicular to the electric field.

This can be exploited to provide an applied electric field that causes particles to be concentrated. Consider a plane wherein an applied electric field has a constant magnitude, E, and the electric field rotates in direction at an angular frequency ω so that the components of the electric field in x and y directions are given by:

$$E_x = E\cos(\omega t) \text{ and } E_y = \sin(\omega t) \quad (17)$$

Substituting the values from Equation (17) into Equations (14) and (15) yields a result which is the sum of constant terms, sine and cosine terms having an angular frequency ω, and sine and cosine terms having an angular frequency 2ω. A frame of reference can be selected such that only the cosine terms having an angular frequency of 2ω contribute to net particle drift. Evaluating only these terms yields:

$$dv_x = \frac{kE}{2}[\cos(2\omega t)]dE_x, \quad (18)$$

$$dv_y = \frac{kE}{2}[\cos(2\omega t)]dE_y$$

If a perturbing electric field having the form of a quadrupole field that varies with a frequency 2ω is added to the basic electric field specified by Equation (17) then a net drift of particles can be caused. For a perturbing electric field given by:

$$dE_x = -dE_q x \cos(2\omega t) \text{ and } dE_y = dE_q y \cos(2\omega t) \quad (19)$$

it can be shown that:

$$\overline{d\vec{v}} = \frac{kEdE_q}{4}\vec{r} \quad (20)$$

Equation (20) shows that for charged particles at all positions $\vec{r}$ there is a time-averaged drift toward the origin with a speed proportional to k, the coefficient that specifies the field-dependence of the mobility, E, the strength of the rotating field, and dEq, the strength of the perturbing quadrupole field.

Figure 2:
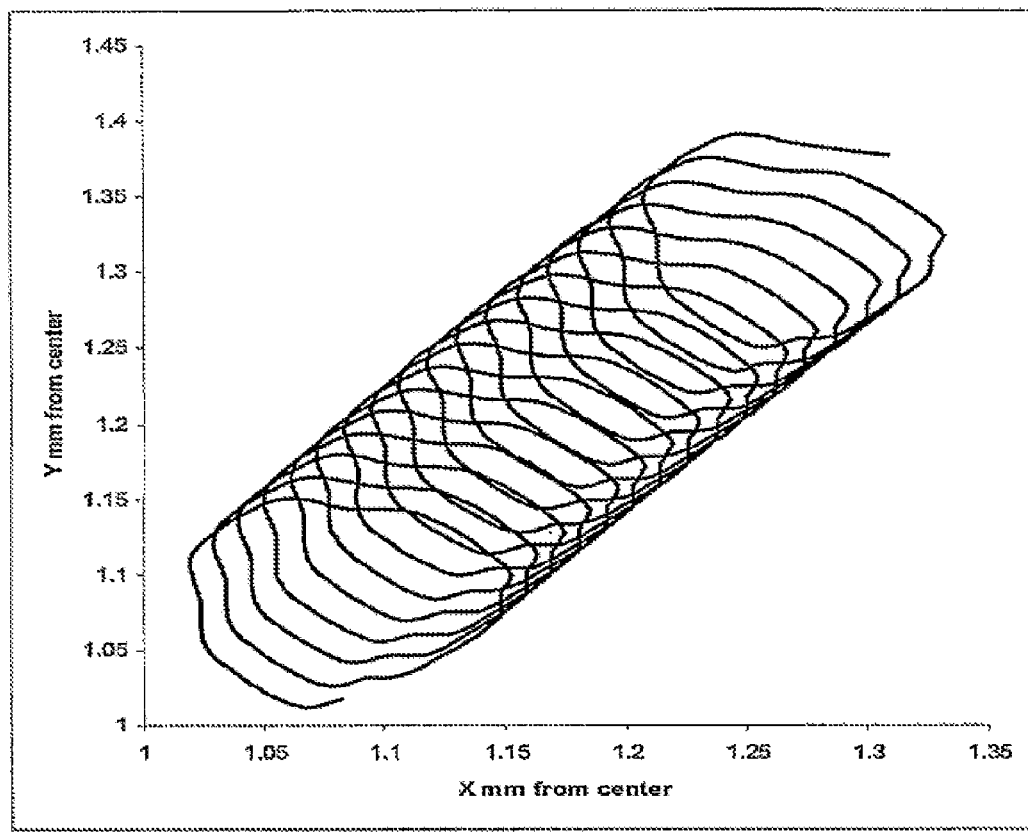
FIG. 2 is a plot showing a numerical simulation of the path of a particle exposed to a time-varying driving field and a time-varying mobility varying field.

The above calculation is for a case where the perturbing quadrupole field has a magnitude that is small in comparison to the rotating field. This is not necessary in general. FIG. 2 shows the result of a numerical simulation of the path of a particle in a case where the rotating electric field and quadrupole electric field are similar in magnitude. Motion begins at the top right hand side of FIG. 2 and progresses toward the bottom left over a period of 200 seconds. The applied electric fields are as described in Table I below. Each loop in the spiral path corresponds to a cycle of 12 voltage patterns each applied for 1 second. The uniform field amplitude is 3845 V/m at the origin (center of the electrode pattern). At the same location, the magnitude of the quadrupole component of the electric field is 4.2×105 V/m² or about 4200 V/m at a location 1 mm from the origin.

In many situations it is advantageous to concentrate particles in regions that are free of electrodes. Electrochemical processes at electrodes can cause damage to DNA and other sensitive materials. An electrical field that provides a particle focusing effect, as described above, can be provided without the need for electrodes at the location in which the particles become concentrated.

One can estimate the size of the spot into which particles can be concentrated from the Einstein-Smoluchowsky equation for diffusion with drift. A characteristic length scale, R, for the radius of a concentrated spot is given by:

$$R \propto \sqrt{\frac{D}{\mu_s}} \quad (21)$$

where D is the diffusion coefficient for the particles and $\mu_s$ is given by $kEE_q/4$.

Figure 3A:
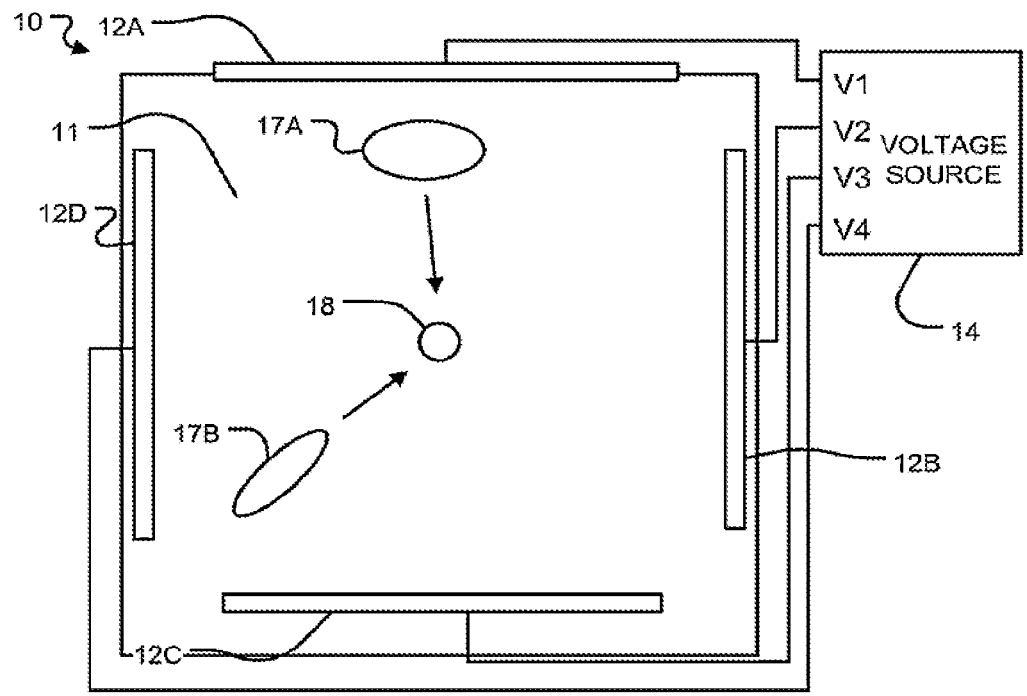
FIG. 3A is a schematic diagram of an apparatus that may be used to practice embodiments of the invention.

FIG. 3A shows apparatus 10 having a simple arrangement that can be used to practice the invention. A layer 11 of a medium, which may be a gel, such as an agarose gel, is located between four symmetrically arranged electrodes 12A, 12B, 12C, and 12D (collectively electrodes 12). It has been found to be desirable to provide electrodes 12 in the form of mesh electrodes. A power supply 14 applies individually controllable electrical potentials V1, V2, V3, and V4 to electrodes 12A through 12D respectively. Since it is the relative potentials of electrodes 12A through 12D that is significant, any one of electrodes 12A to 12D may be held at a convenient fixed voltage, such as 0 volts, while the voltages applied to the other electrodes are varied, if desired.

Figure 3B:
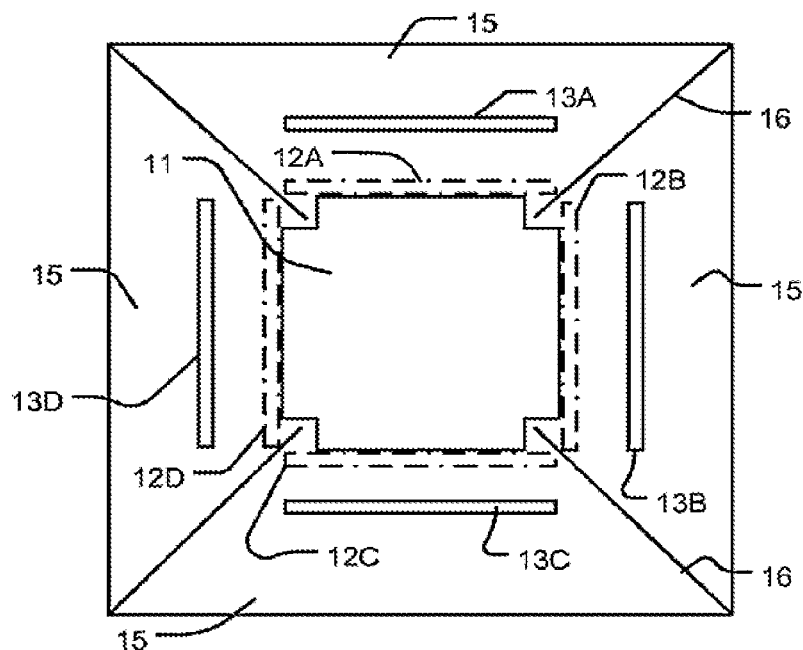
FIG. 3B is a schematic diagram of an apparatus that may be used to practice embodiments of the invention.

It is generally desirable to control the potentials applied to the electrodes to help stabilize the electric stimuli against small fluctuations due to changing temperature or changing power supply characteristics. Separate electrical potential sensing electrodes may be incorporated to provide feedback to a controller representing the actual electrical potential being applied. FIG. 3B is a schematic view of an apparatus comprising mesh electrodes 12A, 12B, 12C, and 12D and separate potential sensing electrodes 13A, 13B, 13C, and 13D (collectively electrodes 13). Large buffer reservoirs 15 maintain an ample supply of buffer against evaporation for long runs. Insulating barriers 16 separate adjacent reservoirs 15 electrically. Electrodes 13 are located in buffer reservoirs 15 and monitor the potential in the buffer. Feedback from electrodes 13 allows a suitably configured controller 14 to automatically adjust the voltages on mesh electrodes 12 to compensate for varying voltage drops across the mesh electrodes/buffer interface.

The magnitude of the applied voltage is chosen to match the size of the apparatus and the particles being separated. For DNA separations in agarose gels electric driving fields of approximately 50V/cm have been found to give satisfactory performance. The current supplied will depend upon the electrical conductivity and dimensions of the medium.

The application of the potentials causes electrically charged particles in medium 11 to move toward a central region 18. FIG. 3A shows groups 17A and 17B of particles moving toward concentration region 18. As noted above, the precise waveform according to which the applied electric fields vary is not critical to the operation of the invention. In a prototype embodiment of the invention, the potential variation of Equations (16) and (18) was approximated by a series of patterns of discrete voltages applied to electrodes 12A through 12D. In the prototype, each cycle was made up of 12 patterns that were each applied for 1 second before moving to the next pattern. Table 1 shows the voltages applied for each pattern.

TABLE 1

Applied voltages for scodaphoresis apparatus of FIG. 3A.

| | Voltage Patterns | | | |
|---|---|---|---|---|
| Pattern | Electrode 12A | Electrode 12B (V) | Electrode 12C (V) | Electrode 12D (V) |
| 1 | 0 | −66 | 0 | −198 |
| 2 | 132 | 132 | 0 | 0 |
| 3 | 132 | 198 | 0 | 198 |
| 4 | 132 | 198 | 0 | 198 |
| 5 | 132 | 0 | 0 | 132 |
| 6 | 0 | −198 | 0 | −66 |
| 7 | 0 | −198 | 0 | −66 |
| 8 | −132 | −132 | 0 | 0 |
| 9 | −132 | 66 | 0 | 66 |
| 10 | −132 | 66 | 0 | 66 |
| 11 | −132 | 0 | 0 | −132 |
| 12 | 0 | −66 | 0 | −198 |

Figure 3C:
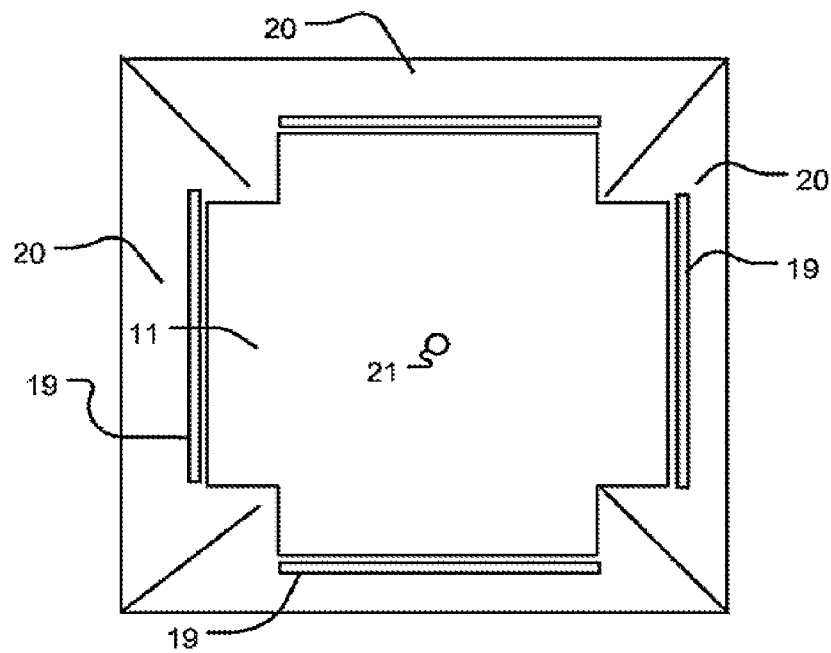
FIG. 3C is a schematic diagram of an apparatus that may be used to practice embodiments of the invention.

In the prototype embodiment of the invention illustrated schematically in FIG. 3C, medium 11 was in the form of a gel slab made up of 8-11 ml of 0.25% agarose gel (Agarose 2125 OmniPur available from EMD Chemicals of Gibbstown N.J., USA) forming a 3.8 cm square on an acrylic base in a 0.1× Tris-acetate-EDTA buffer. Four electrodes were submerged in the gel. Each electrode extended across one third of one side of the gel boat approximately 2.5 mm up from the bottom of the gel boat. DNA was prepared by mixing 8 µl of 500 µg/ml λ phage DNA (48,502 bp, part No. N3011L available from New England Biolabs of Beverly Mass., USA) with 12 µl 0.1×TAE. 5 µl spots of the DNA were pipetted directly onto the gel after the gel had set. A thin covering of TAE was placed on the gel. The voltage patterns of Table 1 were applied to the electrodes. It was found that the DNA spots were all carried to a central area of the gel.

For the DNA used in the prototype, D was measured experimentally to be $2 \times 10^{-12}$ m²/s. $\mu_s$ was measured to have a value of approximately $1 \times 10^{-3}$ 1/s. Using these values, the limiting spot size was calculated to be on the order of 100 µm. Spot radii on the order of 150 to 250 µm have been achieved in experiments.

In another experiment, a homogeneous solution of 400 ng/ml λ DNA in 1% agarose gel (0.01×TAE) was subjected to scodaphoresis. The gel was prepared by mixing 3 ml of 1% agarose gel with 1.5 µl of 500 ng/µl 48,502 bp λ DNA and 1.5 µg ethidium bromide (500 ng/ml final concentration). The gel was allowed to cool to approximately 65° C. and then poured into the gel boat. The gel was arranged in a cross shape, as shown in FIG. 3C. Platinum electrodes 19 0.03 mm in diameter were located in open electrode regions 20 of the apparatus. The electrode regions were free from gel and filled with 0.01×TAE buffer.

The distance between opposing electrodes was approximately 2.4 cm. After approximately 90 minutes, the λ DNA was found to have been concentrated in a region 21 in the center of the gel boat in a spot having a full width at half maximum of about 300 μm. The concentration of the λ DNA in the spot was enhanced by a factor of approximately 3000 to 4000 as compared to the initial concentration of λ DNA in the gel boat. The ability to cause DNA to be concentrated in an area 21 which is away from electrodes is advantageous in various applications.

The concentration factor, F, that can be achieved using a square gel slab having sides of length L is calculated to be approximately:

$$F = \frac{1}{\pi}\left(\frac{L}{200}\ \mu m\right)^2 \qquad (22)$$

Therefore, other factors being equal, increasing the dimensions of the gel slab can increase the concentration factor. For example, calculations suggest that a 35 cm×35 cm square gel slab could produce a concentration factor on the order of $10^6$. To achieve the best concentration it may be desirable to take steps to inhibit diffusion of particles out of the 2D surface in which SCODA is being used to concentrate the particles.

Electrophoretic SCODA in two dimensions can be performed conveniently using four electrodes arranged in two opposing pairs, as described above. Other arrangements of three or more electrodes that are not collinear with one another could also be used. For example SCODA could be performed using three electrodes arranged at corners of a triangle. SCODA could also be performed using five or more electrodes arranged around a region of a medium.

Since the passage of electrical current through a medium can lead to heating of the medium and most practical media are electrically conducting to some degree it is desirable to design SCODA apparatus to minimize heating, where practical, and to ameliorate the effects of heating, where necessary. For example, SCODA may be practiced in ways which include one or more of:
  cooling the medium through the use of a cooler in physical contact with the medium, cooling a buffer circulating around the medium, blowing cool air over the medium or evaporatively cooling the medium;
  making the medium very thin, thereby reducing the electrical current flowing in the medium and improving dissipation of heat from the medium;
  placing the medium on a thermally-conductive substrate that acts as a heat sink;
  reducing the electrical conductivity of the medium by way of a chemical treatment or by separating from the medium unneeded species that give rise to increased electrical conductivity;
  providing a reservoir of buffer and replenishing buffer surrounding the medium as the buffer evaporates (see, for example, FIG. 3B);
  providing one or more temperature sensors that monitor temperature of the medium and controlling the temperature of the medium to remain within an acceptable range by controlling the electrical current supplied to electrodes; and,
  using a driving field other than an electrical field.

3D SCODA

Figure 3D:
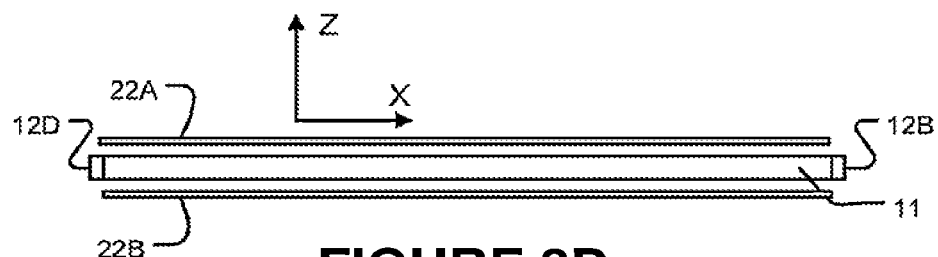
FIG. 3D is a schematic diagram of an apparatus that may be used to practice embodiments of the invention.

FIG. 3D shows apparatus similar to that of FIG. 3A that has been modified by the provision of additional Z electrodes 22A and 22B. Z electrodes 22A and 22B are each maintained at a DC voltage. For negatively charged particles, Z electrodes 22A and 22B are kept more negative in potential than the 2D SCODA electrodes 12A, 12B, 12C, and 12D. The provision of the Z electrodes provides a focusing force in the Z axis, and a de-focusing force in the XY plane of medium 11. The defocussing force is counteracted by SCODA.

Figure 3E:
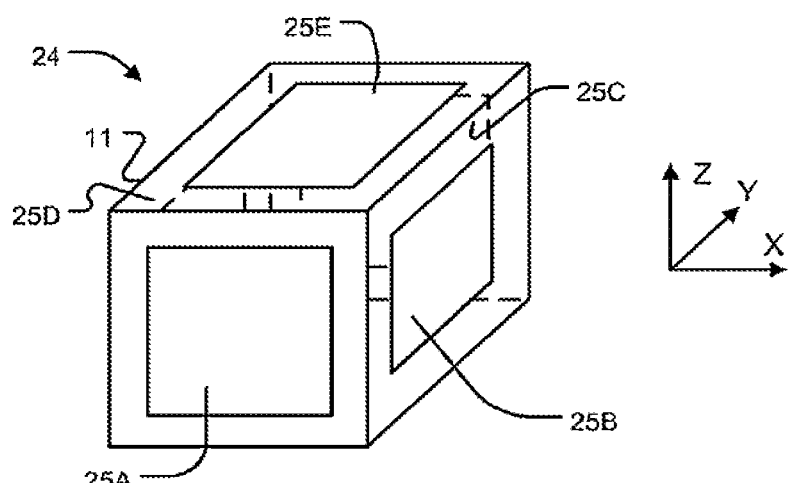
FIG. 3E is a schematic diagram of an apparatus that may be used to practice embodiments of the invention.

FIG. 3E shows apparatus 24 according to an embodiment of the invention that provides 3D concentration of particles in a cube-shaped block of medium 11 by alternately performing SCODA using electrodes in XY, XZ, and YZ planes. For example, electrodes 25A, 25B, 25C, and 25D are used for concentration in the XY plane. Electrodes 25A, 25E, 25C and another electrode (not visible in FIG. 3E) on the side of medium 11 opposed to electrode 25E are used for concentration in the YZ plane. Electrodes 25B, 25E, 25D and the electrode opposed to electrode 25E are used for concentration in the XZ plane.

Size Selection

If desired, SCODA processes can be made to select DNA and similar particles by size. This may be achieved by suitably adjusting the diffusion coefficient, D (D can be controlled by choice of medium), and the frequency of the driving field. Using higher driving field frequencies can cause larger particles to be less likely to be concentrated by SCODA. For example, in one experiment applying a driving field having a period of 12 seconds was found to concentrate both long λ DNA and shorter DNA fragments from a 1 kB ladder. It was found that reducing the period of the driving field to approximately 10 ms resulted in concentration of only the shorter DNA fragments but not the longer λ DNA fragments. While the inventors do not wish to be bound by any particular theory of operation, this size selection may be due to the 10 ms period being shorter than the relaxation time for the larger λ DNA fragments and longer than the relaxation time for the shorter DNA fragments.

In the same experiment it was found that SCODA (under these conditions) did not concentrate shorter DNA fragments (smaller than a few hundred bp). The selection out of the small sizes may be due to the smaller fragments having higher values for the diffusion coefficient D.

It is believed that SCODA provides a method for separating supercoiled plasmids from plasmids that are nicked or otherwise degraded.

Purification of DNA

Because SCODA can be made selective for different kinds of particles by choosing a suitable medium and/or combination of driving and mobility-varying fields, SCODA can be used to purify materials, such as DNA. SCODA can be applied to cause DNA (or optionally DNA having a particular size range) to concentrate at a spot or along a line while other materials are not concentrated at the spot or line.

For example, in initial experiments, λ DNA was concentrated from a mixture of λ DNA and bovine serum albumin (BSA). There was a 10:1 concentration ratio of BSA to λ DNA. The λ DNA was concentrated into a spot, as described above. The BSA was not concentrated in the spot.

In some embodiments of the invention, denaturing agents, protease, nuclease inhibitors and/or RNAase are added to a mixture of materials from which the particles are to be separated. Such agents may be provided to facilitate one or more of: reducing the binding of undesired molecules to fragments of DNA or other molecules that are desired to be concentrated; reducing the amount of RNA present, if so desired; preventing damage to DNA; and/or breaking down the undesired molecules into components that will not be concentrated by SCODA.

In some cases it may be desirable to use SCODA to separate particles of interest from a mixture which includes materials, such as salts, that cause the medium a high electrical conductivity. For example, bacterial cell cultures are often grown in media having salt contents on the order of up to 0.4M. In cases where it is desired to use electrophoretic SCODA to separate DNA directly from a cell culture, such as an *E. coli* culture, the high electrical conductivity will result in higher electrical currents in the medium. This in turn can lead to heating of the medium. This issue may be addressed by one or some combination of the heating control techniques discussed above.

SCODA with Selective Media

The mobility of a target nucleic acid in a media can be influenced by the presence of compounds that preferentially bind to the target nucleic acid. For example, a gel may be made to include DNA oligonucleotides that are complementary to the DNA in the particles that it is desired to concentrate. The complementary DNA oligonucleotides may be covalently bonded to the gel. In other embodiments, the compound may be a binding protein, e.g., an antibody or a specialty-binding protein, such as MutS, which binds to DNA mismatches.

If the characteristic time required for the particles to bind to the binding compounds is $t_{on}$ and the characteristic time required for the particles to dissociate from the binding compounds is $t_{off}$ then the average drift velocity for a particle in the medium is given by:

$$\overline{v} = \mu(E) * E \frac{t_{on}}{t_{on} + t_{off}} \quad (23)$$

where $\mu(E)$ is the field-dependent particle mobility due to reptation effects. Typically, $t_{off}$ is determined by an Arrhenius relationship while $t_{on}$ is determined by diffusive effects. By selecting particles to have lengths of 1000 or more nucleotides, reasonable values for $t_{off}$ of 1 second or less can be achieved with practical values of electric field (for example, electric fields in the range of 100 to 200 V/cm).

Electric Driving Field Combined with Thermal Mobility Varying Field

A demonstration of SCODA was carried out by thermally altering the drag coefficient of current-carrying solute ions in an electrolyte. When applying an AC potential across an electrolyte solution, and synchronously raising and lowering the temperature of the solution, a net transport of ions is expected. If the oscillation frequency of the AC potential differs from the frequency of the thermal oscillations, a detectable component of the ionic current should be present at the difference of the two frequencies, indicating alternating (AC) transport due to SCODA.

Separation of Differentially Modified Molecules

In some embodiments, molecules that are identical except for the presence or absence of a chemical modification that alters the binding of the molecule for a probe are separated using SCODA. Some embodiments of SCODA are sufficiently sensitive to separate two molecules that have only a small difference in binding for the immobilized agent. Examples of such molecules include differentially modified molecules, such as methylated and unmethylated nucleic acids, methylated or acetylated proteins, or the like.

For example, it has been previously shown that methylation of cytosine residues increases the binding energy of hybridization relative to unmethylated DNA sequences. RNA sequences would be expected to display a similar increase in the binding energy of hybridization when methylated as compared to unmethylated sequences. The inventors have shown that one embodiment of SCODA can be used to separate nucleic acid sequences differing only by the presence of a single methylated cytosine residue. Other chemical modifications would be expected to alter the binding energy of a nucleic acid and its complementary sequence in a similar manner. Modification of proteins, such as through methylation, can also alter the binding of a protein of interest with a protein, RNA or DNA aptamer, antibody, or other molecule that binds to the protein at or near the methylation site. Accordingly, embodiments of SCODA can be used to separate differentially modified molecules of interest. While the examples herein are directed to methylation enrichment, SCODA can also be applied to enrichment and selection of molecules with other chemical differences, including, e.g., acetylation.

SCODA, and sequence-specific SCODA, may be used to enrich a specific sequence of methylated DNA out of a background of methylated and unmethylated DNA. In this application of SCODA, the strength of the SCODA focusing force may be related to the binding energy of the target DNA to the bound oligonucleotides. Target molecules with a higher binding energy may be made to focus more strongly than targets with lower binding energy. Methylation of DNA has previously been documented to slightly increase the binding energy of target DNA to its complementary sequence. Small changes in binding energy of a complementary oligonucleotide may be exploited through SCODA to preferentially enrich for methylated DNA. SCODA operating conditions may be chosen, for example as described above, such that the methylated DNA is concentrated while unmethylated DNA of the same sequence is washed off the gel.

Some embodiments can separate molecules with a difference in binding energy to an immobilized agent of less than kT, the thermal excitation energy of the target molecules. Some embodiments can separate molecules with a difference in binding energy to an immobilized agent of less than 0.19 kcal/mol. Some embodiments can separate molecules with a difference in binding energy to an immobilized agent of less than 2.6 kcal/mol. Some embodiments can separate molecules with a difference in binding energy to an immobilized agent of less than 3.8 kcal/mol. Some embodiments can separate molecules that differ only by the presence of a methyl group. Some embodiments can separate nucleic acid sequences that differ in sequence at only one base.

Generation of a Time Varying Temperature Gradient

Embodiments of SCODA that use variations in temperature as the mobility altering field may use a periodically varying temperature gradient to produce a convergent velocity field. A periodically varying temperature gradient may be provided in any suitable manner, for example by the use of heaters or thermoelectric chillers to periodically heat and cool regions of the medium, the use of radiative heating to periodically heat regions of the medium, the application of light or radiation to periodically heat regions of the medium, Joule heating using the application of an electric field to the medium, or the like.

A periodically varying temperature gradient can be established in any suitable manner. For example, a temperature gradient may allow a particle increased mobility (i.e. at a higher temperature) when a driving field is applied toward the focus spot than when a driving field is applied away from the focus spot. In some embodiments, the temperature gradient is rotated to produce a convergent velocity field in conjunction with the application of a time-varying driving force.

In some embodiments, Joule heating using an electric field is used to provide a temperature gradient. In some embodiments, the electric field used to provide Joule heating to provide a temperature gradient is the same as the electric field that provides the driving field. In some embodiments, the magnitude of the electric field applied is selected to produce a desired temperature gradient within an matrix.

In some embodiments, a spatial temperature gradient is generated using a quadrupole electric field to provide the Joule heating. In some such embodiments, a two dimensional gel with four electrodes is provided. Voltages are applied to the four electrodes such that the electric field in the gel is non-uniform, containing regions of high electric field (and consequently high temperature) and low electric field. The electric field is oriented such that the regions of high electric field tend to push negatively charged molecules towards the center of the gel, while regions of low electric field tend to push such molecules away from the center of the gel. In some such embodiments, the electric field that provides the temperature gradient through Joule heating is also the electric field that applies a driving force to molecules in the gel.

Figure 4:
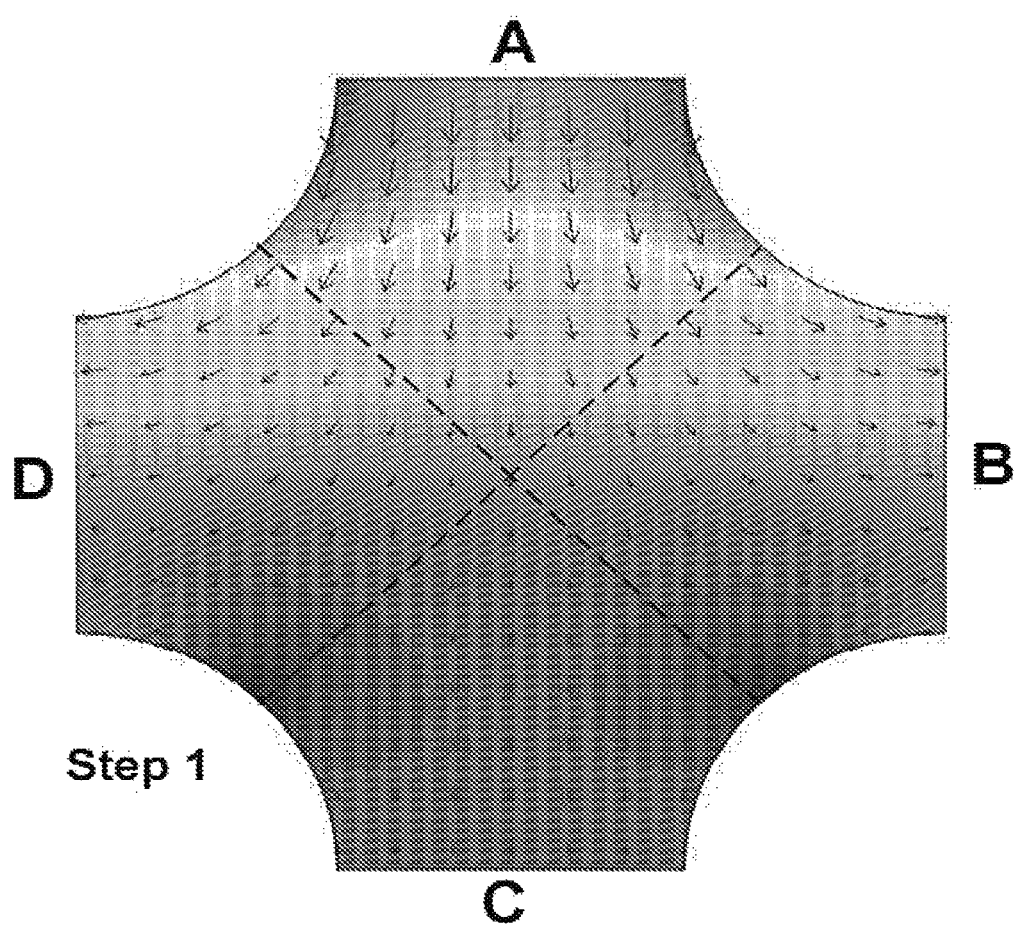
FIG. 4 shows an example of an electric field pattern suitable for two dimensional SCODA based concentration in some embodiments. Voltages applied at electrodes A, B, C, and D, are −V, 0, 0, and 0 respectively. Arrows represent the velocity of a negatively charged analyte molecule such as DNA. Color intensity represents electric field strength.

An example of such a field pattern is illustrated in FIG. 4. Voltages applied at electrodes A, B, C and D in FIG. 4 are −V, 0, 0, and 0 respectively. Arrows represent the velocity of a negatively charged analyte molecule. Color intensity represents electric field strength. The regions near electrode A have a high electric field strength, which decreases towards electrode C. The high field regions near electrode A tend to push negatively charged molecules towards the center of the gel, while the lower field regions near electrodes B, C, and D tend to push negatively charged molecules away from the center of the gel. In embodiments in which the electric field also provides the temperature gradient, the matrix will become hotter in regions of higher field strength due to Joule heating. Hence, regions of high electric field strength will coincide with regions of higher temperature and thus higher mobility. Accordingly, molecules in the high electric field regions near electrode A will tend to move a greater distance toward the center of the gel, while molecules in the lower electric field regions near electrodes B, C, and D have a lower mobility (arc at a cooler temperature) and will move only a short distance away from the center of the gel.

Figure 5:
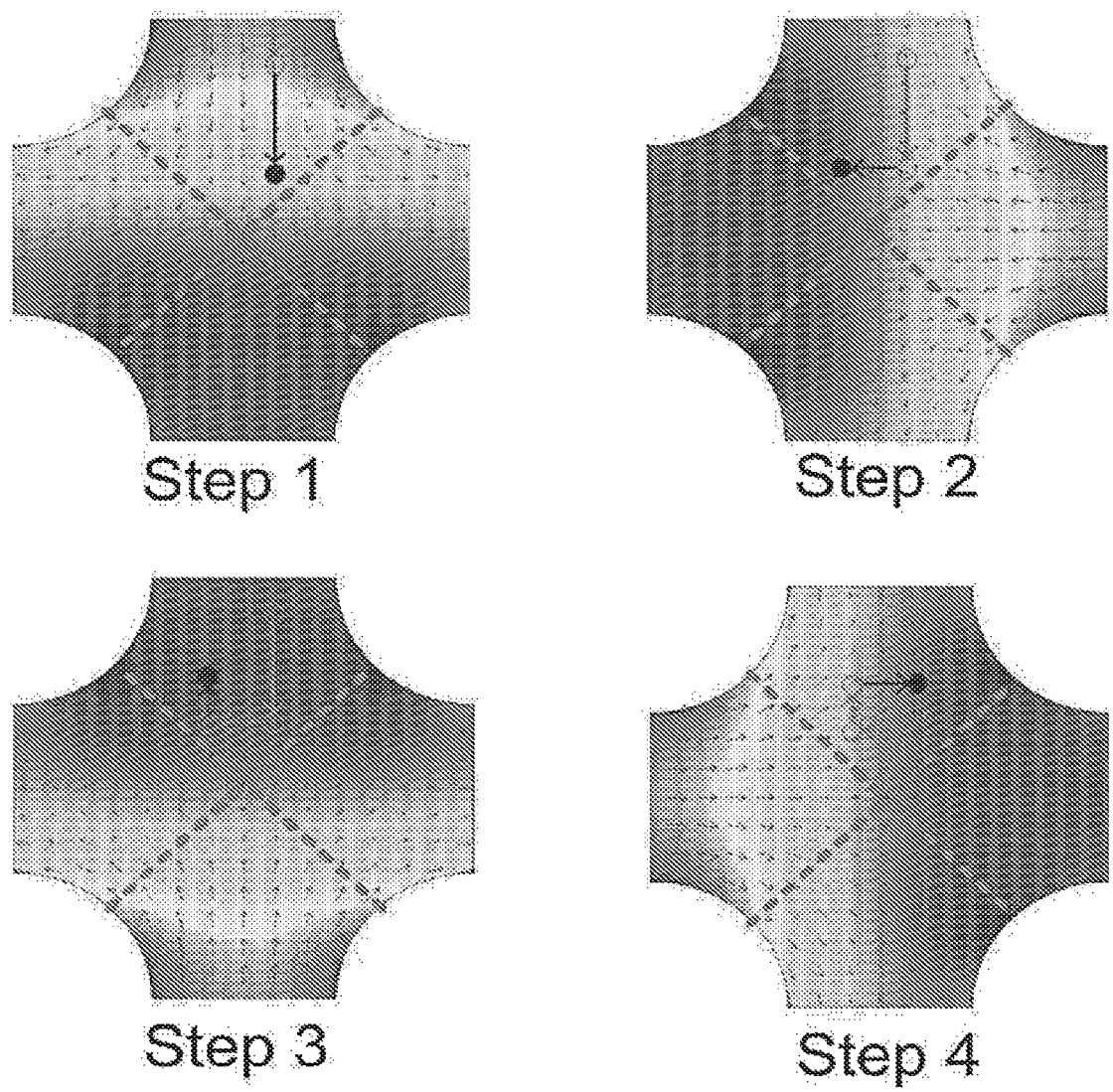
FIG. 5 shows stepwise rotation of the electric field leading to focusing of molecules whose mobility increases with temperature in one embodiment of SCODA. A particle path is shown by the arrows.

In some embodiments, the electric field pattern of FIG. 4 is rotated in a stepwise manner by rotating the voltage pattern around the four electrodes such that the time averaged electric field is zero as shown in FIG. 5. This rotating field will result in net migration towards the center of the gel for any molecule that is negatively charged and has a mobility that varies with temperature. In some embodiments, the electric field pattern is varied in a manner other than rotation, e.g. by sequentially shifting the voltage pattern by 180°, 90°, 180°, and 90°, or by randomly switching the direction of the electric field. As shown above, the mobility of a molecule moving through a matrix depends on temperature, not electric field strength. The applied electric field will tend to increase the temperature of the matrix through Joule heating; the magnitude of the temperature rise at any given point in the matrix will be proportional to the square of the magnitude of the electric field.

In embodiments in which the thermal gradient is provided by Joule heating produced by the electric field that also provides the driving field, the oscillations in the thermal gradient will have the same period as the electric field oscillations. These oscillations can drive SCODA based concentration in a two dimensional gel.

FIG. 5 illustrates the stepwise rotation of the electric field leading to focusing of molecules whose mobility increases with temperature or electric field according to such an embodiment. A particle path for a negatively charged molecule is shown. After four steps the particle has a net displacement toward the center of the gel. Molecules that do not experience a change in mobility with changing temperature or electric field will experience zero net motion in a zero time averaged electric field.

Theoretical Predictions of Focusing and Separation

In some embodiments, the electric field and subsequently the Joule heating within an SCODA gel are controlled by both the voltage applied to the source electrodes, and the shape of the gel. For example, superimposed rotating dipole and quadrupole fields can be used to drive electrophoretic SCODA concentration. The ratio of the strength of these two fields, the dipole to quadrupole ratio (DIQ), has an impact on the efficiency of SCODA focusing with a maximum at around DIQ=4.5, however the optimum is relatively flat with the SCODA force staying relatively constant for values between 1.75 and 10. One convenient choice of DIQ is 2. With this particular choice, only two distinct potentials need to be applied to the source electrodes, which can be achieved by connecting one electrode to a common voltage rail, grounding the other three, and rotating this pattern in a stepwise manner through the four possible configurations as shown in Table 2. Although analog amplifiers can be used and were used in the examples described herein, using a D/Q ratio of 2 allows one to use discrete MOSFET switches, which simplifies and reduces the required size and complexity of the power supplies.

TABLE 2

Voltage pattern for SCODA focusing with D/Q = 2.

| | Electrode A | Electrode B | Electrode C | Electrode D |
|---|---|---|---|---|
| Step 1 | −V | 0 | 0 | 0 |
| Step 2 | 0 | −V | 0 | 0 |
| Step 3 | 0 | 0 | −V | 0 |
| Step 4 | 0 | 0 | 0 | −V |

A starting point for a sequence specific gel geometry was the four-sided gel geometry used for the initial demonstration of electrophoretic SCODA. This geometry can be defined by two numbers, the gel width and the corner radius. The inventors started by using a geometry that had a width of 10 mm and a corner radius of 3 mm. An electro-thermal model of this geometry was implemented in COMSOL MULTIPHYSICS® modeling software (COMSOL, Inc, Burlington Mass., USA) to estimate the electric field and temperature profiles within the gel and establish whether or not those field and temperature profiles could drive concentration of a target with a temperature dependent mobility. The model used simultaneously solves Ohm's Law and the heat equation within the domain, using the power density calculated from the solution of Ohm's Law as the source term for the heat equation and using the temperature solution from the heat equation to determine the temperature dependent electrical conductivity of the electrolyte in the gel.

Figure 6:
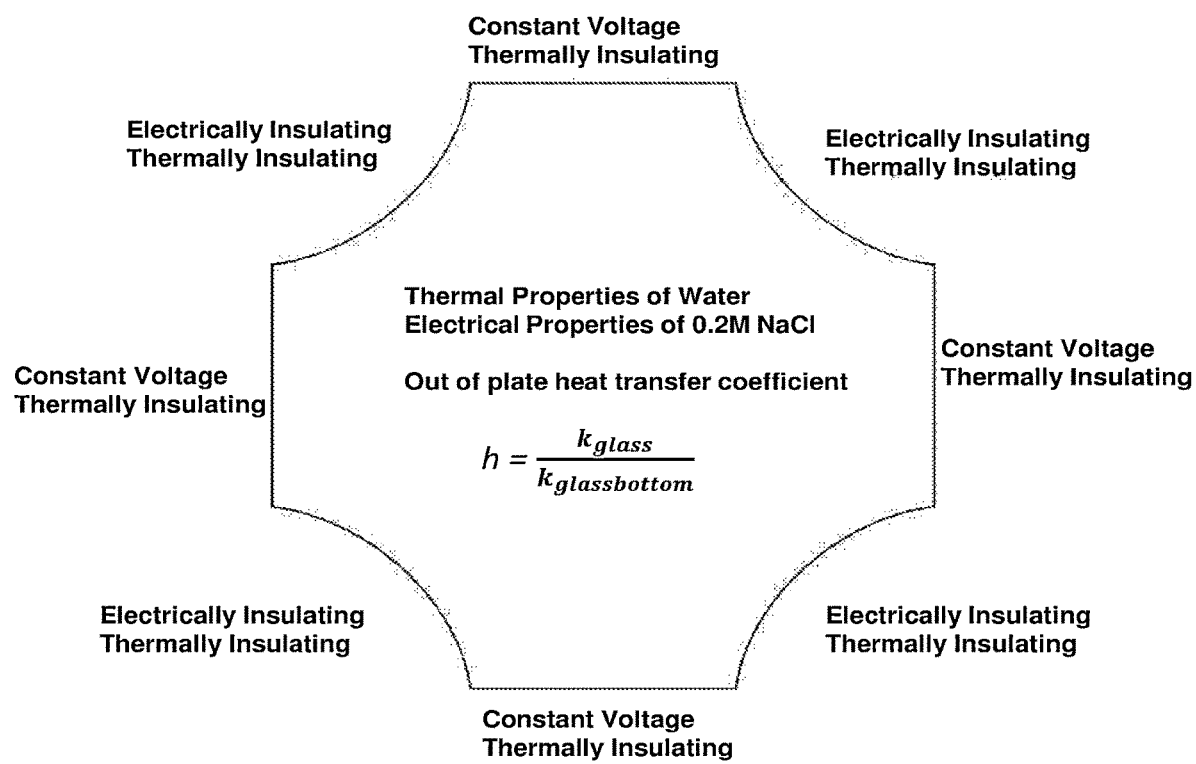
FIG. 6 shows the gel geometry including boundary conditions and bulk gel properties used for electrothermal modeling.
Figure 7:
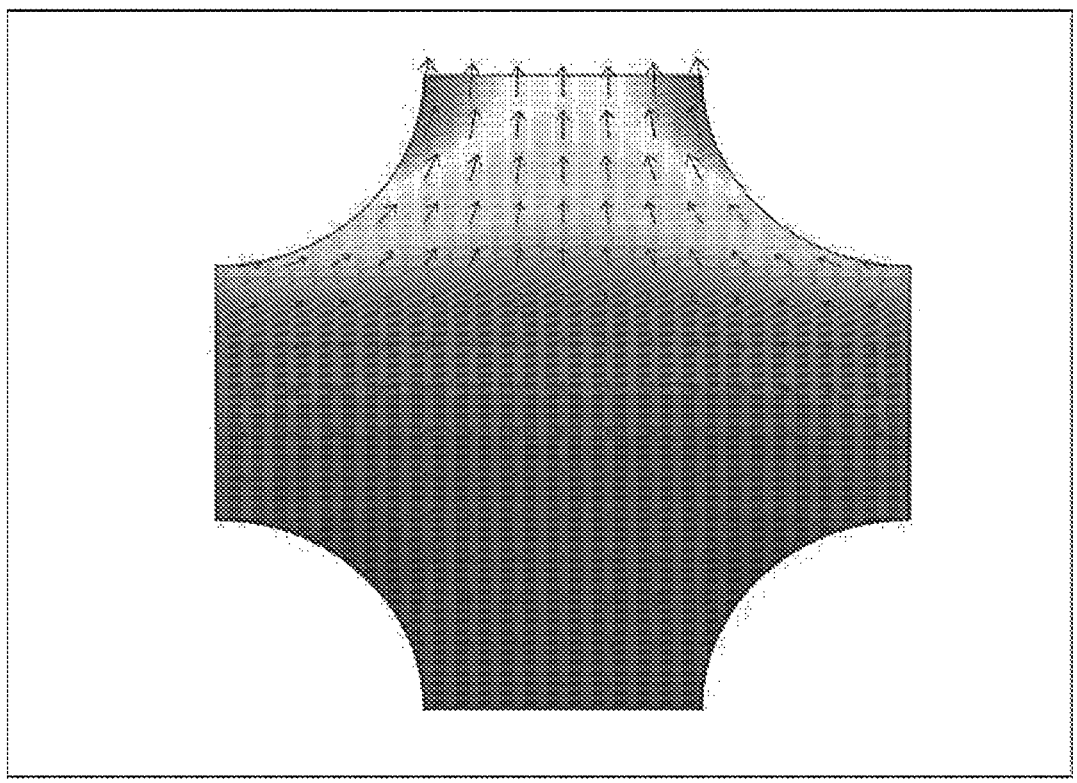
FIG. 7 shows the results of an electrothermal model for a single step of the SCODA cycle in one embodiment. Voltage applied to the four electrodes was −120 V, 0 V, 0 V, 0 V. Spreader plate temperature was set to 55° C. (328 K)
Figure 8:
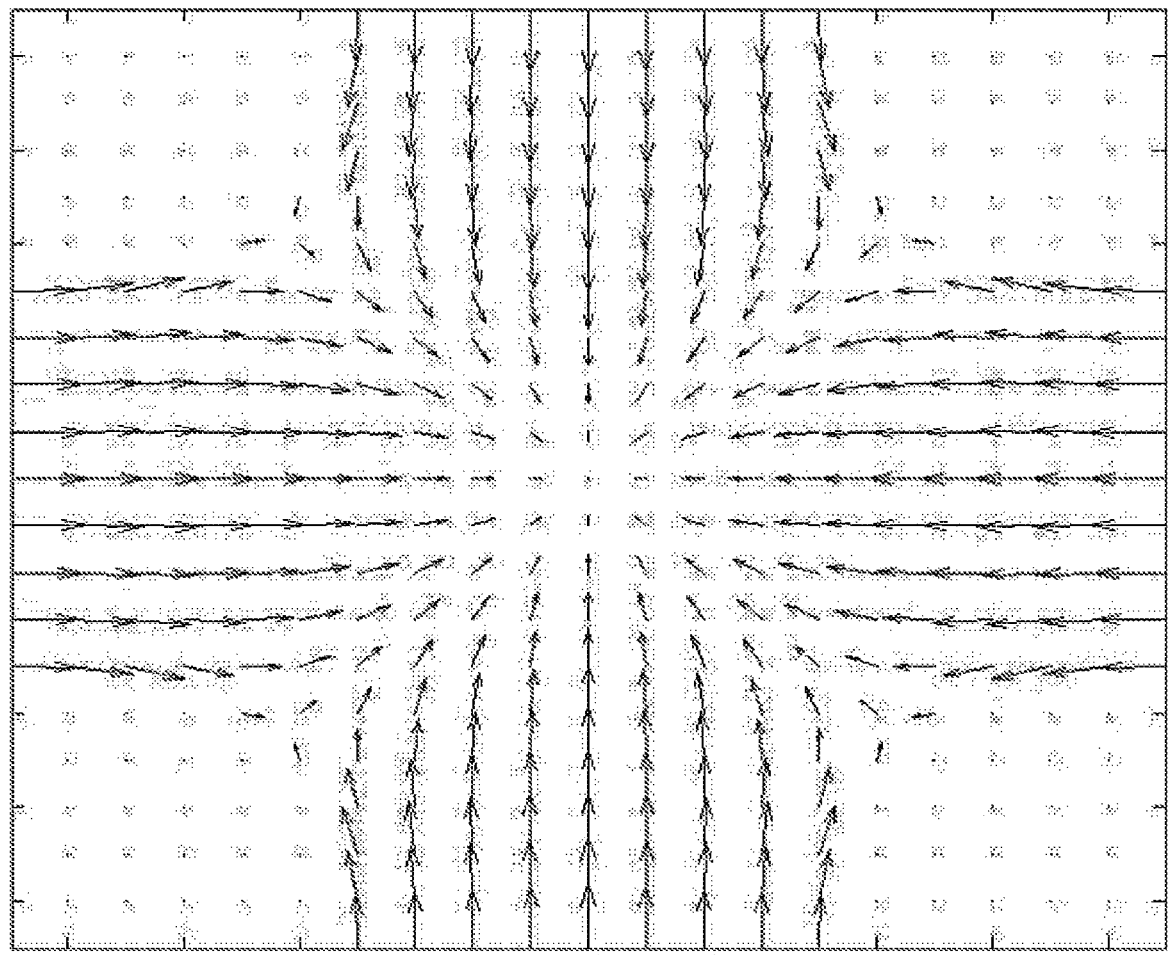
FIG. 8 shows SCODA velocity vector plots in one exemplary embodiment of the invention.

To obtain an accurate estimate of the temperature profile within the gel, the heat conducted out of the top and bottom of the gel are modeled. Boundary conditions and other model parameters are illustrated in FIG. 6. The thermal properties of water and electrical properties of 0.2 M NaCl were used. The gel cassettes are placed on an aluminum spreader plate that acts as a constant temperature reservoir. To model heat flow into the spreader plate the heat transfer coefficient of the glass bottom, given by k/t, was used. The temperature and electric field profiles solved by this model for a single step of the SCODA cycle are shown in FIG. 7. The voltage applied to the four electrodes was −120 V, 0 V, 0 V, 0 V, and the spreader plate temperature was set to 55° C. (328 K). The color map indicates gel temperature and the vector field shows the relative magnitude and direction of the electric field within the gel. Note that as DNA is negatively charged its migration direction will be opposite to the direction of the electric field. FIG. 8 shows that the aggregate vectors for the model of FIG. 6 is toward the center of the medium for the target nucleic acid over several cycles.

Using experimentally determined values of mobility versus temperature for a given molecule and the thermal model described above, it is possible to determine the SCODA velocity everywhere in the gel for that particular molecule by taking the time average of the instantaneous drift velocity integrated over one complete cycle:

$$\vec{v}_s = \frac{1}{\tau} \int_0^\tau \mu(T(\vec{r}, t))\vec{E}(\vec{r}, t)dt \quad (24)$$

where μ is the temperature dependent mobility, E the electric field and τ the period of the SCODA cycle. The temperature and electric field were solved for four steps in the SCODA cycle and coupled with the mobility function. In this manner, the SCODA velocity everywhere in the gel can be calculated. Since discrete steps are being used, if it is assumed that the period is long enough that the phase lag between the electric field and temperature can be neglected, then the integral in equation (24) becomes a sum:

$$\vec{v}_s = \frac{\sum \mu(T_i(\vec{r}))\vec{E}_i(\vec{r})t_i}{\sum t_i} \quad (25)$$

where the velocity is summed over all four steps in the cycle.

Heteroduplex-Binding Proteins

The invention includes the use of a heteroduplex-binding protein to alter the mobility characteristics ⌊μ⌋ of heteroduplex nucleic acids as compared to homoduplex nucleic acids of nearly identical length and/or sequence, as a function of an applied mobility altering field. While the invention is generally described as including the heteroduplex binding proteins in the medium, it is also possible to mix the heteroduplex binding proteins with a mixture of hetero- and homoduplexed nucleic acids before the nucleic acids are added to a medium not comprising heteroduplex binding protein. In other embodiments, the heteroduplex-binding proteins may be incorporated into the medium and added to the mixture of homo- and heteroduplexed nucleic acid before the mixture is loaded onto the separation medium.

Heteroduplex-binding proteins may be any of a number of proteins that include a heteroduplex binding domain, such as MutS, which is part of the Mismatch Repair System (MMRS) that has evolved to repair errors that occur during replication. The MMRS system includes MutS, in addition to MutH, which opens the bound heteroduplex nucleic acid, and MutL, which coordinates the function of MutS and MutH. Together these proteins work in concert to identify and remove mistaken bases, extra bases, or missed bases.

Figure 9:
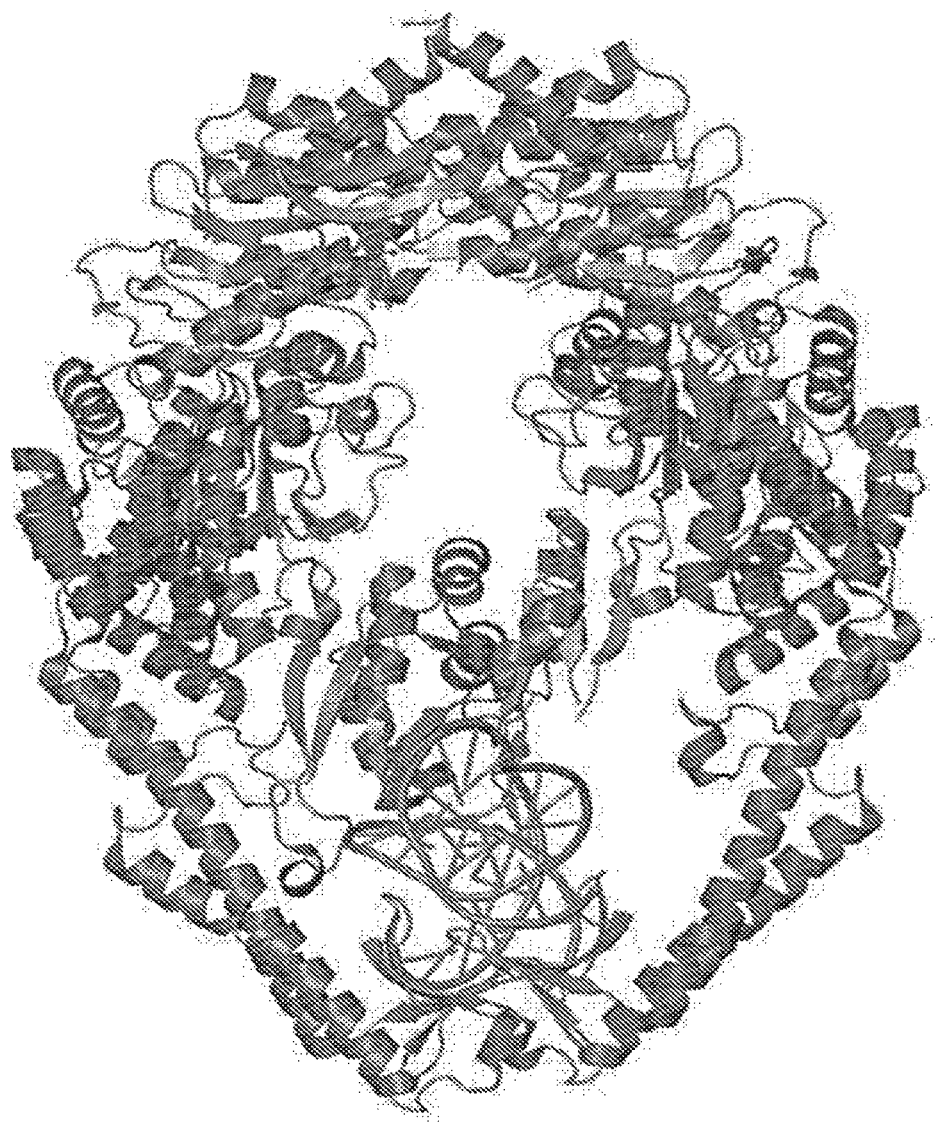
FIG. 9 shows a ribbon model of E. coli MutS protein hound to a mismatched DNA (six o'clock position of figure)

MutS proteins, or homologues thereof, are found in many species, including eukaryotes, archaea, and bacteria A ribbon structure of MutS from *E. coli* is shown in FIG. 9, including a bound heteroduplex nucleic acid at the 6 o'clock position. The nucleic acid is bound by a combination of hydrogen bonds and salt bridges. The residues responsible for binding directly with the mismatched bases are well-characterized in MutS from *E. coli*. See Lamers, et al. "The crystal structure of DNA mismatch repair protein MutS binding to a G×T mismatch," *Nature*, vol. 407(6805), pages 711-7 (2000), incorporated by reference herein in its entirety. While the heteroduplex binding domain of the MutS protein is similar between species, the overall length of the protein varies as demonstrated by Tables 3-5, which present the amino acid sequences for Mut S protein in *E. coli*, humans, and *Thermos thermophilus* respectively. The invention is not limited solely to known MutS proteins, however, as other proteins with heteroduplex binding domains, or mutations of wild-type MutS proteins may be used with the invention. MutS protein, suitable for use with the invention, is commercially-available from suppliers such as Promega Corporation (Madison, Wis.). Other sources of MutS protein, as well as engineered MutS protein and/or recombinantly-produced MutS protein are available from specialty producers, such as OriGene Technologies, Inc. (Rockville, Md.) or Nippon Gene (Yoyama, Japan). In some embodiments of the invention, the heteroduplexed nucleic acids are separated with the use of a heteroduplex binding protein having at least 85% sequence identify with SEQ ID NOS. 1, 2, or 3, e.g., at least 90% sequence identify with SEQ ID NOS. 1, 2, or 3, e.g., at least 95% sequence identify with SEQ ID NOS. 1, 2, or 3, e.g., at least 98% sequence identify with SEQ ID NOS. 1, 2, or 3, e.g., at least 99% sequence identify with SEQ ID NOS. 1, 2, or 3.

TABLE 3

Amino Acid Sequence of *E. coli* MutS protein.

SEQ ID NO. 1: MSTPENFDAH TPMMQQYLKL KAQHPEILLF

YRMGDFYELF YDDAKRASQL LDISLTKRGA SAGEPIPMAG

IPYHAVENYL AKLVNQGESV AICEQIGDPA TSKGPVERKV

VRIVTPGTIS DEALLQERQD NLLAAIWQDS KGFGYATLDI

SSGRFRLSEP ADRETMAAEL QRTNPAELLY AEDFAEMSLI

EGRRGLRRRP LWEFEIDTAR QQLNLQFGTR DLVGFGVENA

PRGLCAAGCL LQYAKDTQRT TLPHIRSITM ERQQDSIIMD

AATRRNLEIT QNLAGGAENT LASVLDCTVT PMGSRMLKRW

LHMPVRDTRV LLERQQTIGA LQDFTAELQP VLRQVGDLER

ILARLALRTA RPRDLARMRH AFQQLPELRA QLENVDSAPV

QALREKMGEF AELRDLLERA IIDTPPVLVR DGGVIASGYN

EELDEWRALA DGATDYLERL EVRERERTGL DTLKVGFNAV

HGYYIQISRG QSHLAPINYM RRQTLKNAER YIIPELKEYE

DKVLTSKGKA LALEKQLYEE LFDLLLPHLE ALQQSASALA

ELDVLVNLAE RAYTLNYTCP TFIDKPGIRI TEGRHPVVEQ

VLNEPFIANP LNLSPQRRML IITGPNMGGK STYMRQTALI

TABLE 3-continued

Amino Acid Sequence of E. coli MutS protein.

ALMAYIGSYV PAQKVEIGPI DRIFTRVGAA DDLASGRSTF

MVEMTETANI LHNATEYSLV LMDEIGRGTS TYDGLSLAWA

CAENLANKIK ALTLFATHYF ELTQLPEKME GVANVHLDAL

EHGDTIAFMH SVQDGAASKS YGLAVAALAG VPKEVIKRAR

QKLRELESIS PNAAATQVDG TQMSLLSVPE ETSPAVEALE

NLDPDSLTPR QALEWIYRLK SLV

TABLE 4

Amino Acid Sequence of recombinant human MutS protein.

SEQ ID NO. 2: MSRQSTLYSF FPKSPALSDA NKASARASRE

GGRAAAAPEA SPSPGGDAAW SEAGPGPRPL ARSASPPKAK

NLNGGLRRSV APAAPTSCDF SPGDLVWAKM EGYPWWPCLV

YNHPFDGTFI REKGKSVRVH VQFFDDSPTR GWVSKRLLKP

YTGSKSKEAQ KGGHFYSAKP EILRAMQRAD EALNKDKIKR

LELAVCDEPS EPEEEEMEV GTTYVTDKSE EDNEIESEEE

VQPKTQGSRR SSRQIKKRRV ISDSESDIGG SDVEFKPDTK

EEGSSDEISS GVGDSESEGL NSPVKVARKR KRMVTGNGSL

KRKSSRKETP SATKQATSIS SETKNTLRAF SAPQNSESQA

HVSGGGDDSS RPTVWYHETL EWLKEEKRRD EHRRRPDHPD

FDASTLYVPE DFLNSCTPGM RKWWQIKSQN FDLVICYKVG

KFYELYHMDA LIGVSELGLV FMKGNWAHSG FPEIAFGRYS

DSLVQKGYKV ARVEQTETPE MMEARCRKMA HISKYDRVVR

REICRIITKG TQTYSVLEGD PSENYSKYLL SLKEKEEDSS

GHTRAYGVCF VDTSLGKFFI GQFSDDRHCS RFRTLVAHYP

PVQVLFEKGN LSKETKTILK SSLSCSLQEG LIPGSQFWDA

SKTLRTLLEE EYFREKLSDG IGVMLPQVLK GMTSESDSIG

LTPGEKSELA LSALGGCVFY LKKCLIDQEL LSMANFEEYI

PLDSDTVSTT RSGAIFTKAY QRMVLDAVTL NNLEIFLNGT

NGSTEGTLLE RVDTCHTPFG KRLLKQWLCA PLCNHYAIND

RLDAIEDLMV VPDKISEVVE LLKKLPDLER LLSKIHNVGS

PLKSQNHPDS RAIMYEETTY SKKKIIDFLS ALEGFKVMCK

IIGIMEEVAD GFKSKILKQV ISLQTKNPEG RFPDLTVELN

RWDTAFDHEK ARKTGLITPK AGFDSDYDQA LADIRENEQS

LLEYLEKQRN RIGCRTIVYW GIGRNRYQLE IPENFTTRNL

PEEYELKSTK KGCKRYWTKT IEKKLANLIN AEERRDVSLK

DCMRRLFYNF DKNYKDWQSA VECIAVLDVL LCLANYSRGG

DGPMCRPVIL LPEDTPPFLE LKGSRHPCIT KTFFGDDFIP

NDILIGCEEE EQENGKAYCV LVTGPNMGGK STLMRQAGLL

TABLE 4-continued

Amino Acid Sequence of recombinant human MutS protein.

AVMAQMGCYV PAEVCRLTPI DRVFTRLGAS DRIMSGESTF

FVELSETASI LMHATAHSLV LVDELGRGTA TFDGTAIANA

VVKELAETIK CRTLFSTHYH SLVEDYSQNV AVRLGHMACM

VENECEDPSQ ETITFLYKFI KGACPKSYGF NAARLANLPE

EVIQKGHRKA REFEKMNQSL RLFREVCLAS ERSTVDAEAV

HKLLTLIKEL

TABLE 5

Amino Acid Sequence of Thermus thermophilus MutS protein.

SEQ ID NO. 3 MGGYGGVKME GMLKGEGPGP LPPLLQQYVE

LRDRYPDYLL LFQVGDFYEC FGEDAERLAR ALGLVLTHKT

SKDFTTPMAG IPIRAFDAYA ERLLKMGFRL AVADQVEPAE

EAEGLVRREV TQLLTPGTLT QEALLPREAN YLAAIATGDG

WGLAFLDVST GEFKGTLLKS KSALYDELFR HRPAEVLLAP

ELRENEAFVA EFRKRFPVML SEAPFEPQGE GPLALRRAQG

ALLAYARATQ GGALSVRPFR LYDPGAFVRL PEASLKALEV

FEPLRGQDTL FGVLDETRTA PGRRLLQAWL RHPLLERGPL

EARLDRVERF VREGALREGV RRLLFRLADL ERLATRLELS

RASPRDLAAL RRSLEILPEL KGLLGEEVGL PDLSGLLEEL

RAALVEDPPL KVSEGGLIRE GYDPDLDALR RAHAEGVAYF

LDLEAREKER TGIPTLKVGY NAVFGYYLEV TRPYYEKVPQ

EYRPVQTLKD RQRYTLPEMK ERERELYRLE ALIKRREEEV

FLALRERARK EAEALREAAR ILAELDVYAA LAEVAVRHGY

TRPRFGERLR IRAGRHPVVE RRTAFVPNDL EMAHELVLVT

GPNMAGKSTF LRQTALIALL AQIGSFVPAE EAELPLFDGI

YTRIGASDDL AGGKSTFMVE MEEVALVLKE ATERSLVLLD

EVGRGTSSLD GVAIATALAE ALHERRCYTL FATHYFELTA

LALPRLKNLH VAAKEEEGGL VFYHQVLPGP ASKSYGVEVA

EMAGLPKEVV ERARALLSAM AARREGALEE VLERLLALDP

DRLTPLEALR FLHELKALAL GLPLGSMKG

SCODA Field Sequences

FIG. 10 provides exemplary SCODA field sequences that can be used to separate nucleic acids complexed with a heteroduplex-binding protein. In this embodiment, the combination of time varying mobility-varying fields and time varying driving fields causes the nucleic acids to repeatedly bind to a heteroduplex binding protein only during a low temperature portion of the mobility varying field, where their mobility is reduced. Nucleic acids such as homoduplexes that do not have substantial repeated interactions with a heteroduplex binding protein move to a region of the separation medium where they can be washed away. In some embodiments, the washing force is a DC electric field, described herein as a DC bias. For target molecules, the SCODA focusing force applied by the SCODA focusing fields described above will tend to counteract movement of a molecule caused by the washing field, i.e. the SCODA focusing fields will tend to exert a restoring force on the molecules and the molecules will be preferentially focused as compared with duplexed nucleic acids not bound to a heteroduplex binding protein and having a different mobility. With repeated cycles, complexes of heteroduplexed nucleic acids and heteroduplex binding proteins will become concentrated in an extraction region where they can be recovered. Additionally, a benefit of repeated binding and unbinding of DNA to heteroduplex binding protein increases the specificity of the assay, since for a molecule to focus it must undergo many binding and unbinding events. Thus, it is much less likely that a homoduplex molecule is focused than were it to be separated with only a single lower specificity binding event.

In one exemplary embodiment used to separate nucleic acids having similar sequences, a DC bias is superimposed over the voltage pattern shown in Table 2, resulting in the voltage pattern shown below in Table 6. In some embodiments, the DC bias is applied alternately with the SCODA focusing fields, i.e. the SCODA focusing fields are applied for a period of time then stopped, and the DC bias is applied for a period of time then stopped.

TABLE 6

Applied voltages for focusing under a DC bias. Shown are values for a 120 V SCODA focusing potential superimposed over a 10 V DC bias.

|        | Electrode A | Electrode B | Electrode C | Electrode D |
|--------|-------------|-------------|-------------|-------------|
| Step 1 | −120        | 5           | 10          | 5           |
| Step 2 | 0           | −115        | 10          | 5           |
| Step 3 | 0           | 5           | −110        | 5           |
| Step 4 | 0           | 5           | 10          | −115        |

In some embodiments, the optimal combination of the driving field and the mobility altering field used to perform SCODA focusing where there is a maximum difference in focusing force between similar molecules is empirically determined by measuring the velocity of sample molecules through a medium as a function of the mobility varying field. For example, in some embodiments the mobility of a desired target molecule and a non-desired target molecule at various temperatures is measured in a matrix as described above, and the temperature range at which the difference in relative mobility is greatest is selected as the temperature range for conducting SCODA. In some embodiments, the focusing force is proportional to the rate at which the velocity changes with respect to the perturbing field dv/df, where v is the molecule velocity and f the field strength. One skilled in the art may maximize dv/df so as to maximize SCODA focusing and to enable fast washing of contaminants that do not focus. To maximally separate two similar molecules, SCODA may be carried out under conditions such that $dv_a/df - dv_b/df$ (where $v_a$ is the velocity of molecule a, and $v_b$ is the velocity of molecule b) is maximized.

In some embodiments, the strength of the electric field applied to a matrix is calculated so that the highest temperature within the gel corresponds approximately to the temperature at which the difference in binding between two molecules to be separated is highest.

In some embodiments, the temperature at which the difference in binding between the two molecules to be separated is highest corresponds to the temperature at which the difference between the melting temperature of a target molecule and the agent and the melting temperature of a non-target molecule and the agent is highest. In some embodiments, the maximum difference between the melting temperature of a target molecule and the agent and the melting temperature of a non-target molecule and the agent is less than about 9.3° C., in some embodiments less than about 7.8° C., in some embodiments less than about 5.2° C., and in some embodiments less than about 0.7° C.

In some embodiments, the ratio of target molecules to non-target molecules that can be separated by SCODA is any ratio from 1:1 to 1:10,000 and any value there between, e.g. 1:100 or 1:1,000. In some embodiments, after conducting SCODA, the ratio of non-target molecules relative to target molecules that is located in a focus spot of the target molecules has been reduced by a factor of up to 10,000 fold.

While the method can be performed on sample that has received little preparative clean up, in many cases, the final results will be improved if the starting sample comprises nucleic acids that are closely related and of similar size. As discussed previously, many applications will benefit from selective amplification of targeted sequence regions and subsequent denaturing and reannealing of the amplicons to create a population of homoduplexed and heteroduplexed nucleic acids. Various methods for preparing a sample for amplification are known. In most instances, the amplification, e.g., PCR, will be limited to reduce introduced errors, e.g., as discussed previously. For example, the a sample may be pre-amplified with 25 or less cycles of PCR, e.g., 20 or less cycles of PCR, e.g., 15 or less cycles of PCR, e.g., 10 or less cycles of PCR, e.g., 5 or less cycles of PCR. Even using small amounts of PCR, the described methods allow isolation of heteroduplexes having strands corresponding to mutation rates of less than 1% compared to the wild-type, e.g., less than 0.5% compared to the wild type, e.g., less than 0.1% compared to the wild type, e.g., less than 0.05% compared to the wild type, e.g., less than 0.01% compared to the wild type.

In some instances, other modifications, e.g., differential methylation or acetylation of nucleic acids will result in morphological differences that can be distinguished with the methods described above. For example, binding proteins can be engineered to be sensitive to various states of methylation in a nucleic acid sequence. Systems and methods for separating, purifying, concentrating and/or detecting differentially modified molecules as described above can be applied in fields where detection of biomarkers, specific nucleotide sequences or differentially modified molecules is important, e.g. epigenetics, fetal DNA detection, pathogen detection, cancer screening and monitoring, detection of organ failure, detection of various disease states, and the like. For example, in some embodiments SCODA is used to separate, purify, concentrate and/or detect differentially methylated DNA in such fields as fetal diagnostic tests utilizing maternal body fluids, pathogen detection in body fluids, and biomarker detection in body fluids for detecting cancer, organ failure, or other disease states and for monitoring the progression or treatment of such conditions.

In some embodiments, a sample of bodily fluid or a tissue sample is obtained from a subject. Cells may be lysed, genomic DNA is sheared, and the sample subjected to SCODA. Methods such as immunoprecipitation (pull-down assay) can be used to selectively isolate particular genes or loci of interest, for example BRCA1 prior to separation with the invention. In some embodiments, nucleic acids separated with the invention are subjected to further analysis, e.g. DNA sequencing, digital PCR, fluorescence detection, or the like, to assay for the presence of a particular biomarker or nucleotide sequence. In some embodiments, the subject is a human.

It is known that fetal DNA is present in maternal plasma, and that differential methylation of maternal versus fetal DNA obtained from the maternal plasma can be used to screen for genetic disorders (see e.g. Poon et al., 2002, *Clinical Chemistry* 48:1, 35-41). However, one problem that is difficult to overcome is discrimination between fetal and maternal DNA. SCODA as described above may be used to preferentially separate, purify, concentrate and/or detect DNA which is differentially methylated in fetal DNA versus maternal DNA. For example, SCODA may be used to concentrate or detect DNA which is methylated in the fetal DNA, but not in maternal DNA, or which is methylated in maternal DNA but not fetal DNA. In some embodiments, a sample of maternal plasma is obtained from a subject and subjected to SCODA using an oligonucleotide probe directed to a sequence of interest. The detection of two foci after the application of SCODA focusing fields may indicate the presence of DNA which is differentially methylated as between the subject and the fetus. Comparison to a reference sample from a subject that exhibits a particular genetic disorder may be used to determine if the fetus may be at risk of having the genetic disorder. Further analysis of the sample of DNA obtained through differential modification SCODA through conventional methods such as PCR, DNA sequencing, digital PCR, fluorescence detection, or the like, may be used to assess the risk that the fetus may have a genetic disorder.

One embodiment of the present systems and methods is used to detect abnormalities in fetal DNA, including chromosome copy number abnormalities. Regions of different chromosomes that are known to be differentially methylated in fetal DNA as opposed to maternal DNA are concentrated using SCODA to separate fetal DNA from maternal DNA based on the differential methylation of the fetal DNA in a maternal plasma sample. Further analysis of the separated fetal DNA is conducted (for example using qPCR, DNA sequencing, fluorescent detection, or other suitable method) to count the number of copies from each chromosome and determine copy number abnormalities.

Most cancers are a result of a combination of genetic changes and epigenetic changes, such as changes in DNA methylation (e.g. hypomethylation and/or hypermethylation of certain regions, see e.g. Ehrich, 2002, *Oncogene* 21:35, 5400-5413). SCODA can be used to separate, purify, concentrate and/or detect DNA sequences of interest to screen for oncogenes which are abnormally methylated. Embodiments of SCODA are used in the detection of biomarkers involving DNA having a different methylation pattern in cancerous or pre-cancerous cells than in healthy cells. Detection of such biomarkers may be useful in both early cancer screening, and in the monitoring of cancer development or treatment progress. In some embodiments, a sample obtained from a subject, e.g. a sample of a bodily fluid such as plasma or a biopsy, may be processed and analyzed by differential modification SCODA using oligonucleotide probes directed to a sequence of interest. The presence of two foci during the application of SCODA fields may indicate the presence of differential methylation at the DNA sequence of interest. Comparison of the sample obtained from the subject with a reference sample (e.g. a sample from a healthy patient and/or a sample known to originate from cancerous or pre-cancerous tissue) can indicate whether the cells of the subject are at risk of being cancerous or pre-cancerous. Further analysis of the sample of DNA obtained through differential modification SCODA through conventional methods such as PCR, DNA sequencing, digital PCR, fluorescence detection, or the like, may be used to assess the risk that the sample includes cells that may be cancerous or pre-cancerous, to assess the progression of a cancer, or to assess the effectiveness of treatment.

In some embodiments, biomolecules in blood related to disease states or infection are selectively concentrated using SCODA. In some embodiments, the biomolecules are unique nucleic acids with sequence or chemical differences that render them useful biomarkers of disease states or infection. Following such concentration, the biomarkers can be detected using PCR, sequencing, or similar means. In some embodiments, a sample of bodily fluid or tissue is obtained from a subject, cells are lysed, genomic DNA is sheared, and SCODA is performed using oligonucleotide probes that are complementary to a sequence of interest. SCODA is used to detect the presence of differentially methylated populations of the nucleic acid sequence of interest. The presence of differentially methylated populations of the target sequence of interest may indicate a likelihood that the subject suffers from a particular disease state or an infection.

In some embodiments, the focusing pattern of the target nucleic acid produced by SCODA from a subject is compared with the focusing pattern of the target nucleic acid produced by SCODA from one or more reference samples (e.g. an equivalent sample obtained from a healthy subject, and/or an equivalent sample obtained from a subject known to be suffering from a particular disease). Similarities between the focusing pattern produced by the sample obtained from the subject and a reference sample obtained from a subject known to be suffering from a particular disease indicate a likelihood that the subject is suffering from the same disease. Differences between the focusing pattern produced from the sample obtained from the subject and a reference sample obtained from a healthy subject indicate a likelihood that the subject may be suffering from a disease. Differences in the focusing pattern produced from the sample obtained from the subject and a reference sample obtained from a healthy subject may indicate the presence of a differential modification or a mutation in the subject as compared with the healthy subject.

Apparatus for Performing SCODA

In some embodiments, SCODA is performed on an electrophoresis apparatus comprising a region for containing the matrix, buffer reservoirs, power supplies capable of delivering large enough voltages and currents to cause the desired effect, precise temperature control of the SCODA medium (which is a gel in some embodiments), and a two color fluorescence imaging system for the monitoring of two different molecules in the SCODA medium.

In an embodiment, the apparatus includes at least three electrodes circumferentially surrounding a central reservoir with a separation medium between at least one electrode and the central reservoir. Circumferentially implies that the electrodes are located around a periphery at a distance from the central reservoir. The electrodes need not be on a circular path, nor do the electrodes have to be individually curved in shape. The electrodes must be electrically separable, so that the electrodes can be individually indexed as described below. The electrodes do not have to fill an amount of the circumferential distance and the electrodes do not have to be of the same shape. Typically, the central reservoir will contain a buffer or an additional separation medium, making it possible to recover the targeted molecules, e.g. for amplification and/or sequencing. In one arrangement, the apparatus includes arms extending outward from the central reservoir, each arm being associated with an electrode.

Embodiments of the present invention can be used to concentrate charged target particles in a collection region while limiting or preventing movement of charged target particles out of the collection region, without the need to place an electrode in the collection region. A separation apparatus with n separation arms, wherein n is at least 3, is provided. All n separation arms are in electrical contact through the collection region. Voltages are applied through the separation arms such that the electric field strength differs between at least one of the separation arms and the remaining arms. The voltage configuration is varied to produce net motion of the charged target particles in a desired direction. Conditions of electric field strength and a variable mobility altering field (which can be the electric field strength in some embodiments) are selected to produce net motion of target particles in a desired direction (i.e. either toward or away from the collection region). Contaminating particles that are not electrically charged, or that have a mobility that does not vary significantly under the application of the mobility altering field, experience little or no net motion under the influence of the electric field. In some embodiments, conditions of electric field strength and mobility altering field are selected so that a contaminating particle that is structurally similar to the target particle (e.g. a methylated form of the target particle or a particle having the same sequence as the target particle with one point mutation) experiences net motion in a direction opposite to the net motion experienced by the target particle. Particles that reach the collection region experience a restoring force upon movement into any one of the separation arms that tends to return such particles to the collection region. Thus, target particles can be collected in the collection region, without the need to provide an electrode in the collection region.

Figure 11:
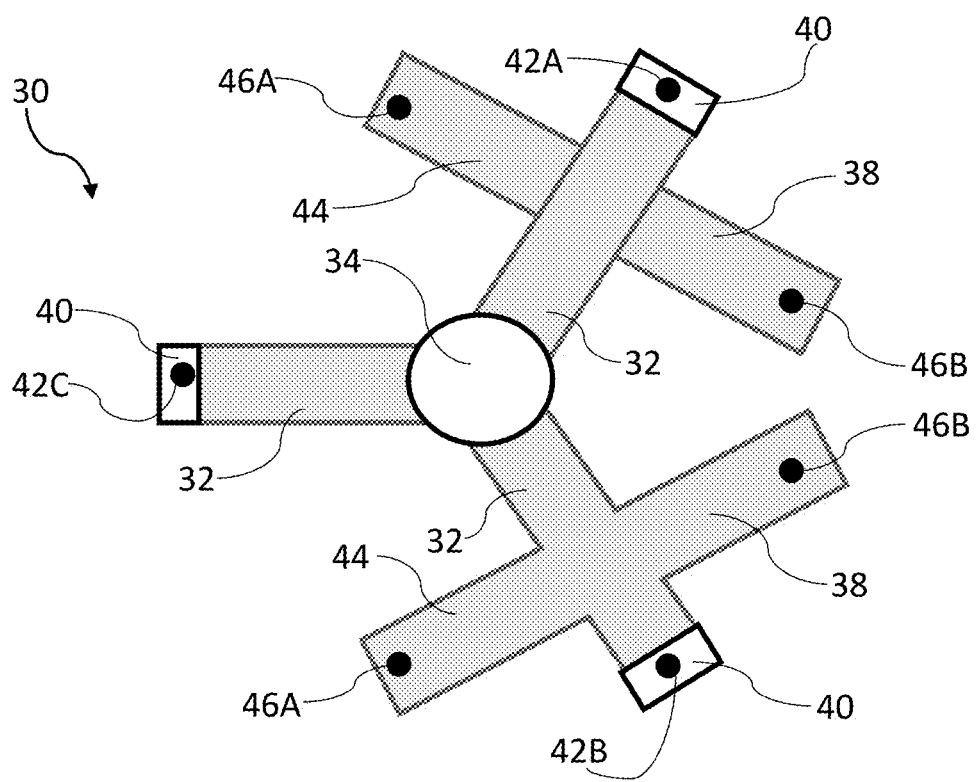
FIG. 11 shows an embodiment of an example apparatus according to one embodiment of the present invention.

FIG. 11 shows an apparatus 30 for separating particles according to one embodiment. Apparatus 30 has three separation arms 32 disposed around a central reservoir 34. In the illustrated embodiment, separation arms 32 are symmetrically disposed around central reservoir 34. Central reservoir 34 provides the collection region in the illustrated embodiment. Separation arms 32 are spaced apart; that is, the ends of separation arms 32 do not directly contact one another, but are separated by central reservoir 34. Each one of separation arms 32 includes separation medium (shown as 136 in FIG. 14B).

As used herein with reference to separation arms 32, the term "length" refers to a direction along separation arm extending between central reservoir 34 and the distal end of separation arm 32. "Width" refers to a direction perpendicular to and in the same plane as "length".

In some embodiments, central reservoir 34 optionally includes separation medium. Removal and extraction of collected target particles is facilitated in embodiments in which central reservoir 34 is filled with buffer.

A buffer chamber 40 is provided at the distal end of each separation arm 32 (i.e. the end opposite central reservoir 34) so that an electric field can be applied to each separation arm. Each buffer chamber 40 is provided with an electrode, shown schematically as 42A, 42B and 42C, so that an electric field can be applied to each separation arm 32.

Electrically charged target particles in a sample can be injected into a separation arm 32 by applying an electric field that drives the charged target particles into the separation arm. In some embodiments, injection of electrically charged target particles is done perpendicular to the direction that particles travel within separation arm 32, so that contaminating particles are not drawn to the central reservoir 34 during sample loading. Alternatively, target particles can be injected into separation arm 32 in any suitable manner, for example via the distal ends of separation arms 32, or vertically from a reservoir positioned above separation arms 32.

In the illustrated embodiment, at least one separation arm 32 is provided with a loading reservoir 38. Loading buffer chambers 44 are provided on the sides of separation arms 32 opposite loading reservoir 38. Loading electrodes, shown schematically as 46A, are provided in each loading buffer chamber 44. Complementary loading electrodes, shown schematically as 46B, are provided in each loading reservoir 38. In use, a sample is injected into one or more separation arms 32 by loading the sample in the appropriate loading reservoir(s) 38. A suitable potential difference is applied across opposing loading electrodes 46A, 46B to inject electrically charged components of the sample into separation medium 36 within separation arms 32. For example, where the target particles are nucleic acids, which are typically negatively charged, a positive voltage is applied to electrode 46A and a negative voltage is applied to electrode 46B to inject the nucleic acids into separation arm 32.

In some embodiments, a single loading reservoir is used to load the sample into multiple separation arms 32. In such embodiments, a single electrode 46B can be used in conjunction with several electrodes 46A to load the sample.

Electrically charged particles can be loaded in any suitable manner, including from above the separation arms and/or from the distal ends of the separation arms. In the illustrated embodiment, loading buffer chambers 44 are positioned towards the distal ends of separation arms 32 (i.e. the ends of separation arms 32 away from central reservoir 34). Loading buffer chambers 44 are configured to inject electrically charged particles perpendicularly into separation arms 32 so that the paths of travel of the charged particles entering a separation arms 32 extend across the width of the separation arm 32. Injection of electrically charged particles perpendicularly into separation arms 32 as in the illustrated embodiment minimizes the risk that non-target particles will reach central reservoir 34 during the injection process.

After the sample has been injected into separation arms 32, voltages are applied to electrodes 42A, 42B and 42C to produce an electric field and cause movement of particles within separation arms 32 (i.e. to provide a driving field). The direction of the driving field in a given separation arm 32 is varied from time to time. Concurrently with the application of the driving field, but not necessarily simultaneously, a mobility altering field is applied to vary the mobility of particles within separation arms 32. The effect of the mobility altering field is varied from time to time. In some embodiments, the electric field is both the driving field and the mobility altering field.

In some embodiments, including the illustrated embodiment, the electric field that provides the driving field also provides the mobility altering field. For example, for particles that have a mobility that varies with electric field strength, e.g. nucleic acids such as DNA or RNA, the applied electric field can provide both the driving field and the mobility altering field. For example, the following voltage patterns may be applied across electrodes 42A, 42B and 42C:

TABLE 7

Exemplary voltage pattern for embodiment with three separation arms.

| Step | Electrode 42A | Electrode 42B | Electrode 42C |
|------|---------------|---------------|---------------|
| 1 | H | H | L |
| 2 | L | H | H |
| 3 | H | L | H |

Where "H" represents a high voltage applied to the electrode, and "L" represents a low voltage applied to the electrode. At times when the voltage applied to an electrode associated with a particular separation arm 32 is high, the electric field strength in that particular separation arm 32 will be low. In the illustrated embodiment, the current flowing through separation arm 32C in step 1 will be twice the current flowing through either one of separation arms 32A or 32B in embodiments in which all separation arms have the same impedance (i.e. the amount of current flowing through separation arm 32C must equal the sum of the amount of current flowing through separation arms 32A and 32B). Thus, the electric field strength in separation arm 32C in this high electric field strength condition will be twice the electric field strength in either of separation arms 32A or 32B. Each of steps 1, 2 and 3 represents a discrete configuration of the driving field (the electric field) and the mobility altering field (the electric field) for this exemplary embodiment. The application of each of steps 1, 2 and 3 one time represents one cycle.

Figure 12:
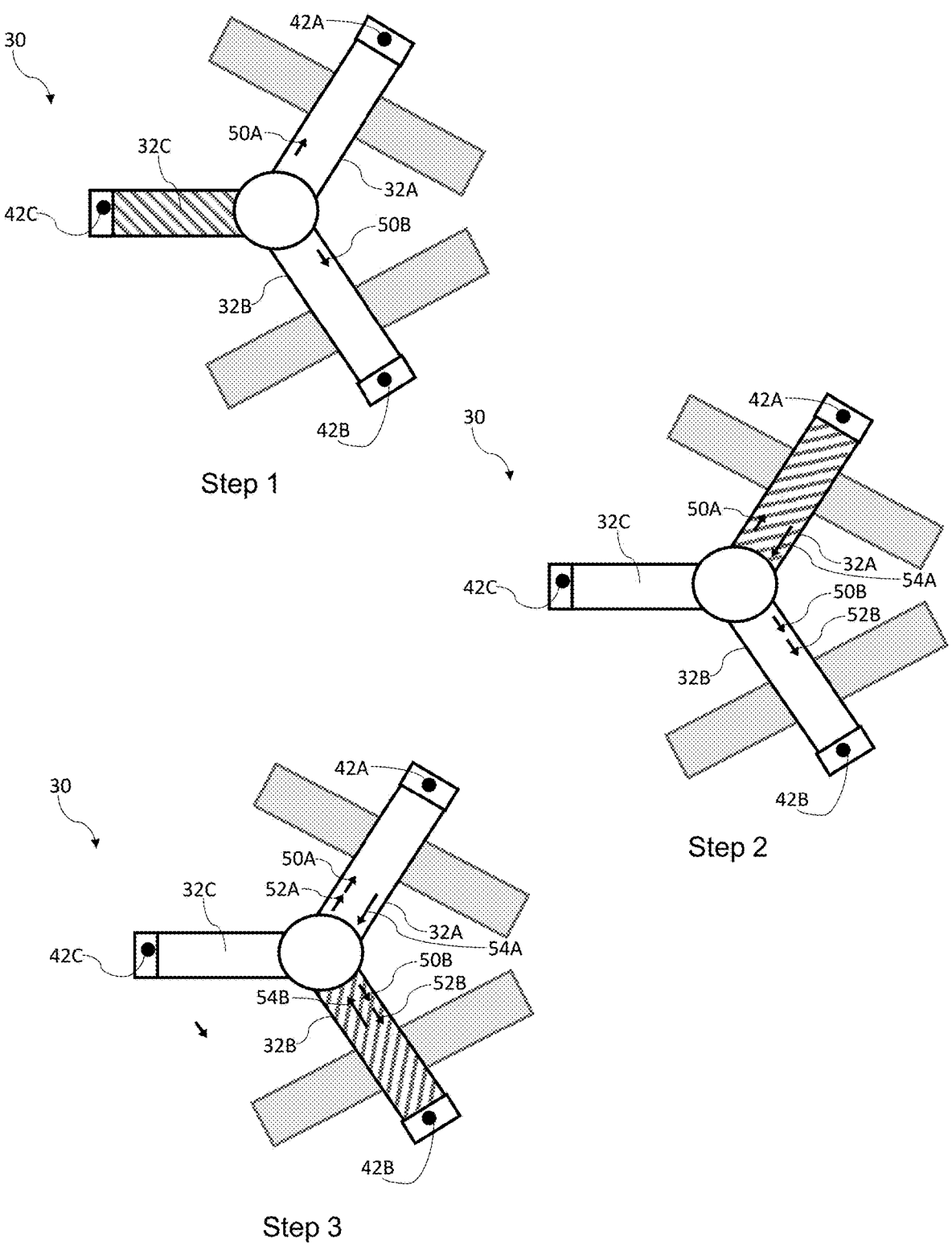
FIG. 12 shows the movement of a hypothetical particle under applied electric fields in an exemplary embodiment.

In some embodiments, the high voltage may be any voltage between 100 V and 1000 V, e.g. 100 V, 125 V, 150 V, 175 V, 200 V, 225 V, 250 V, 275 V, 300 V, 325 V, 350 V, 375 V, 400 V, 425 V, 450 V, 475 V, 500 V, 525 V, 550 V, 575 V, 600 V, 625 V, 650 V, 675 V, 700 V, 725 V, 750 V, 775 V, 800 V, 825 V, 850 V, 875 V, 900 V, 925 V, 950 V, 975 V, or 1000 V and the low voltage may be any voltage lower than the high voltage. The polarity of the voltage is selected depending on the charge of the target particles (positive or negative). The low voltage is 0 V in some embodiments. The effect of applying the voltages summarized in Table 7 on a negatively charged molecule from a sample that has a mobility that varies with electric field strength, for example a nucleic acid such as DNA or RNA, is illustrated schematically in FIG. 12 and described below with reference to the movement of an exemplary polynucleotide molecule. In step 1, separation arms 32A and 32B are regions of low electric field strength. Arm 32C is a region of high electric field strength, as indicated by diagonal shading. Negatively charged particles, such as polynucleotides, in separation arms 32A and 32B will move in a direction away from central reservoir 34 by a distance $\mu_L E_L t$, where $\mu_L$ is the mobility of the particle at the low electric field strength, $E_L$ is the low electric field strength, and t is the time for which the low electric field is applied. This movement is indicated schematically by arrows 50A, 50B. This motion will coincide with the time interval during the period of the cycle in which the electric field strength is low, and in which the mobility of the polynucleotides through separation medium 36 is lower (due to the relatively low electric field strength in separation arms 32A, 32B). Thus, the distance traveled by the polynucleotides located in separation arms 32A and 32B away from central reservoir 34 will be relatively small.

In step 2, separation arms 32B and 32C are regions of low field strength, as indicated by an absence of shading, while separation arm 32A is a region of high field strength, as indicated by diagonal shading. Negatively charged particles, such as polynucleotides, in separation arm 32B will again move in a direction away from central reservoir 34, as indicated by arrow 52B. This motion will coincide with the time interval during the period of the cycle in which the electric field strength is relatively low and in which the mobility of the polynucleotides through separation medium 36 is lower (due to the low electric field strength in separation arm 32B). Thus, the distance traveled by polynucleotides in separation arm 32B ($\mu_L E_L t$) away from central reservoir 34 will be relatively small. Negatively charged particles, such as polynucleotides, in separation arm 32A will move in a direction toward central reservoir 34, as indicated by arrow 54A. This motion will coincide with the time interval during the period of the cycle in which electric field strength is high and in which the mobility of the polynucleotides through separation medium 36 is higher (due to the high electric field strength in separation arm 32A). Thus, the distance traveled by the polynucleotides in separation arm 32A toward central reservoir 34 will be relatively large, and can be described as $\mu_H E_H t$, where $\mu_H$ is the mobility of the polynucleotide particle at the high electric field strength condition, $E_H$ is the high electric field strength, and t is the time for which the high electric field strength is applied.

In step 3, separation arms 32A and 32C are regions of low field strength, while separation arm 32B is a region of high field strength. Negatively charged 30 particles, such as polynucleotides, in separation arm 32A will move in a direction away from central reservoir 34, as indicated by arrow 52A. This motion will coincide with the time interval during the period of the cycle in which the electric field strength in separation arm 32 is low and in which the mobility of the polynucleotides through separation medium 36 is lower (due to the low electric field strength in separation arm 32A). Thus, the distance traveled by polynucleotides in separation arm 32A ($\mu_L E_L t$) in a direction away from central reservoir 34 will be relatively small. Negatively charged particles, such as polynucleotides, in separation arm 32B will move in a direction toward central reservoir 34, as indicated schematically by arrow 54B. This motion will coincide with the time interval during the period of the cycle in which the electric field strength is high and in which the mobility of the polynucleotides through separation medium 36 is higher (due to the high electric field strength in separation arm 32B). Thus, the distance traveled by the polynucleotides in separation arm 32B ($\mu_H E_H t$) toward central reservoir 34 will be relatively large.

In this example, negatively charged particles that do not have a mobility that varies with electric field strength, or that does not vary significantly with electric field strength (i.e. for which $\mu_L$ is equal or similar to $\mu_H$) will tend to experience zero net motion towards or away from central reservoir 34, because the times and electric field strengths have been selected such that the magnitude of the steps taken away from central reservoir 34 by such particles as represented, for example, by arrows 50A and 52A will tend to be equal or nearly equal to the magnitude of the steps taken towards central reservoir 34 by such particles, as represented, for example, by arrow 54A. That is, because the electric field strength at times of low electric field strength is ½ the electric field strength at times of high electric field strength, and because the particle experiences the low electric field strength for twice the length of time as the high electric field strength, the net motion of the particle will tend to be zero or close to zero.

Steps 1, 2 and 3 can be repeated to effect net motion of target particles that have a mobility that varies with electric field strength within separation arms 32. In some embodiments, operating conditions including the electric field strength and the length of time the electric field is applied are selected so that the motion of target particles toward central reservoir 34 during times of high electric field strength (illustrated as arrows 54A, 54B) is greater than twice as large as the total motion away from central reservoir 34 during times of low electric field strength during one cycle (illustrated as arrows 50A, 50B and 52A, 52B). That is, the average distance traveled by the target particles during all times of low electric field strength in one cycle is less than the average distance traveled by the target particles during times of high electric field strength in one cycle. In this manner, target particles can be concentrated in central reservoir 34 if the polarity of the applied voltage is selected appropriately. In the described exemplary embodiment, particles that have a mobility that varies with electric field strength (e.g. polynucleotides) can be separated from particles that have a mobility that does not vary with electric field strength, or which varies to a lesser extent with electric field strength (e.g. proteins).

It is not necessary that the electric field pattern be rotated as described above with respect to steps 1, 2 and 3. For example, the electric field pattern could be applied using random or occasionally varying combinations of the configuration of steps 1, 2 and 3. As long as the electric field pattern is such that the electric field in each separation arm containing target particles to be separated spends approximately ⅓ of the time in the high electric field strength configuration and approximately ⅔ of the time in a low electric field strength configuration, the net motion of the target particles will be towards central reservoir 34. Similarly, in an embodiment having n separation arms as described below, net motion of target particles towards central reservoir 34 can be effected in each one of the separation arms if the electric field pattern in that separation arm spends, on average, approximately 1/n of the time in the high electric field strength configuration and approximately (n−1)/n of the time in the low electric field strength configuration.

Apparatus 30 could be provided with any desired number n of separation arms 32, where n is greater than or equal to 3. For example, in some embodiments, apparatus 30 has 4, 5, 6, 7, 8, 9, 10, 11 or 12 separation arms 32. At least three separation arms are required so that the electric field strength can be varied as described above.

In embodiments where there are three or more separation arms and central reservoir 34 contains buffer, particles that enter central reservoir 34 will experience a net restoring force towards the separation arm that they came from (because the mobility of the particles will not vary within the buffer contained in central reservoir 34) and will tend to collect at the interface between the separation arm and central reservoir 34. The number of separation arms to be used in a particular embodiment would be determined by one skilled in the art depending on the nature of the particles to be separated using apparatus 30. The voltage patterns applied to such an apparatus would be similar. For example, Table 8 illustrates an exemplary voltage pattern that could be applied to an apparatus having six separation arms 32. In the exemplary embodiment, one separation arm is at a high electric field strength and the remaining (n−1) separation arms are at a low electric field strength in each cycle, similar to the embodiment described above.

TABLE 8

Exemplary voltage pattern for embodiment with six separation arms, each having one electrode, identified below as A, B, C, D, E or F.

| Step | Electrode | | | | | |
|------|---|---|---|---|---|---|
|      | A | B | C | D | E | F |
| 1 | H | H | L | H | H | H |
| 2 | H | H | H | L | H | H |
| 3 | H | H | H | H | L | H |
| 4 | H | H | H | H | H | L |
| 5 | L | H | H | H | H | H |
| 6 | H | L | H | H | H | H |

Providing a larger number of separation arms 32 can increase the significance of the electric field dependence of the net motion of particles within separation arms 32. That is, the magnitude of the difference between the electric field strength at the high electric field strength condition versus at the low electric field strength condition will be greater in embodiments having a larger number of separation arms 32. Particles that have a mobility in medium 36 that is highly dependent on electric field strength will tend to move a relatively larger amount in the direction of arrows 54A, 54B under conditions of higher field strength. Also, a greater number of steps in the direction of arrows 50A, 50B and 52A, 52B will be taken. Specifically, particles will take n−1 steps in the direction away from central reservoir 34, where n is the number of separation arms 32, for each step taken toward central reservoir 34.

In contrast, providing a smaller number of separation arms 32, e.g. three separation arms as shown in the illustrated embodiment, will decrease the significance of the electric field dependence of a particle's mobility on the net movement of that particle within separation arms 32. In some embodiments, for example those that exploit a binding interaction between the target particle and the medium assist in or effect separation, and/or those embodiments in which a field other than electric field strength (e.g. temperature, light, pH or salt concentration) is used as the mobility altering field, decreasing the significance of the electric field dependence of a particle's mobility on the net movement of that particle as aforesaid enhances separation of such target particles from other similar particles that share a similar electric field dependence of mobility (e.g. oligonucleotides of a similar length).

While the exemplary embodiments have been described above with reference to one separation arm having a high electric field strength while the remaining (n−1) separation arms have a low electric field strength, alternative embodiments could provide a high electric field strength in more than one separation arm at a time. For example, in the exemplary embodiment having six separation arms, two separation arms could be provided with a high electric field strength and four separation arms provided with a low electric field strength and the electric field pattern could be rotated.

Separation arms 32 need not be symmetrically disposed as illustrated. Separation arms 32 need not be generally rectangular in shape as illustrated. Separation arms 32 need not extend in straight lines as illustrated. A symmetrical arrangement of separation arms can help to provide a uniform electric field strength in each of the separation arms. Configurations of apparatus 30, including separation arms 32 and central reservoir 34, that interfere appreciably with the uniform flow of electric current through each separation arm 32 should be avoided if maximum efficiency is desired.

Separation arms 32A, 32B and 32C need not all have the same shape as one another as illustrated. For example, the widths, lengths and/or shape of separation arms 32 could be varied relative to one another, provided that the overall volume and geometry is such that the electric fields are matched in each separation arm 32. Where the separation arms will be loaded with particles to be separated, the configuration of the separation arms should be selected so that the driving and mobility altering fields will be consistent across all configurations of a cycle. For example, in embodiments in which the electric field is both the driving field and the mobility altering field, the geometry of each separation arm and the applied voltage should be selected so that the field strength is consistent across any given cross section of the width of each separation arm loaded with sample for each configuration of the electric field. In embodiments in which the electric field is the driving field and Joule heating is used to generate heat so that temperature is used in whole or in part as the mobility altering field, the geometry of each separation arm and the applied voltage should be selected so that the temperature and electric field strength are consistent across any given cross-section of the width of each separation arm loaded with sample for each configuration of the electric field, and so that equilibrium points are avoided. If a particular separation arm will not be loaded with particles to be separated, that particular separation arm can have any desired geometry. In some such embodiments, the impedance of that particular separation arm is approximately the same as the impedance of the other separation arms to avoid creation of a bias.

FIGS. 13A-13D illustrate a second exemplary embodiment of an apparatus 130 for separating particles. Portions of apparatus 130 that correspond in function to portions of apparatus 30 are indicated with like reference numerals incremented by 100. In the illustrated embodiment, separation arms 132 are disposed between a base plate 162 and a top plate 164 (see FIGS. 14A and 14B). Access apertures 168 (FIG. 14A) define portions of central reservoir 134, loading reservoirs 138, and buffer chambers 140 and 144. The depths of central reservoir 134, loading reservoirs 138, and buffer chambers 140 and 144 is thus defined in part by the thickness of top plate 164 (FIG. 14B). In the illustrated embodiment, central reservoir 134, loading reservoirs 138, and buffer chambers 140 and 144 are all deeper than the thickness of separation medium 136 (FIG. 14B).

In the illustrated embodiment, central reservoir 134 is of a generally triangular shape, with rounded or trimmed corners 135. Central reservoir 134 is shaped to minimize any potential distortions to the electric field used to move sample particles in arms 132.

Figure 13A:
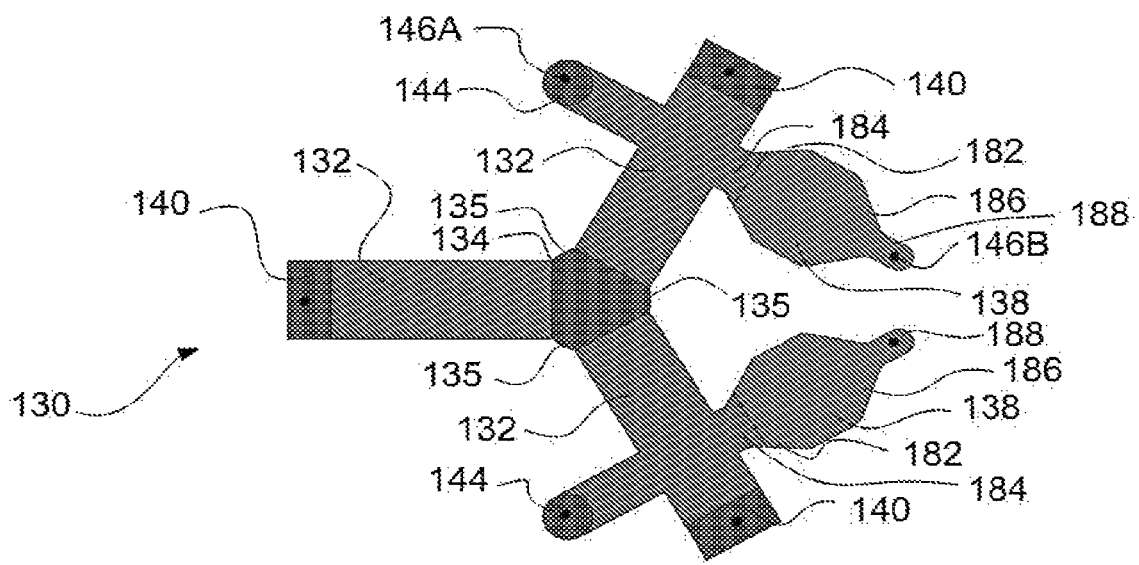
FIG. 13A is a top view showing schematically the configuration of a separation medium according to another embodiment.
Figure 13B:
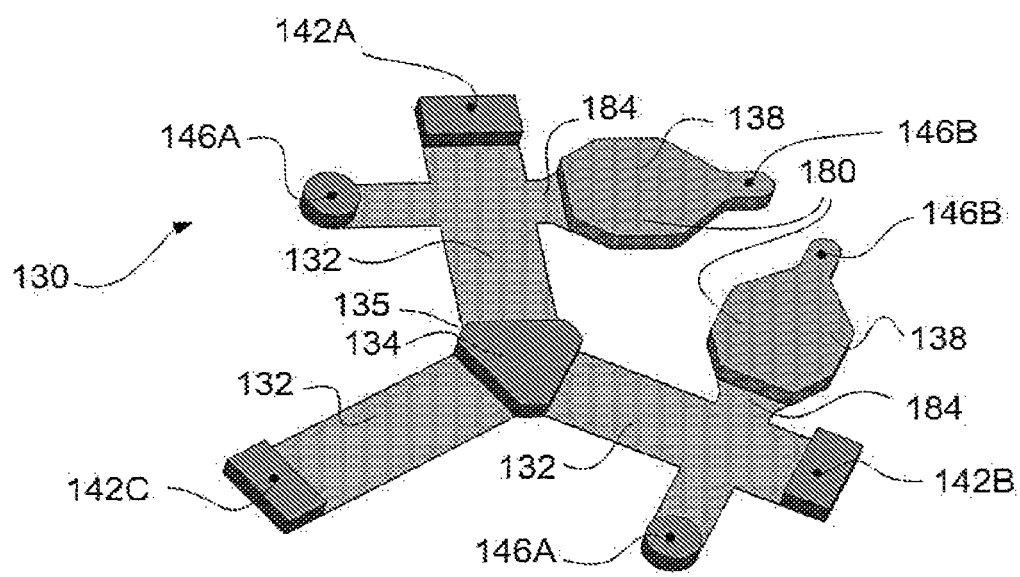
FIG. 13B is a perspective view of the separation medium of FIG. 13A.
Figure 13C:
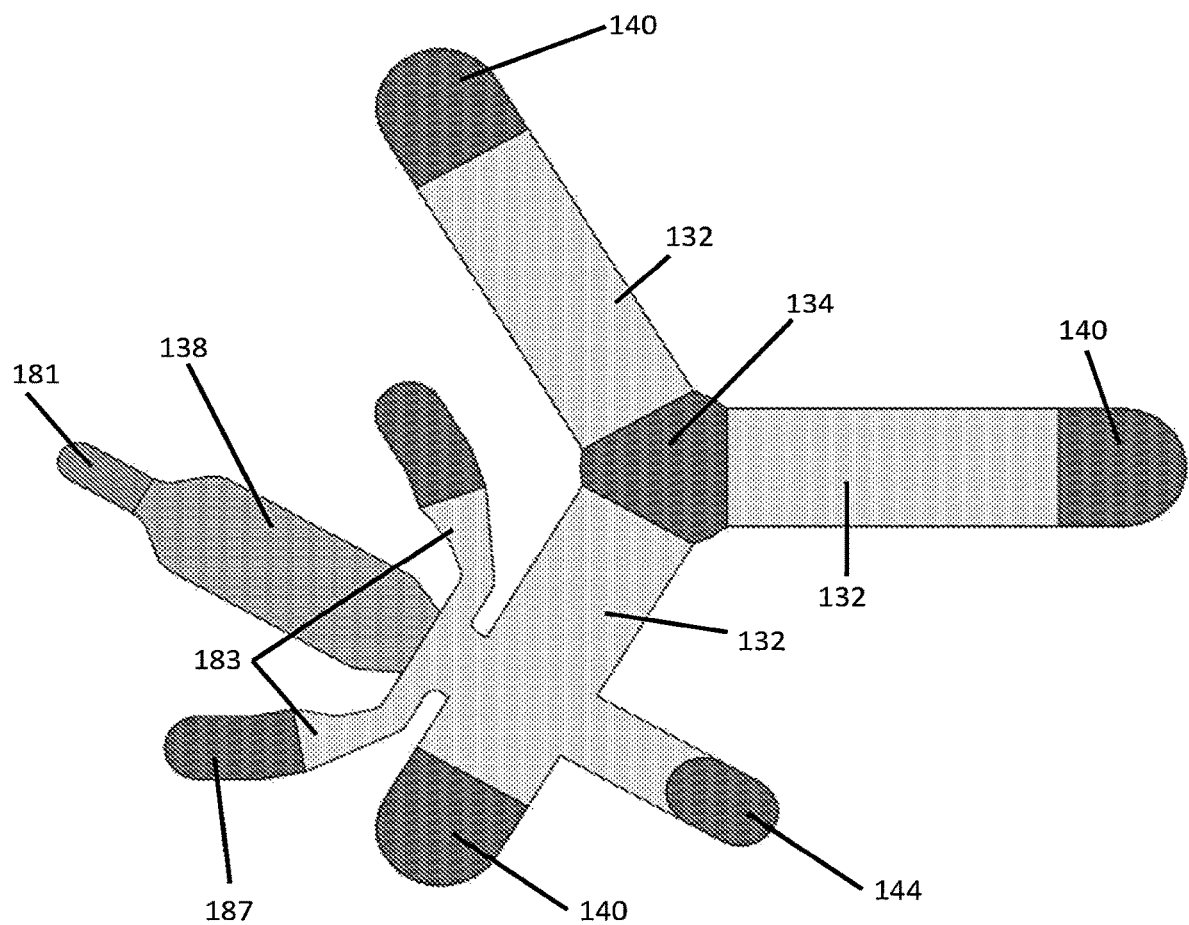
FIG. 13C is a top view of an alternate embodiment of FIG. 13A having streamlines that help constrain the sample during injection.
Figure 13D:
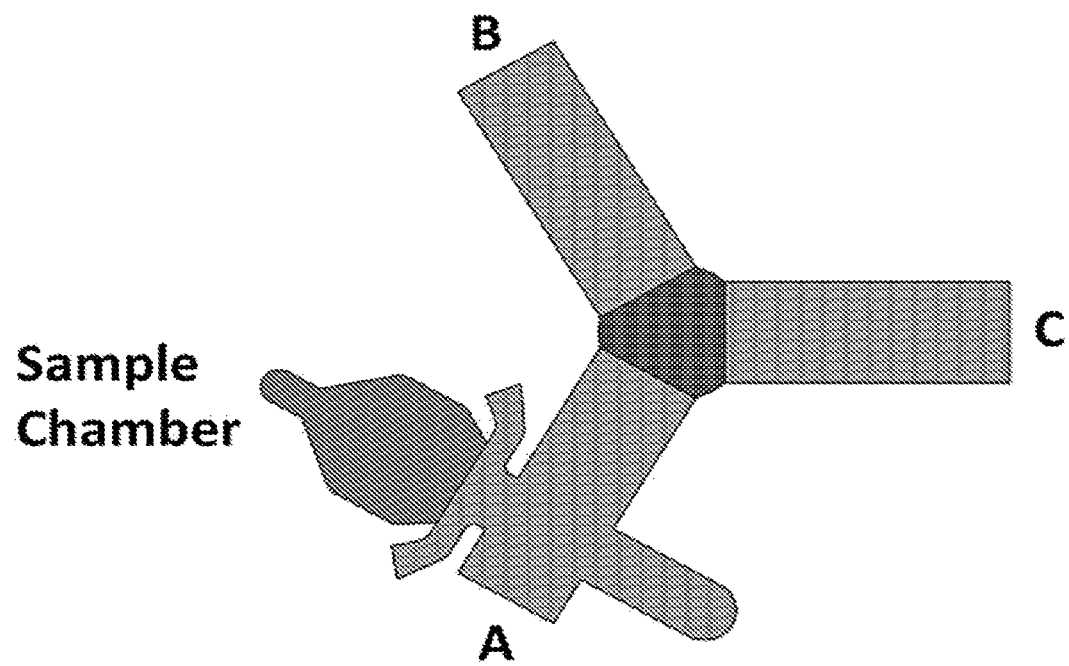
FIG. 13D is a top view of an alternate embodiment of FIG. 13A having streamlines that help constrain the sample during injection.

In the illustrated embodiment of FIGS. 13A and 13B, loading reservoir 138 has a relatively wider middle portion 180. However, loading reservoir 138 can be of the same width as separation arms 132, as shown in FIG. 13C. In FIGS. 13A and 13B, tapered portion 182 narrows from middle portion 180 toward an injection surface 184 on separation arm 132. A second tapered portion 186 narrows from middle portion 180 toward an electrode chamber 188 for receiving a loading electrode, shown schematically as 146B. A separate loading buffer chamber 144 receives loading electrode 146A.

In some embodiments, loading of sample into the separation arms is enhanced. For example, in the embodiment illustrated in FIGS. 13A and 13B, loading reservoir 138 has a greater depth than the thickness of separation medium 136. Providing a loading reservoir 138 with a height greater than the thickness of separation medium 136 allows the sample volume to be increased, without making the surface area required for loading reservoir 138 unduly large. In other embodiments, as depicted in FIG. 13C, sample loading can be enhanced with the inclusion of electrical streamlines 183. Electrical streamlines 183 are in the same plane as the gel of separation arms 132, and help constrain the sample to a narrow physical window during injection. When used, a voltage is applied from the agarose dam 181 and electrical streamlines 183 to the electrode across the separation arm 132. When used to load nucleic acids, for example, the configuration in FIG. 13C reduces loading losses due to nucleic acid spreading upon injection. Such techniques are especially useful when evaluating high value samples, such as forensic crime samples, where any nucleic acid loss can skew the results.

Figure 14A:
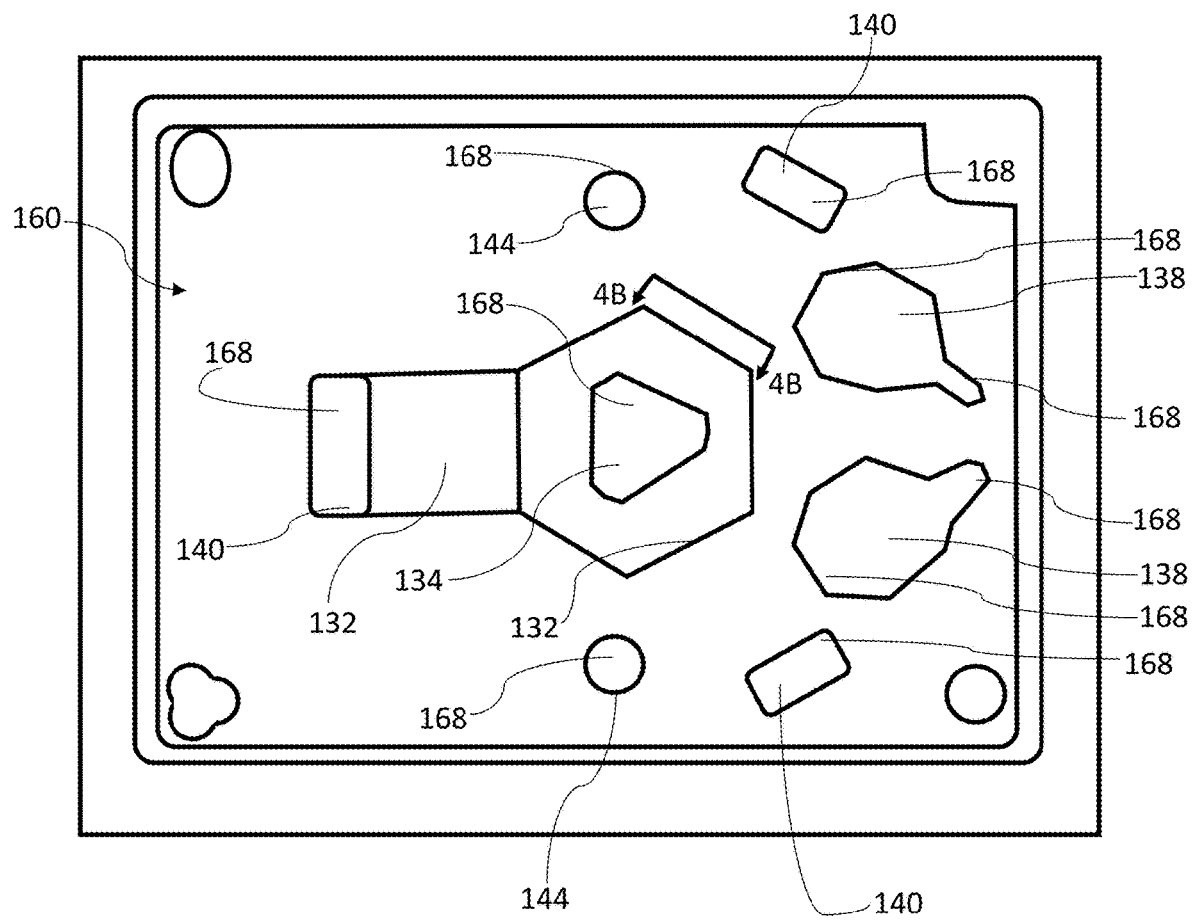
FIG. 14A is a top view of a photograph of a gel cassette for use with the apparatus of FIGS. 13A and 13B.
Figure 14B:
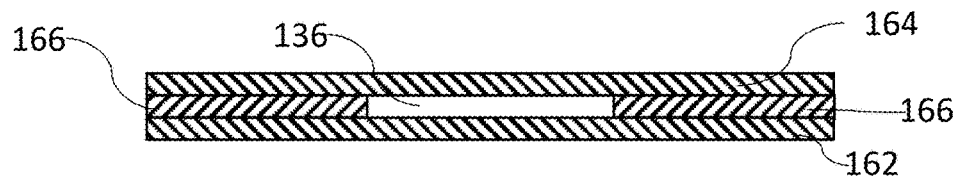
FIG. 14B is a schematic cross-sectional drawing of the cassette of FIG. 14A.
Figure 15A:
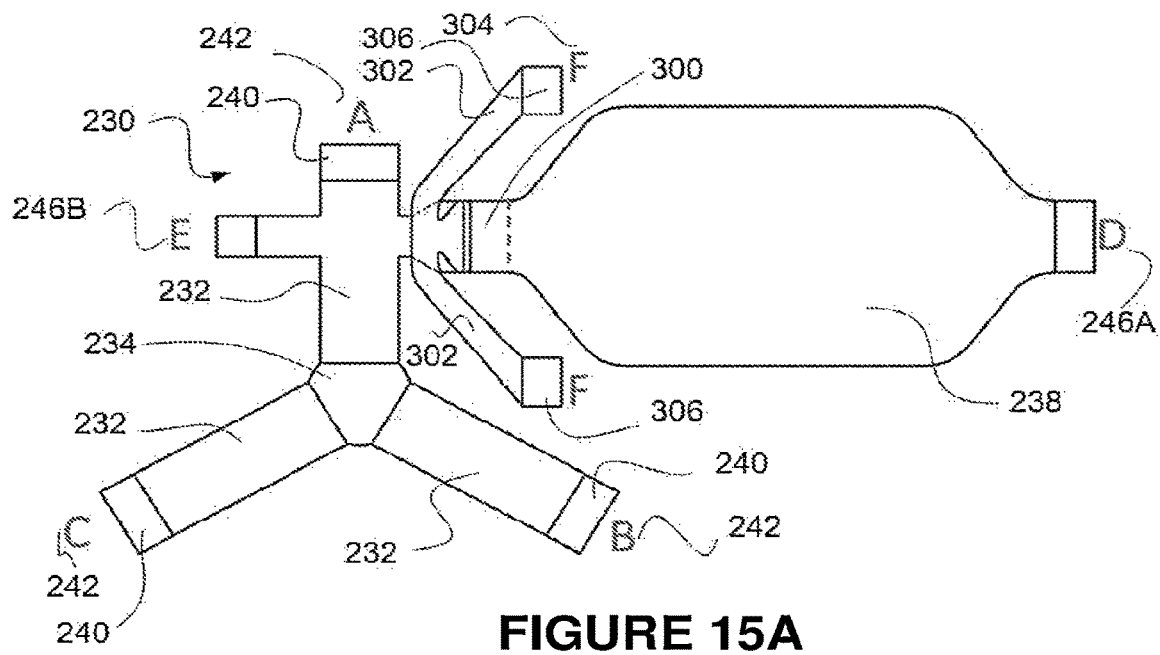
FIG. 15A illustrates a further embodiment of an example apparatus for separating particles with a sample loading interface including a filter gel and a sample loading interface wherein two Peltier elements are provided to independently control the temperature of regions of the sample loading interface and separation arm.
Figure 15B:
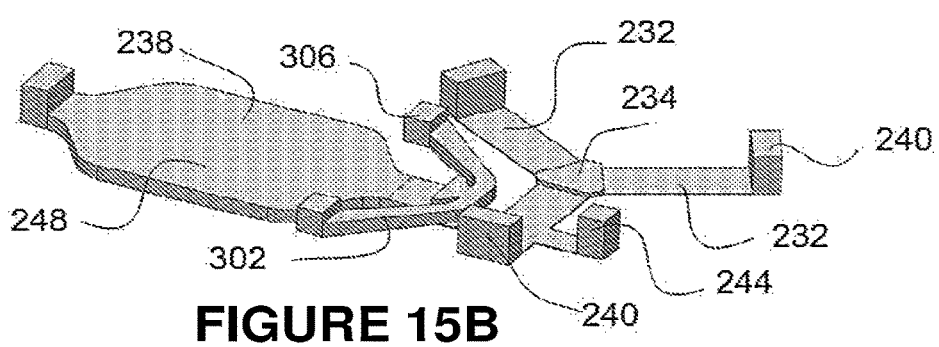
FIG. 15B illustrates a further embodiment of an example apparatus for separating particles with a sample loading interface including a filter gel and a sample loading interface wherein two Peltier elements are provided to independently control the temperature of regions of the sample loading interface and separation arm.
Figure 15C:
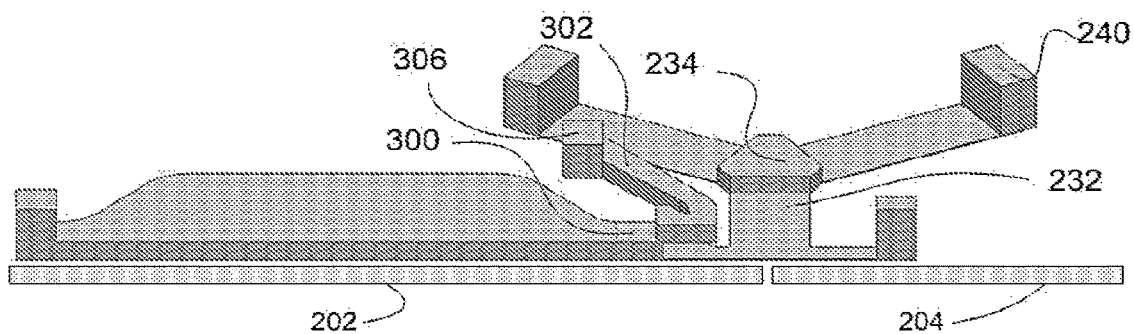
FIG. 15C illustrates a further embodiment of an example apparatus for separating particles with a sample loading interface including a filter gel and a sample loading interface wherein two Peltier elements are provided to independently control the temperature of regions of the sample loading interface and separation arm.
Figure 15D:
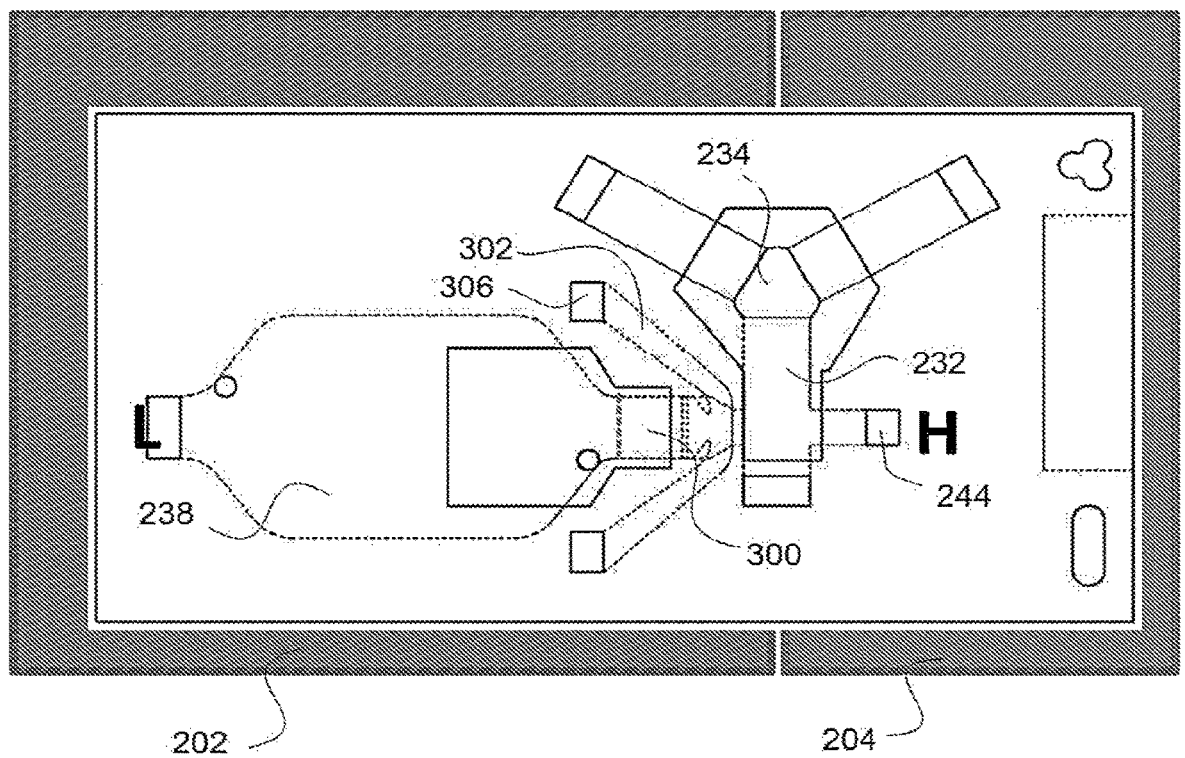
FIG. 15D illustrates a further embodiment of an example apparatus for separating particles with a sample loading interface including a filter gel and a sample loading interface wherein two Peltier elements are provided to independently control the temperature of regions of the sample loading interface and separation arm.

With reference to FIGS. 14A and 14B, in one embodiment a cassette 160 for use with apparatus 130 has a base plate 162 and a top plate 164. Plates 162, 164 may be made of any suitable non-electrically-conductive material, for example plastic, acrylic or glass. In embodiments in which temperature is used as the mobility altering field, at least one of base plate 162 and top plate 164 should be made from a material with good thermal conductivity, for example, glass.

Base plate 162 may be secured to top plate 164 in any suitable manner, for example by being integrally formed therewith, clamped thereto, secured thereto with an acceptable adhesive, or the like. In the illustrated embodiment of FIGS. 14A and 14B, base plate 162 is secured to top plate 164 using a layer of pressure sensitive adhesive 166. Pressure sensitive adhesive 166 maintains the spacing between base plate 162 and top plate 164. Pressure sensitive adhesive is cut to provide the desired configuration of separation medium 136. That is, portions of pressure sensitive adhesive 166 are removed where pressure sensitive adhesive 166 would otherwise interfere with separation arms 132, central reservoir 134, loading reservoir 138, electrode buffer chambers 140, loading buffer chambers 144, or the like. For example, where the separation medium is a gel such as polyacrylamide or agarose, pressure sensitive adhesive 166 can be cut to the desired shape, bonded between base plate 162 and top plate 164, and the gel can be poured in each separation arm 132. Where the separation medium is relatively thin, e.g. 100 μm, capillary action will draw the gel between plates 162, 164, and the gel will take on the shape defined by pressure sensitive adhesive 166. Access apertures 168 are provided in the top plate to provide access to loading reservoirs 138, central reservoir 134, to enable electrodes 140, 142, 146 to be inserted into the corresponding buffer chambers. In embodiments in which the gel is sufficiently thick that capillary action will not prevent the gel from entering loading reservoirs 138, central reservoir 134, electrode buffer chambers 140 or loading buffer chambers 144, suitable gel dams or other structures can be used to prevent the gel from flowing into these regions when being poured.

In the illustrated embodiment, the thickness of separation medium 136 is defined by the thickness of the layer of pressure sensitive adhesive 166. Separation medium 136 may have any desired thickness. In some exemplary embodiments, separation medium 136 is 100 μm thick. The thickness of separation medium 136 could be increased to increase the sample capacity of cassette 160. However, if separation medium 136 is made too thick, separation medium 136 will take longer to heat and cool (i.e. the thermal response time of separation medium 136 will be increased), which may be undesirable in some embodiments that use temperature as the mobility altering field. The thermal relaxation time of a separation arm filled with separation medium approximately 100 μm thick has been found to be on the order of ~200 ms in one exemplary embodiment. If separation medium 136 is made too thin, the capacity of cassette 160 may become undesirably low. The capacity of cassette 160 is determined by the volume of a sample to be loaded, the mass of charged target particle (e.g. DNA) to be loaded, and the concentration of electrically charged species (including salts) in the sample.

In some embodiments, a filter gel can be used upstream of a separation medium to reduce the level of contaminants present in a sample before target particles are subjected to separation, as well as to increase the capacity of the separation medium. The capacity of an apparatus can depend on all of the volume and salinity of a sample and the amount of charged target and contaminant particles present in a sample. That is, the capacity of an apparatus may be limited by any of the volume of a sample (a sample which is too large in volume may not be loaded), the salinity of a sample (i.e. the presence of too many ions may interfere with electrophoresis if the salinity of the sample is too high), or the amount of target particle in a sample (e.g. the presence of too much nucleic acid in the sample, whether target or contaminating sequence, may interfere with electrophoresis). A filter gel as described below allows for a larger volume of sample to be loaded, allows for the removal of excess ions in the sample during loading, and/or allows for the removal of particles similar in nature to the target particle but which do not interact as strongly with the immobilized agent in the filter gel (e.g. for the removal of nucleic acids that have a sequence that is not similar to a target nucleic acid). In use, a filter gel can be positioned upstream of the separation apparatus, so that particles can be first loaded into the separation gel, and then loaded onto the separation apparatus.

A filter gel is a separation medium (for example agarose or polyacrylamide gel) that has an agent immobilized therein. The agent is selected to have a binding for target particles of interest (e.g. oligonucleotides having a particular sequence). A sample is injected into the filter gel by application of an electric field under conditions such that the target particles of interest bind to the immobilized agent (or alternatively the sample could be mixed with the filter gel when the filter gel is poured). Under the influence of the electric field, contaminating particles that do not bind to the agent pass through the filter gel. In some embodiments, the contaminating particles can be removed via an exhaust gel downstream of the filter gel during sample loading, so that contaminating particles do not enter the separation medium.

After contaminating particles have passed through the filter, conditions are changed so that the target particles do not bind the agent (e.g. the temperature is raised), and an electric field is applied to inject the target particles from the filter gel into the separation medium. A filter gel can be used together with any apparatus for conducting electrophoresis to reduce the level of contaminants present and/or to increase the capacity of the apparatus. For example, a filter gel could be provided upstream of a conventional electrophoresis gel used to separate oligonucleotides based on size.

FIGS. 15A, 15B, 15C and 15D illustrate a third exemplary embodiment of an apparatus 230 for separating particles. Portions of apparatus 230 that correspond in function to portions of apparatus 30 are identified by like reference numerals incremented by 200. In the illustrated embodiment, loading reservoir 238 is thicker than the separation medium in separation arms 232. A filter gel 300 is provided at the end of loading reservoir 238 adjacent separation arm 232 (the edge of the filter gel 300 is indicated by a dashed line). Filter gel 300 includes a plurality of immobilized agents that bind to target particles in sample 248. In some embodiments, the plurality of immobilized agents are all the same agent. During injection of sample 248 into separation arm 232, target particles can be bound to the immobilized agents in filter gel 300 while contaminating particles are washed through filter gel 300. After sample 248 has been loaded, target particles can then be eluted for injection into separation arm 232 in any suitable manner In some embodiments, target particles are bound to the immobilized agents in filter gel 300 at a relatively low temperature, and the target particles are eluted by increasing the temperature to a level where the target particles do not bind significantly to the immobilized agents. In some embodiments, separation arm 232 includes the same agent as filter gel 300. In some embodiments, separation arm 232 includes a different agent than filter gel 300. In some embodiments, the agent in filter gel 300 has a stronger binding for both the target particle and non-target particles than the agent in separation arms 232. In some embodiments, separation arm 232 does not include an agent, while filter gel 300 does include an agent.

In some embodiments, temperature regulators such as heating and/or cooling units are provided adjacent to the medium to facilitate temperature control. In some embodiments, one or more Peltier elements are provided to adjust the temperature of the separation medium. In some such embodiments, the Peltier elements are positioned adjacent to the base plate (e.g. base plate 162) and the base plate is made from a thermally conductive material, e.g. glass. In some embodiments, a controller is provided to regulate the operation of the Peltier elements and/or the electrodes. Peltier elements can be used to heat and/or cool the separation medium, depending on the desired application.

In some embodiments, including the illustrated embodiment of FIGS. 15A, 15B, 15C and 15D, two Peltier elements 202, 204 (shown only in FIGS. 15C and 15D) are provided adjacent separation arm 232 and filter gel 300, beneath the base plate of the gel cassette (not shown). Peltier elements 202, 204 are independently operable; that is, the temperature of each of Peltier elements 202 and 204 can be separately controlled. In some embodiments, a controller is provided to control the operation of Peltier elements 202, 204 and/or electrodes 242, 304 and/or 246A/246B (the electrodes are schematically labeled as the letters A, B and C (electrodes 242), F (304), D (246A) and E (246B) in FIG. 15A). In some embodiments, including the illustrated embodiment, Peltier elements 202, 204 abut one another within (in the illustrated embodiment, at approximately the midpoint of) the width of separation arm 232. To inject sample 248 into separation arm 232, an electric field is applied across loading electrodes 246A and 246B (or, as described below, electrodes 246A and 304) Initially, the temperature of Peltier element 202, which is adjacent filter gel 300, is maintained at a low temperature at which the target particle binds strongly to the immobilized agent (e.g. a temperature below the melting temperature of the target particle-agent duplex). Contaminating particles do not bind to the immobilized agent, or bind the immobilized agent to a lesser extent than the target particles. Consequently, contaminating particles can be washed through the filter gel 300, while the target particles are stacked at approximately the interface between loading reservoir 238 and filter gel 300. This step can be described as "filter injection".

After sample 248 has been loaded on filter gel 300, the temperature of Peltier element 202 can be increased to a level at which the target particles bind poorly or not at all to the immobilized agent (e.g. a temperature above the melting temperature of the target particle-agent duplex). Continued application of an electric field across loading electrodes 246A and 246B will cause the target particles to be injected into separation arm 232. This step can be described as "hot injection" of the target particles.

In some embodiments, including the illustrated embodiment, separation arm 232 also includes an immobilized agent that binds to the target particles. Target particles can be stacked in the separation medium prior to the application of electric fields to separate the particles by providing a temperature gradient in the path of travel of particles entering the separation medium. For example, a temperature profile can be created across the width of the separation arm, such that target particles entering the separation medium from the filter gel are at a high temperature at which the target particles bind poorly or not at all to the immobilized agent, while a point within the path of travel of the target particles entering the separation arm downstream of the filter gel is at a relatively low temperature at which the target particles are likely to remain bound to the immobilized agent. Target particles will tend to bind to the immobilized agent at the point where the temperature drops, thereby stacking the target particles within the separation medium.

For example, in the illustrated embodiment, a second Peltier element 204 is provided adjacent separation arm 232 and in the path of travel of particles being injected into separation arm 232. Peltier elements 202 and 204 are positioned so that the interface between the two elements is at a convenient location relative to the width of separation arm 232. In some embodiments, the interface between Peltier elements 202 and 204 is located at approximately the midpoint of the width of separation arm 232. Peltier elements 202 and 204 can be spaced apart. In some embodiments, Peltier elements 202 and 204 are positioned close together, so that target particles can be stacked in a narrow band as described below.

Stacking of target particles within separation arm 232 may be done by filter injection of the target particles in filter gel 300 as described above, followed by hot injection of the target particles into separation arm 232 by increasing the temperature of Peltier element 202. During the hot injection step, the temperature of Peltier element 204 is maintained at a low temperature at which the target particles bind effectively to the immobilized agent in separation arm 232 (e.g. at a temperature below the melting temperature of the target particle-agent duplex). After the target particles have been stacked in separation arm 232, the temperature of Peltier element 202 can be reduced and the temperature of Peltier element 204 can be increased so that the temperature of both elements 202 and 204 is approximately the same, and is at a level at which the electric fields are to be applied to electrodes 242 (represented by the letters A, B and C in FIG. 15A).

In some embodiments, loading reservoir 238 includes exhaust arms 302, as in the illustrated embodiment of FIGS. 15A, 15B, 15C and 15D. The exhaust arms are provided to receive contaminants flowing through the filter gel during sample loading. Exhaust arms allow contaminants to be removed from the sample and from the filter gel without allowing the contaminants to enter the separation medium. By applying an electric field across both the filter gel and the exhaust arms, contaminants that do not bind to the immobilized agent within the filter gel can be removed, without contaminating the separation medium.

In some embodiments, exhaust arms 302 are filled with the same gel as filter 300. In some embodiments, the gel filling exhaust arms 302 includes an immobilized agent therein. Exhaust arms 302 are coupled to a loading electrode 304 (represented schematically as the letter F in FIG. 15A) which sits in a loading electrode buffer chamber 306. In the illustrated embodiment, two exhaust arms 302 extend outwardly from filter gel 300. Exhaust arms 302 can be provided with any desired configuration. In some embodiments, exhaust arms 302 can conveniently extend out of the plane of the separation medium to remove contaminant particles.

In the illustrated embodiment, exhaust arms 302 contact filter gel 300 at a point vertically above the surface of loading reservoir 238. In this way, an electric field can be applied between electrodes 246A and 304 to remove contaminants during stacking of target particles in filter gel 300. Such contaminants do not enter separation arm 232, as the contaminants pass through exhaust arms 302 to buffer chamber 306.

Figure 16:
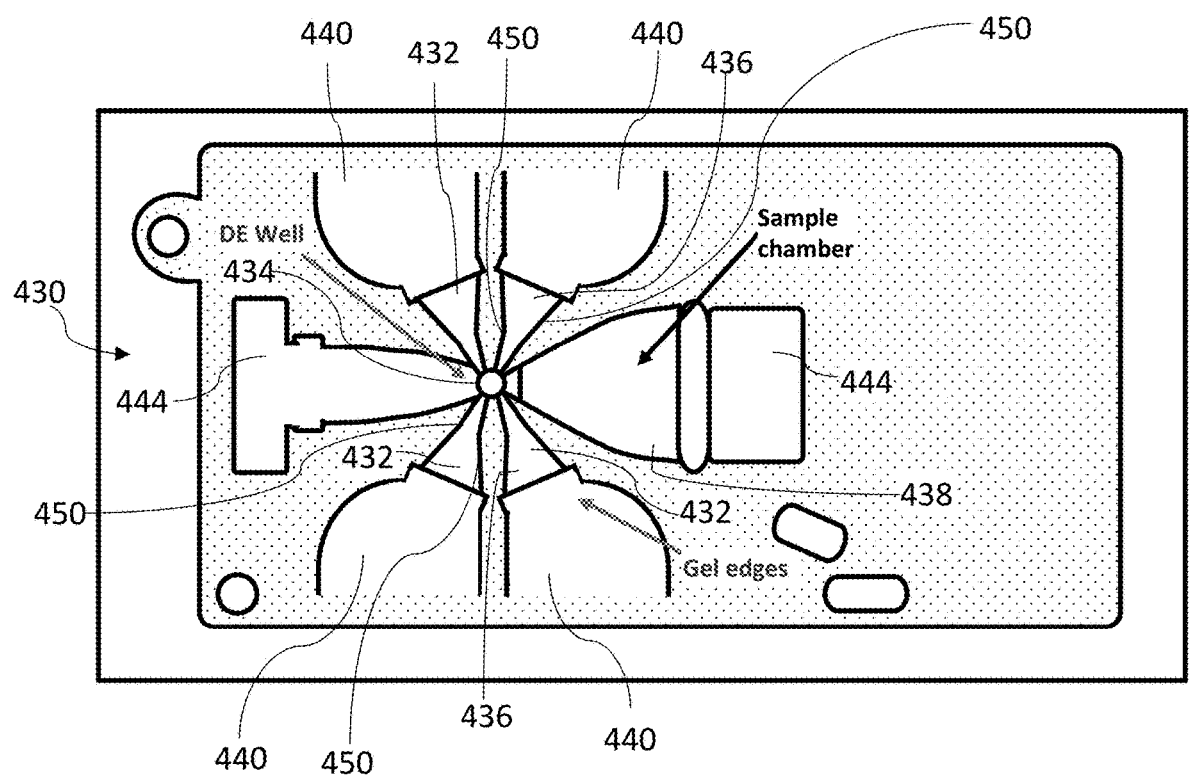
FIG. 16 is a top view of a further embodiment of an example apparatus for separating particles having four tapered separation arms.

FIG. 16 shows a further embodiment of an example apparatus 430 for separating particles. Portions of apparatus 430 that correspond in function to portions of apparatus 30 are indicated by like reference numerals incremented by 400. Apparatus 430 has four separation arms 432. The separation arms 432 of apparatus 430 are tapered, that is, the width of separation arms 432 at a point proximate central reservoir 434 is narrower than the width of separation arms 432 at a point distal from central reservoir 434. By varying the width of separation arms 432 along their length, the magnitude of current density at any given point along the length of separation arms 432 can be varied. That is, due to conservation of electric charge, the amount of charge passing through a cross-section taken at any point along the length of separation arm 432 must be the same as the amount of charge passing through a cross-section taken at any other point along the length of separation arm 432. Thus, the amount of current passing through a cross-section at which separation arm 432 is relatively narrower will be larger than the amount of current passing through a cross-section at which separation arm 432 is relatively wider. The temperature within the separation medium can be varied based on the amount of current passing through a cross-section at a particular point within the separation arm 432.

In some embodiments, including the illustrated embodiment, the tapered separation arms 432 have a point at which the angle of taper outwardly from a center line running along the length of the separation arms increases slightly, indicated at 450. The presence of a point or region 450 at which the angle of taper changes can help to enhance the effects of changes in temperature and electric field strength, resulting in a sharper separation of particles.

The creation of varying electric field strengths or temperatures within the tapered separation arms 432 allows for the creation of equilibrium points for particles with certain characteristics within separation arms 432. For example, for particles that have a mobility that varies with both electric field strength and temperature, by selection of appropriate conditions, at a certain point along the length of separation arms 432, the net motion of a target particle in one cycle can change from net negative (i.e. away from central reservoir 434) to net positive (i.e. toward central reservoir 434). The target particle will tend to remain at that equilibrium point within separation arm 432. After other particles have been moved out of separation arms 432, the operating conditions can be adjusted so that the target particle experiences net positive motion towards central reservoir 434. Target particles can then be removed from central reservoir 434 and subjected to further analysis.

For example, the illustrated embodiment of FIG. 16 can be used to separate oligonucleotides such as DNA based on size. The oligonucleotides can be loaded on the separation arms 432 using sample chamber 438 by injecting oligonucleotides through central reservoir 434 by the application of an electric field. The mobility of DNA through the separation medium varies with both temperature and electric field strength. The temperature dependence and electric field strength dependence of the mobility of larger DNA particles are both greater than the temperature dependence and electric field strength dependence of the mobility of shorter DNA particles. These differences can be used to separate DNA based on length.

Electric fields can be applied to cause net movement of the DNA in a selected direction based on the change in mobility of the DNA with changes in electric field strength. For example, the DNA can be caused to move inwardly by the application of a high positive voltage to three electrodes positioned at the distal ends of the separation arms and a low voltage to the fourth electrode positioned at the distal end of the separation arm) in the manner described above. Such electric fields can be termed focusing fields (because DNA tends to be focused in central reservoir 434). The DNA can alternatively be caused to move outwardly by the application of a high positive voltage to one electrode and a low voltage to the remaining three electrodes at the distal end of the separation arms. Such electric fields can be termed defocusing fields (because the DNA tends to move outwardly, away from central reservoir 434).

Application of the electric fields also causes a change in temperature of the separation medium. Because the separation arms have a tapered shape, a larger amount of current will pass through a cross section of the separation arm taken nearer to the central reservoir 434 than farther away from the central reservoir 434. Consequently, the amplitude and phase of the thermal oscillations established by the application of the electric fields change along the length of the separation arms. Because DNA mobility also depends on both temperature and electric field strength, the net movement of the DNA along the length of the separation arm will depend on the relative dominance of changes in mobility in response to temperature oscillations within the separation medium versus changes in mobility in response to changes in electric field strength. When applying defocusing fields, if conditions are chosen so that the phase of the thermal oscillations is out of phase with the defocusing electric fields towards the distal portion of the separation arms (e.g. due to a high thermal lag time for the gel to be heated due to Joule heating), some molecules will reach an equilibrium position, at which net movement toward the distal end of the separation arm caused by changes in mobility due to the changes in electric field strength will be equal to net movement toward central reservoir 434 caused by changes in mobility due to changes in temperature within the separation medium. That is, the net movement due to changes in mobility caused by changes in electric field strength will be in one direction (distally away from central reservoir 434) while net movement due to changes in mobility caused by changes in temperature can be in the opposite direction (i.e. toward central reservoir 434). Conditions can be selected so that the equilibrium position for DNA having a particular size of interest is inside the separation arms, while DNA having other sizes is washed out of the distal ends of the separation arms.

In alternative embodiments, a temperature gradient can be established using heating or cooling units positioned adjacent to any shaped separation arm (e.g. a rectangularly-shaped separation arm) to create equilibrium points in a similar manner.

In some embodiments, the separation of one particle from other similar particles is enhanced by applying a wash field superimposed over the electric fields used to separate particles. In some embodiments, the wash field is an electric field. In some embodiments, the wash field is provided by applying the electric field in one configuration of the cycle for a longer period of time (a washing time) than the electric field is applied in the other n–1 configurations of the cycle. The temperature and duration for which the wash field is applied can be adjusted to effect separation of particles based on the differences in of the particles for an immobilized agent. The washing field essentially causes a departure from the condition that the net motion for particles whose mobilities do not vary under the influence of the mobility altering field is zero.

Using an exemplary embodiment having three separation arms, Table 9 summarizes an exemplary voltage pattern that could be used to separate particles with a washing field using the exemplary embodiment illustrated in FIG. 11. In the exemplary embodiment described below, the mobility altering field is provided by Joule heating caused by the electric field that provides the driving field. In this embodiment, the temperature of the separation medium is maintained at a desired base temperature, e.g. in the range of 40° C. to 60° C., for example using a Peltier element as described above, and the heat produced by the electric field is sufficient to produce the desired increase in temperature. Because of Joule heating due to the passage of current through the separation medium, the temperature within the separation medium will generally be higher than the base temperature set by a temperature controller (e.g. the temperature in the separation medium will generally be higher than the temperature of the Peltier element).

TABLE 9

Exemplary voltage pattern for embodiment with three separation arms providing a washing field.

| Step | Electrode 42A | Electrode 42B | Electrode 42C | Duration |
|---|---|---|---|---|
| 1 | H | L | H | 1 second |
| 2 | L | H | H | 1 second |
| 3 | H | H | L | 1 second |
| 4 | H | H | L | 0.5 second |

In the exemplary embodiment summarized in Table 9, step 4 provides the washing electric field to the separation arms.

Figure 17:
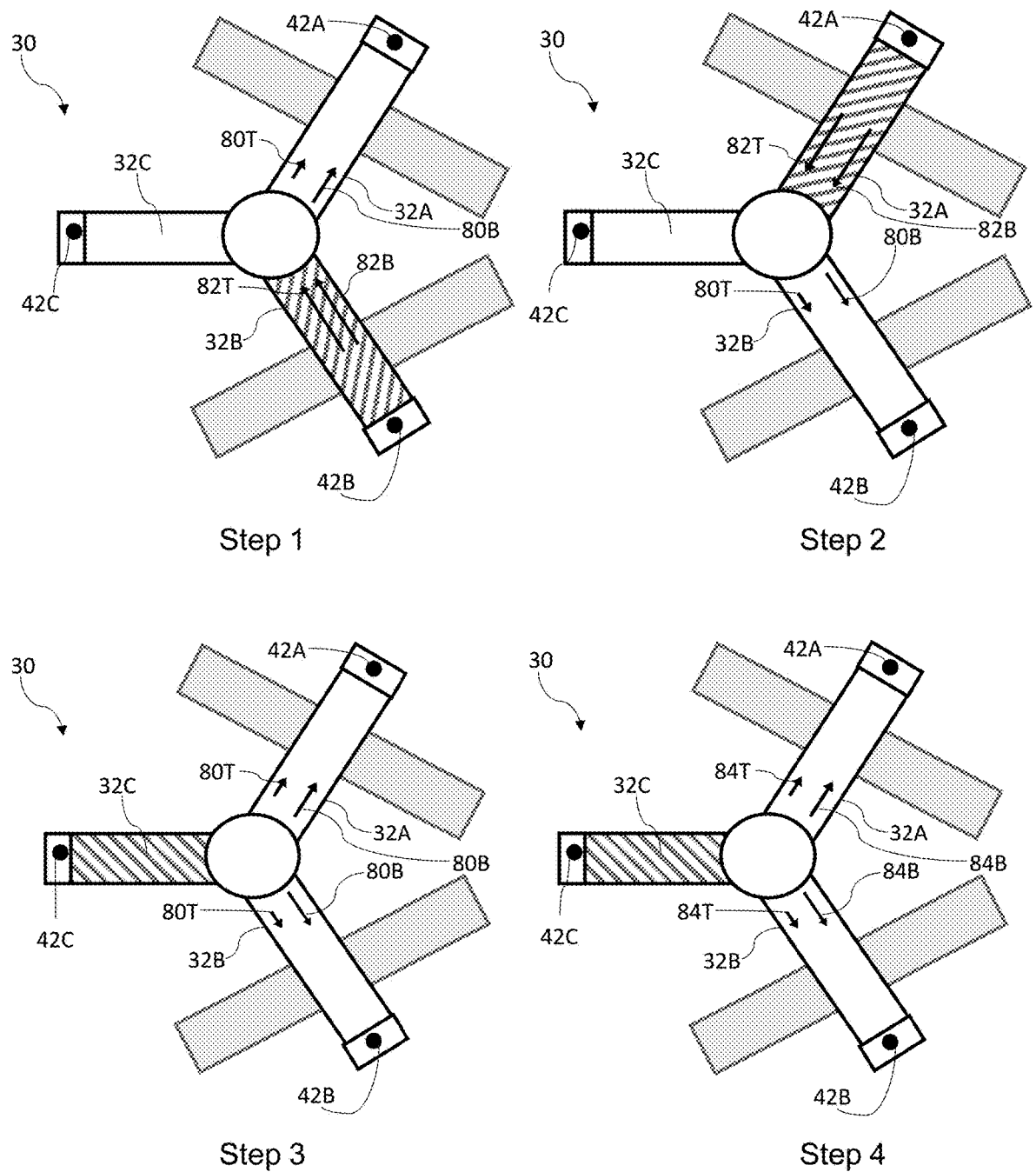
FIG. 17 shows the movement of a hypothetical particle under applied electric fields in an exemplary embodiment using a wash field.

With reference to FIG. 17, the movement of an exemplary pair of oligonucleotide molecules, a target molecule having a perfect sequence match to an oligonucleotide probe immobilized within the separation medium, and a background molecule having a single base mismatch to an oligonucleotide probe immobilized within the separation medium, under the applied electric fields is described. For purposes of the exemplary description below, a mixture of target and background molecules is loaded on each of separation arms 32A and 32B and injected into the separation medium. No sample is loaded on separation arm 32C, which is a washing arm as explained below.

In step 1, separation arms 32A and 32C are regions of low electric field strength (the voltages applied at electrodes 42A and 42C are high). Arm 32B is a region of high electric field strength, as indicated by diagonal shading. Due to conservation of current, the amount of heat being generated by Joule heating in the separation medium in arm 32B will be 4I greater than the amount of heat being generated by Joule heating in separation arms 32A and 32C, where I is the current flowing through each of separation arms 32A and 32C. Thus, arm 32B will also be at a higher temperature than arms 32A and 32C. Both the target and background molecules in separation arm 32A will move in a direction away from central well 34. Because the probability that the background molecules will be bound to the immobilized agent is less than the probability that the target molecules will be bound to the immobilized agent, on average the background molecules in separation arm 32A will move farther during this step than the target molecules in separation arm 32A. The magnitude and direction of this movement are indicated schematically by arrows 80T and 80B in FIG. 17.

In arm 32B, the temperature is higher than in arm 32A. Both the target molecule and the background molecule have a mobility within the medium that approaches the unbound mobility, i.e. the probability that either the target molecule or the background molecule will bind to the immobilized agent is low. Both the target molecule and the background molecule will move approximately the same distance toward central reservoir 34, as indicated schematically by arrows 82T, 82B. Because arm 32B is a region of high electric field strength, the distance travelled by both the target molecule and the background molecule will be greater than it would be at low field strength.

In step 2, separation arms 32B and 32C are regions of low field strength, while separation arm 32A is a region of high field strength, as indicated by diagonal shading. Due to conservation of current, the amount of heat being generated by Joule heating in the separation medium in arm 32A will be 4I greater than the amount of heat being generated by Joule heating in separation arms 32B and 32C, where I is the current flowing through each of separation arms 32A and 32C. Thus, separation arm 32A will also be at a higher temperature than arms 32B and 32C. Both the target and background molecules in separation arm 32B will move in a direction away from central well 34. Because the probability that the background molecules will be bound to the immobilized agent is less than the probability that the target molecules will be bound to the immobilized agent, on average the background molecules in separation arm 32B will move farther during this step than the target molecules in separation arm 32B. The magnitude and direction of this movement are indicated schematically by arrows 80T and 80B in FIG. 17.

In arm 32A, the temperature is higher than in arm 32B. Both the target molecule and the background molecule have a mobility within the medium that approaches the unbound mobility, i.e. the probability that either the target molecule or the background molecule will bind to the immobilized agent is low. Both the target molecule and the background molecule will move approximately the same distance toward central reservoir 34, as indicated by arrows 82T, 82B. Because arm 32A is a region of high electric field strength, the distance travelled by both the target molecule and the background molecule will be greater than it would be at low field strength.

In step 3, separation arms 32A and 32B are regions of low field strength, while separation arm 32C is a region of high field strength, as indicated by diagonal shading. Due to conservation of current, the amount of heat being generated by Joule heating in the separation medium in arm 32C will be 4I greater than the amount of heat being generated by Joule heating in separation arms 32A and 32B, where I is the current flowing through each of separation arms 32A and 32B. Thus, arm 32C will be at a higher temperature than arms 32A and 32B. Both the target and background molecules in separation arms 32A and 32B will move in a direction away from central well 34. Because the probability that the background molecules will be bound to the immobilized agent is less than the probability that the target molecules will be bound to the immobilized agent, on average the background molecules in separation arms 32A and 32B will move farther during this step than the target molecules in separation arms 32A and 32B. The magnitude and direction of this movement are indicated schematically by arrows 80T and 80B in FIG. 17.

In step 4, conditions remain the same as in step 3 for a further period of time (a washing time). Typically, the washing field applied at step 4 will be applied for a shorter period of time than the other configurations of the cycle. In this example, the electric field configuration of step 4 is applied for 0.5 seconds, whereas the electric fields of steps 1, 2 and 3 are applied for 1 second. Both the target and background molecules in separation arms 32A, 32B take a further step away from central reservoir 34, as illustrated by arrows 84T, 84B in FIG. 17. Because the time for which the washing field is applied is only ½ as long as the time for which the low electric field is applied in step 3, the distance traveled by both the target and background molecules in step 4 is on average only ½ as far as the distance traveled in step 3.

In some embodiments in which a wash field is to be applied, sample is loaded on only n−1 of the n separation arms. That is, no sample is loaded on one of the separation arms. For example, in an embodiment having three separation arms, sample is loaded on only two of the separation arms. The arm in which no sample is loaded can be referred to as a "washing arm". In the exemplary embodiment described above, application of the wash field moves negatively charged particles in two (i.e. n−1 where n is 3) of the separation arms away from the central reservoir (as described with reference to separation arms 32A and 32B above). Any negatively charged particles present in separation arm 32C will move towards the central reservoir under the influence of the wash field. Thus, negatively charged particles, including the background molecules, could experience net motion towards central reservoir 34 under the application of a wash field. Loading sample on separation arm 32C could lead to contamination of the target molecules recovered in central reservoir 34 with background molecules. In the illustrated embodiment, separation arm 32C is a wash arm. No sample is loaded on arm 32C. This avoids a risk that the washing field will cause negatively charged particles to move from arm 32C to central reservoir 34.

Where a component (e.g. a power supply, electrode, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Because heteroduplex binding proteins fail to recognize certain heteroduplexes, potentially due in part to a lack of flexibility in certain heteroduplexes, systems and methods of the invention also relate to promoting recognition of all heteroduplexes through modification of target heteroduplex nucleic acids. Certain heteroduplexes may be less flexible due to sequence context or mutation type. See Brown, et al., Affinity of mismatch-binding protein MutS for heteroduplexes containing different mismatches, Biochem J. 2001 Mar. 15; 354 (pt3): 627-633), incorporated herein by reference. In various embodiments, methods may include nicking of the target heteroduplex nucleic acid at a mismatch site to increase flexibility and promote heteroduplex binding protein (e.g., MutS) recognition and binding during separation. Nicking the heteroduplex may increase flexibility, allowing the heteroduplex-binding protein to recognize the heteroduplex.

In certain embodiments target heteroduplexed nucleic acids may be nicked through physical shearing, drying, or enzymatic reactions. Physical shearing may be accomplished through vortexing, sonication, pipetting, or other physical manipulation. In a preferred embodiment, nicking is accomplished through the use of nicking endonucleases. Any nicking endonuclease known in the art may be used including, for example those commercially available from New England Biolabs Inc. (Ipswich, Mass.) and ThermoFisher Scientific (Cambridge, Mass.). Other possibilities for enzymatic nicking contemplated by the invention include CEL I, CEL II, endonuclease V (*E. coli, T. maritima*), T7, thymine DNA glycosylase (TDG), SI nuclease, or mung bean nuclease.

Nicking may be mismatch site specific or may be non-specific. In certain embodiments, nicking may be accomplished through endonuclease cleavage of both variants (heteroduplex) and non-variants (homoduplex) at followed by ligation of only homoduplex nucleic acids as described in U.S. Pat. No. 7,960,159, incorporated herein by reference. The endonuclease may preferentially nick or cleave heteroduplexed products at a location one base away from mismatched base pairs and the following ligation reaction can use a ligase adapted to preferentially seal the nicked heteroduplexed products at perfectly matched base pairs without substantially resealing the nicked heteroduplexed products at locations adjacent to mismatched base pairs. Mismatches in heteroduplex nucleic acids may comprise single or multiple bases and single nucleic acid may contain multiple mismatch sites. Methods of the invention may include nicking all or only a portion of the mismatch sites in a given target heteroduplex nucleic acid.

EXAMPLES

Figure 18:
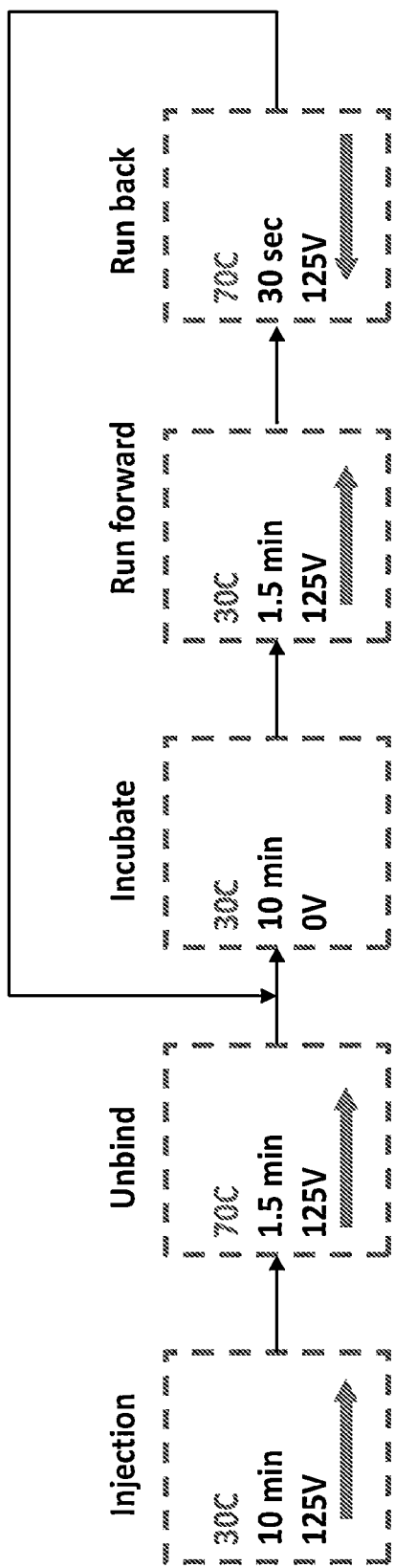
FIG. 18 shows an exemplary field sequence for separating target nucleic acid.

Example 1—Work Flow for Separation of Rare Nucleic Acid Mutation from a Sample FIG. 18 shows a block diagram detailing fields and temperatures for separating target nucleic acids. The process begins with an injection step, at low temperature, in which a mixture of homoduplexed and heteroduplexed nucleic acid is loaded onto a separation medium including the heteroduplex-binding protein MutS. Once the nucleic acids are in the working area of the separation medium after a high temperature step, the injection field is shut off and the temperature of the medium is cooled to encourage binding of heteroduplex binding protein to the heteroduplex nucleic acids. Fields at low temperature are applied for a period of time, after which the direction of the fields is reversed, and the temperature of the separation medium is raised, whereupon the heteroduplex binding protein dissociates from the heteroduplex. The temperature is then cooled to drive rebinding of the heteroduplex binding protein to the heteroduplex DNA, and the process (SCODAphoresis) is repeated. With repeated periods of driving forward and backward, along with changes in temperature, the heteroduplexed nucleic acids are gradually separated from the homoduplexed nucleic acids, thus allowing the heteroduplexed nucleic acids to be collected.

Figure 19A:
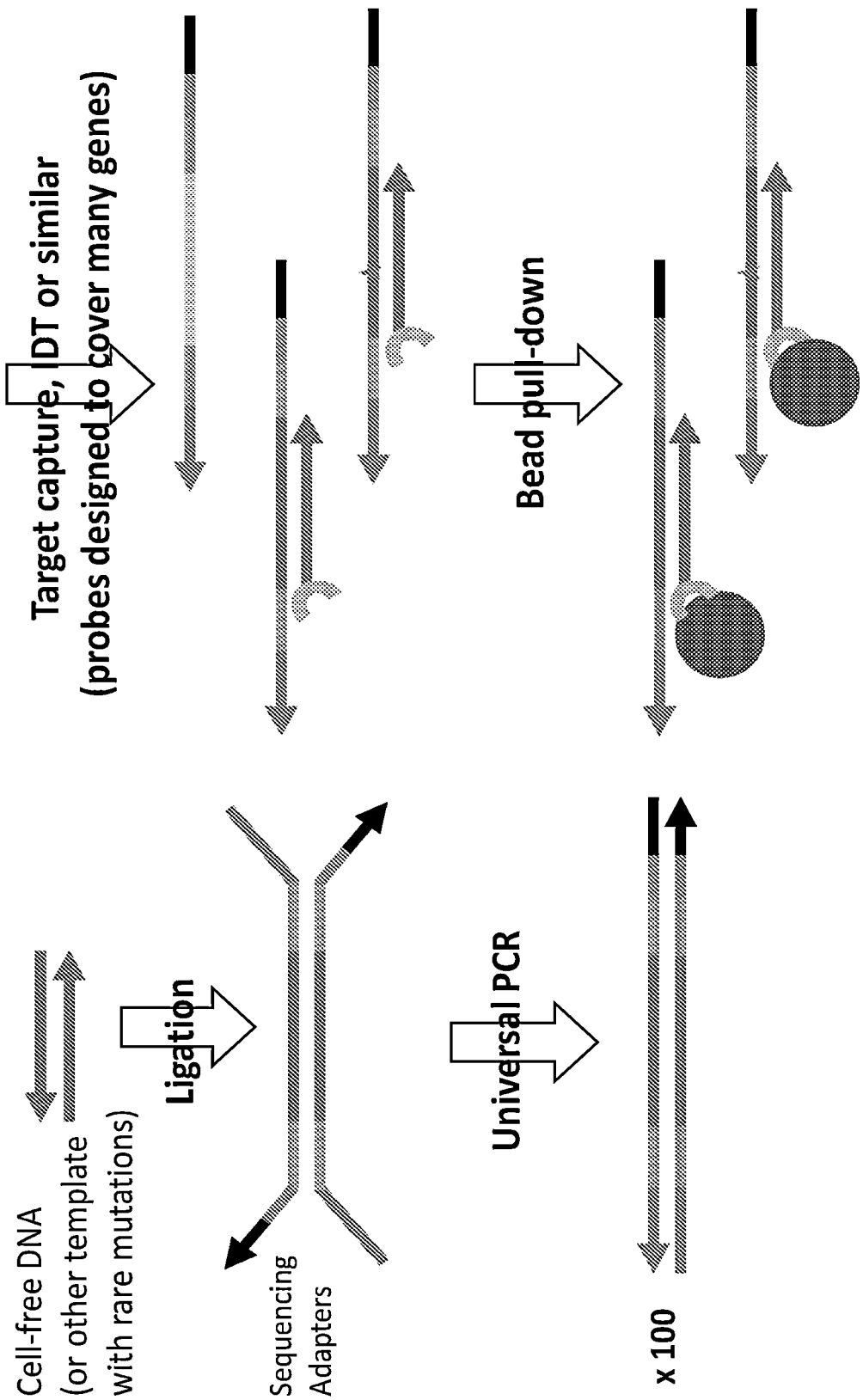
FIG. 19A shows exemplary steps for preparing a mixture of heteroduplexed and homoduplexed nucleic acid.
Figure 19B:
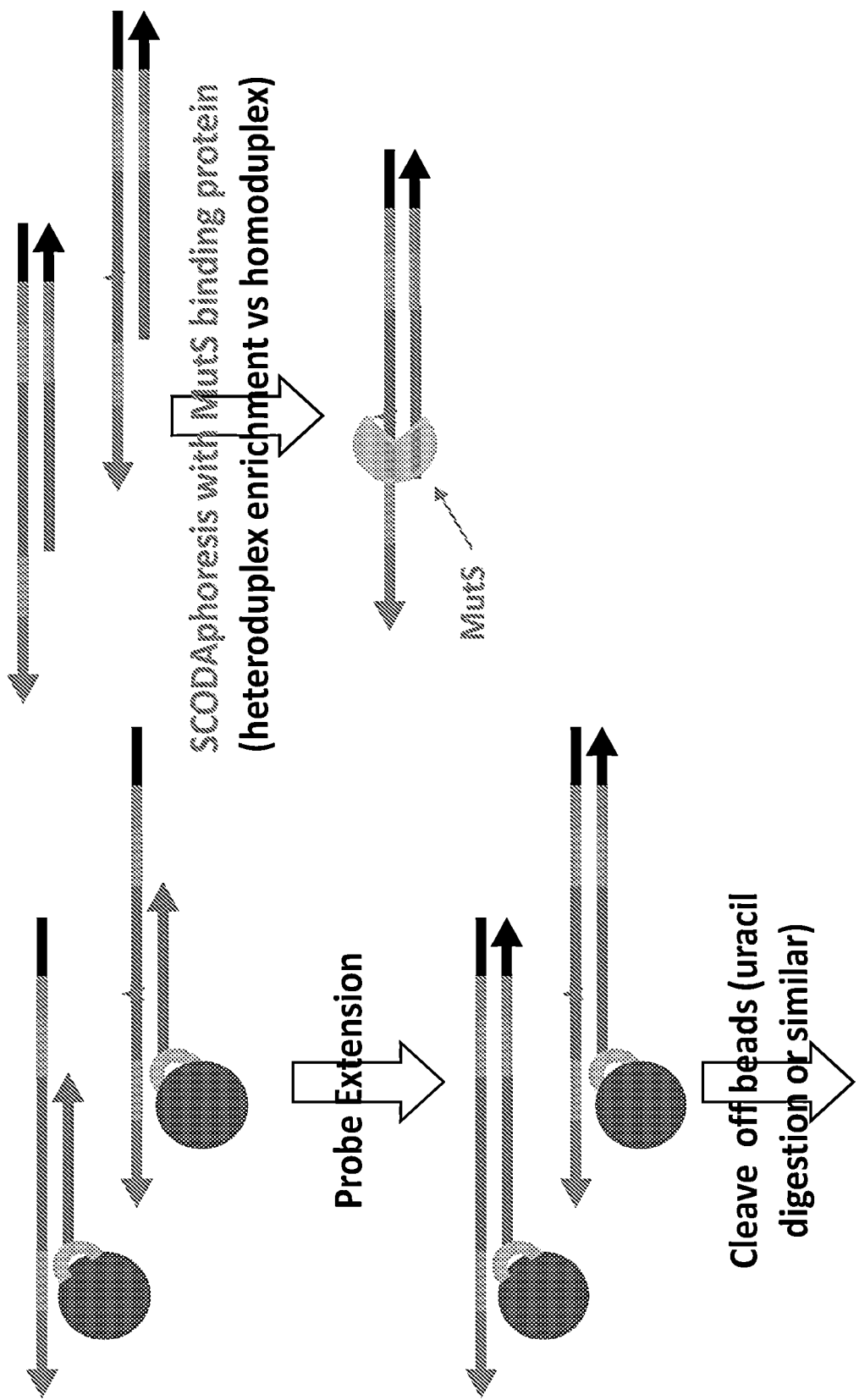
FIG. 19B shows binding MutS protein to heteroduplex nucleic acid.
Figure 19C:
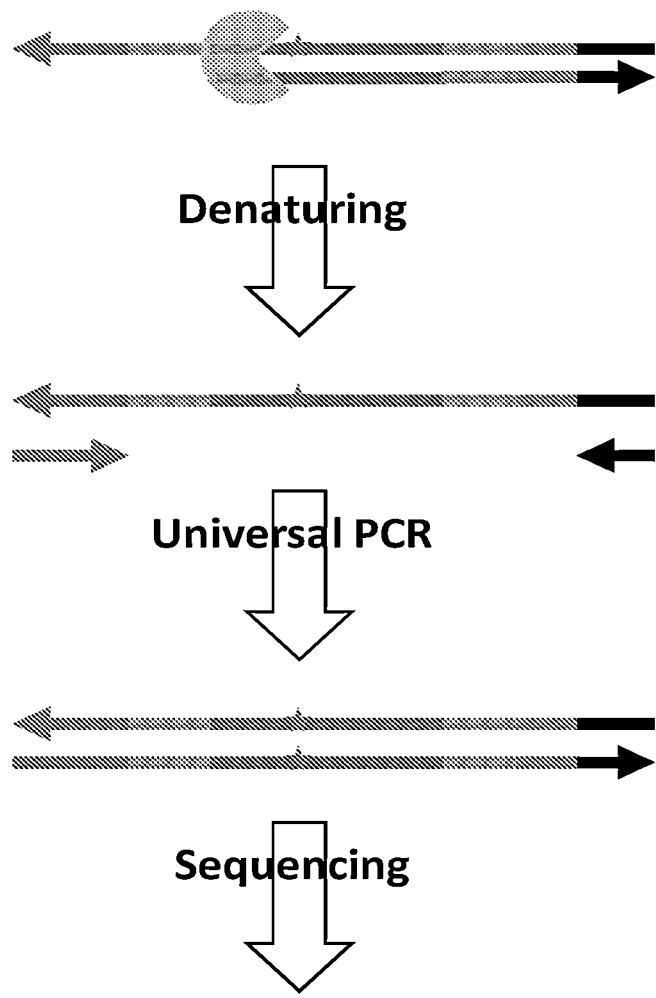
FIG. 19C shows recovery of isolated target nucleic acid and subsequent sequencing.

FIGS. 19A-19C provide specific details for separating nucleic acid having a mutation (target) from a larger body of wild-type (background) nucleic acids. As shown in FIG. 19A the process begins with, e.g., a cell-free DNA sample including a mutation. (The mutation is represented by a star, however the star is not shown in the first step). After the DNA is recovered and cleaned, adapter sequences, optionally containing molecular barcodes, are ligated to the recovered DNA. The nucleic acid, along with the adapters, is then amplified with universal PCR. Once a population of useful nucleic acids has been produced, the population can be selectively limited to a target region with biotinylated hybrid capture probes linked to streptavidin beads, or similar nucleic acid target capture technique Because the capture probes are designed to match wild-type DNA, any non wild-type mutation will create a heteroduplex with the capture probe. As show in FIG. 19B, the probe is then optionally extended to the 5' end of the target template, and any remaining beads are cleaved off the target DNA.complex prior to separation. All of the nucleic acids (heteroduplex and homoduplex) are then loaded onto an OnTarget™ chip (Boreal Genomics, Vancouver, Canada), with the heteroduplex-binding protein included in the separation medium, to perform SCODAphoresis. The mixture of homo- and heteroduplexed nucleic acid is then allowed to interact with the heteroduplex binding protein during cycled periods of driving fields and temperature. Heteroduplex molecules are preferentially separated, and collected into a central liquid medium. Finally, as shown in FIG. 19C, the heteroduplex-binding protein-nucleic acid complex is denatured to remove any residual heteroduplex-binding protein, leaving the mutant nucleic acid. The separated (mutant) nucleic acid can then be amplified and sequenced using standard techniques, e.g., Illumina sequencing.

Figure 20:
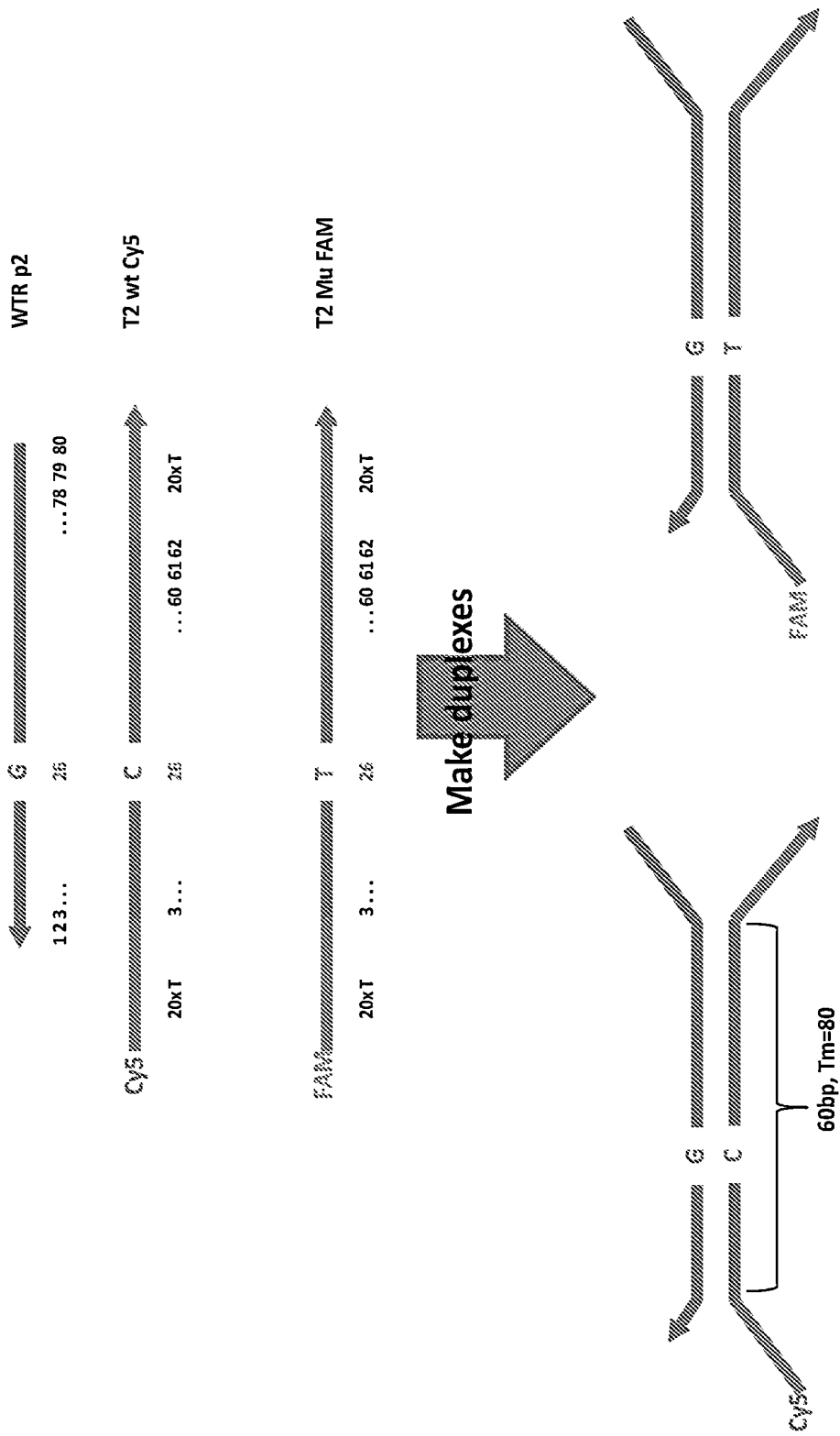
FIG. 20 depicts fluorescently-labeled nucleic acids used in the Examples.

Example 2—Separation of Fluorescently Labeled Nucleic Acids Using Heteroduplex Binding Proteins The workflow described above was used to separate a mixture of fluorescently-labeled nucleic acids. As shown in FIG. 20, a wild-type nucleic acid was prepared with a Cy5 label and a mutant nucleic acid (having a "T" instead of a "C") was labeled with FAM. Both nucleic acids were allowed to anneal with the complimentary wild-type strand, thus forming a Cy5-labeled homoduplex and a FAM-labeled heteroduplex. The nucleic acids were separately amplified to assure that an equivalent quantity of homo- and heteroduplexed nucleic acids were produced. Approximately 100 ng of the heteroduplex and 100 ng of the homoduplex were then combined with approximately 500 nM of MutS protein from *Thermus* thermophiles to create a 25 μL mixture that was loaded onto a 3-arm OnTarget™ cassette, as described above. The separation medium consisted of 4% polyacrylamide with a 29:1 crosslink ratio and the medium included about 2.5 μM *Thermus thermophiles* MutS protein mixed into the gel. A buffer including 1× Tris-Borate, 20 mM $MgCl_2$ was used throughout the separation.

Figure 21:
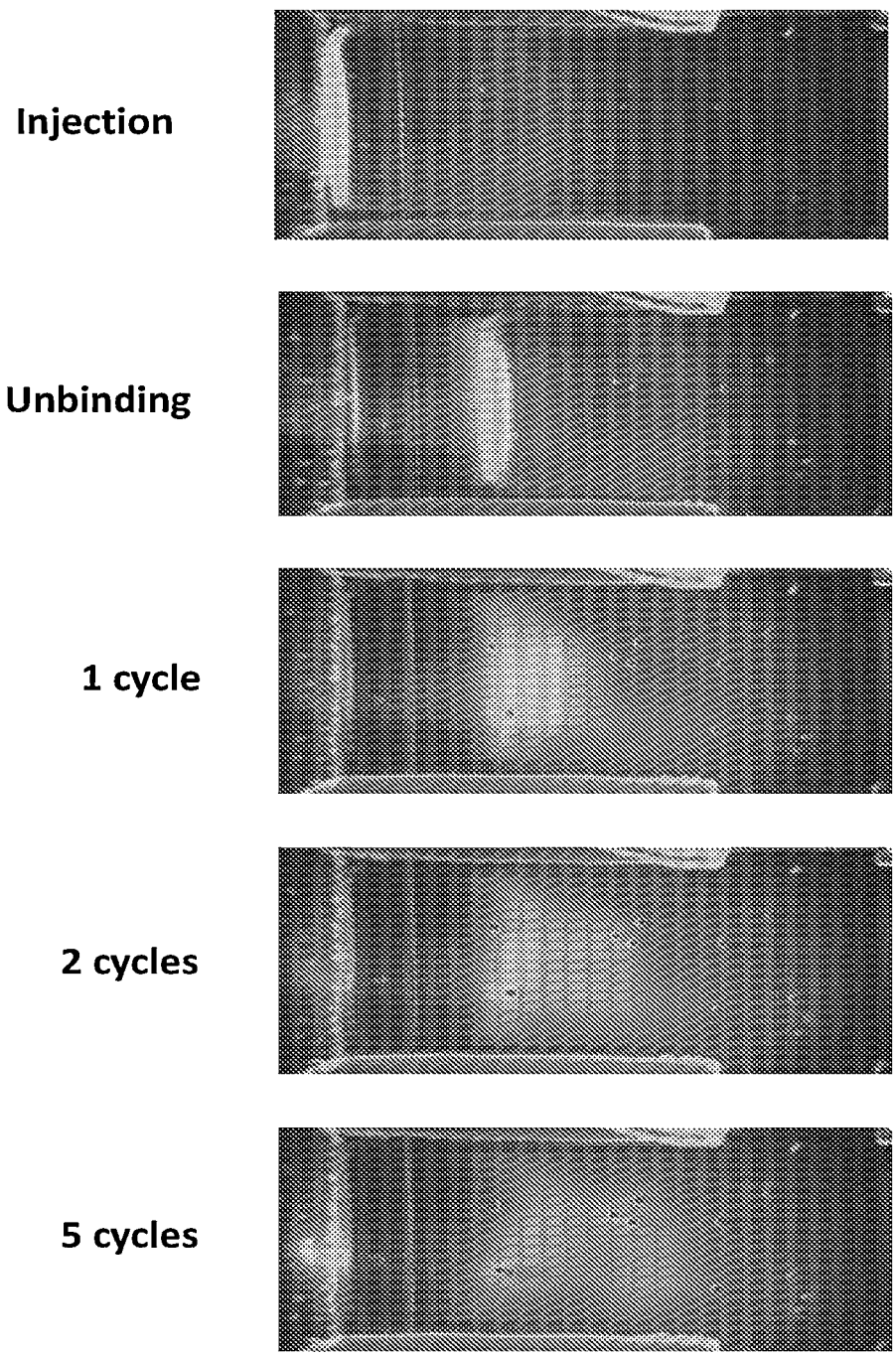
FIG. 21 shows fluorescence images of labeled hetero- and homoduplexed nucleic acids during various stages of separation.

FIG. 21 shows fluorescent images of the loading of the labeled nucleic acids, and separation between the mutant and wild-type strands. After only five separation cycles (looped boxes in FIG. 18), the mutant heteroduplex nucleic acid (green, left) is separated from the wild type homoduplex nucleic acid (red, right). With a greater number of cycles, most of the wild-type nucleic acid would be removed from the medium.

Figure 22A:
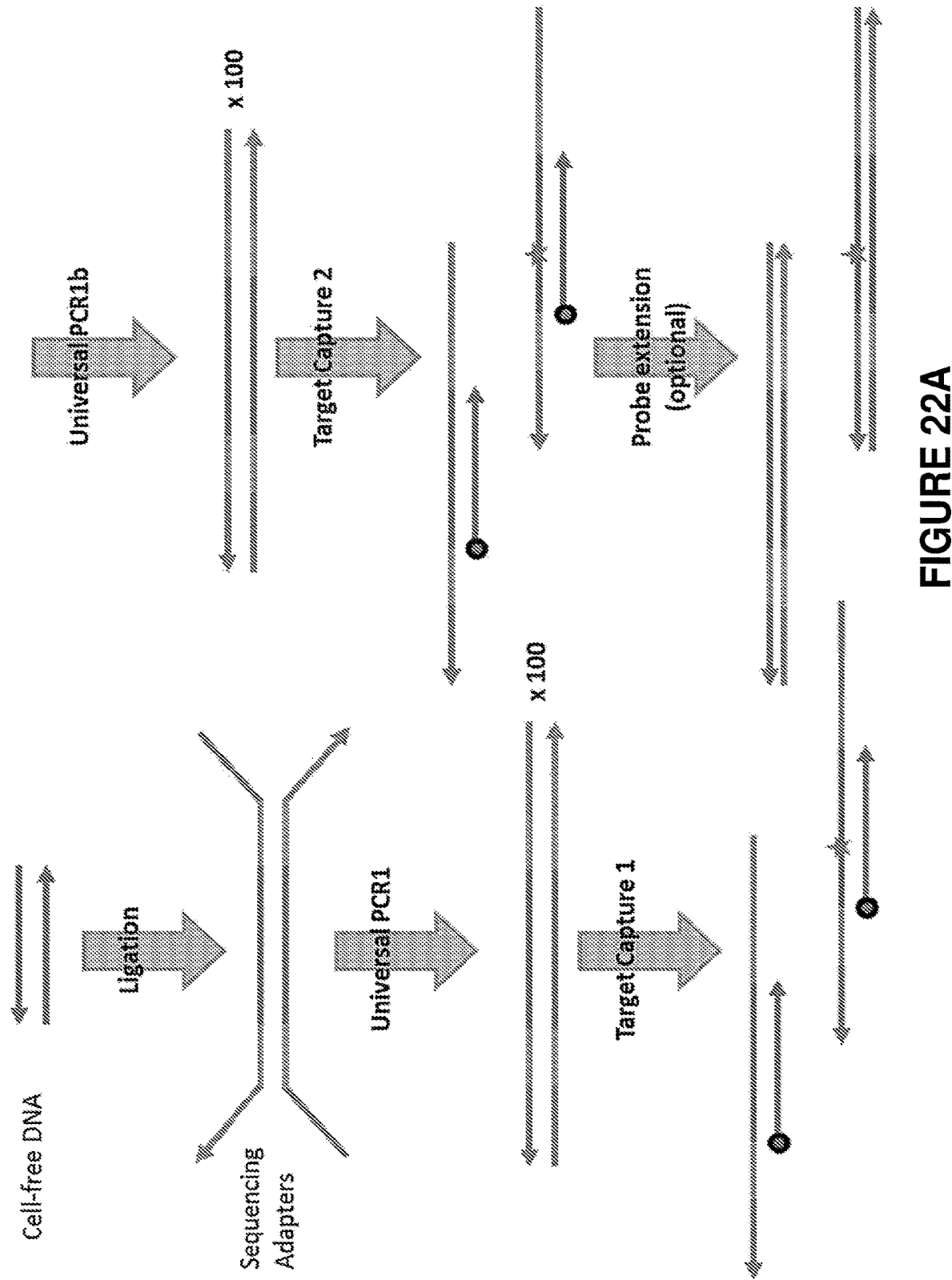
FIG. 22A shows exemplary steps for preparing a mixture of heteroduplexed and homoduplexed nucleic acid with an second PCR and target capture step.
Figure 22B:
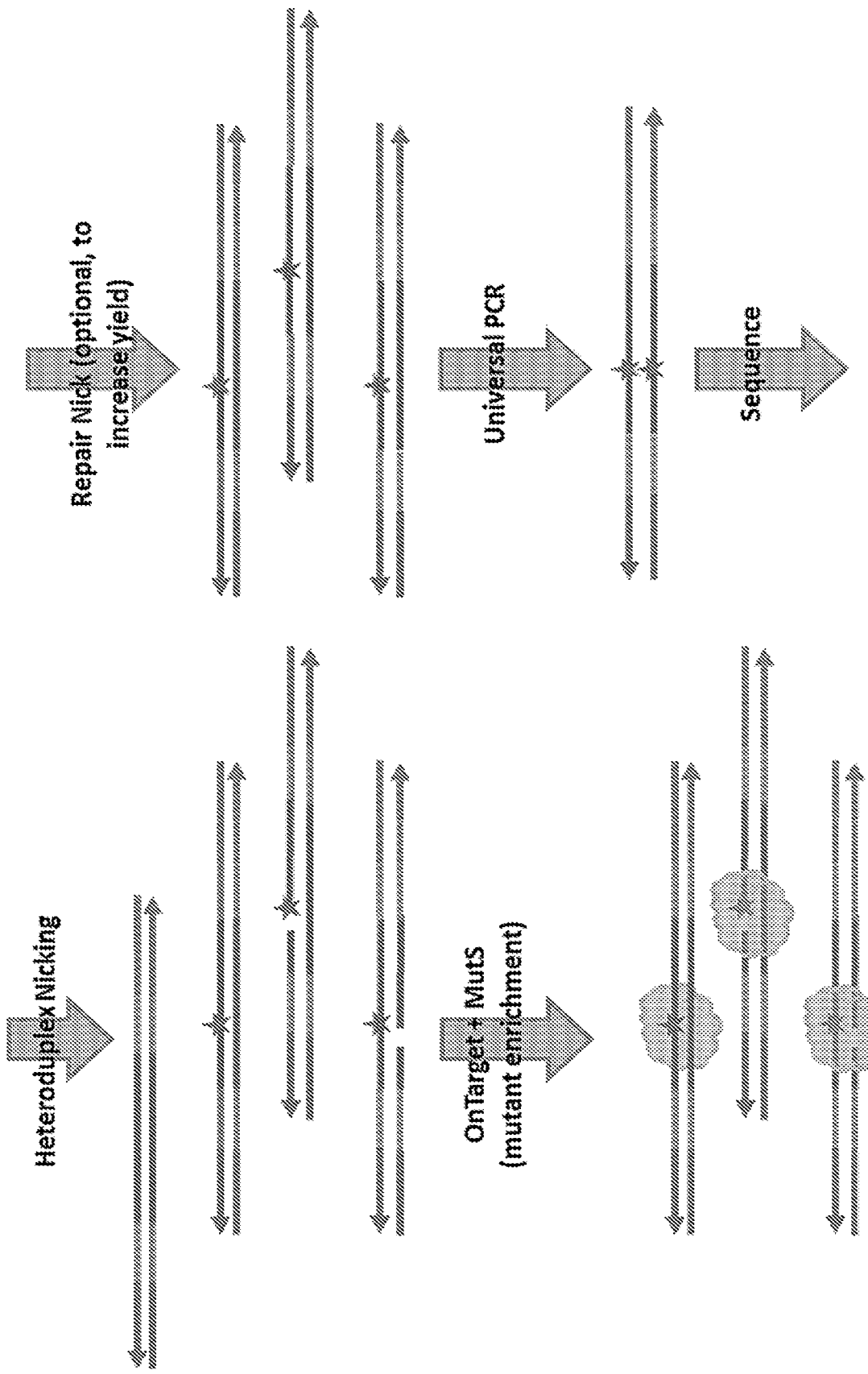
FIG. 22B shows nicking of heteroduplex nucleic acids before binding of a MutS protein to the heteroduplex nucleic acids.

Example 3—Work Flow for Separation of Rare Nucleic Acid Mutation from a Sample Using with Nicking FIGS. 22A and 22B provide specific details for separating nucleic acid having a mutation (target) from a larger body of wild-type (background) nucleic acids. As shown in FIG. 22A the process begins with, e.g., a cell-free DNA sample including a mutation. (The mutation is represented by a star, however the star is not shown in the first step). After the DNA is recovered and cleaned, adapter sequences, optionally containing molecular barcodes, are ligated to the recovered DNA. The nucleic acid, along with the adapters, is then amplified with universal PCR. Once a population of useful nucleic acids has been produced, the population can be selectively limited to a target region with biotinylated hybrid capture probes linked to streptavidin beads, or similar nucleic acid target capture technique. Because the capture probes are designed to match wild-type DNA, any non wild-type mutation will create a heteroduplex with the capture probe. The universal primer amplification and nucleic acid target capture may be repeated on the sample one or more times as shown in FIG. 22A. The probe is then optionally extended to the target template, and any remaining beads are cleaved off the target DNA.complex prior to separation. The nucleic acids may then be subjected to nicking at the mismatch site using any of the methods discussed above including an optional ligation step to repair nicks in homoduplex strands. All of the nucleic acids (heteroduplex and homoduplex) are then loaded onto an OnTarget™ chip (Boreal Genomics, Vancouver, Canada), with the heteroduplex-binding protein (e.g., MutS) included in the separation medium, to perform SCODAphoresis. The mixture of homo- and heteroduplexed nucleic acid is then allowed to interact with the heteroduplex binding protein during cycled periods of driving fields and temperature. Heteroduplex molecules are preferentially separated, and collected into a central liquid medium. The separated (mutant) nucleic acid can then be amplified and sequenced using standard techniques, e.g., Illumina sequencing.

Example 4—Separation of p53 Nucleic Acids Using Heteroduplex Binding Proteins

Figure 23:
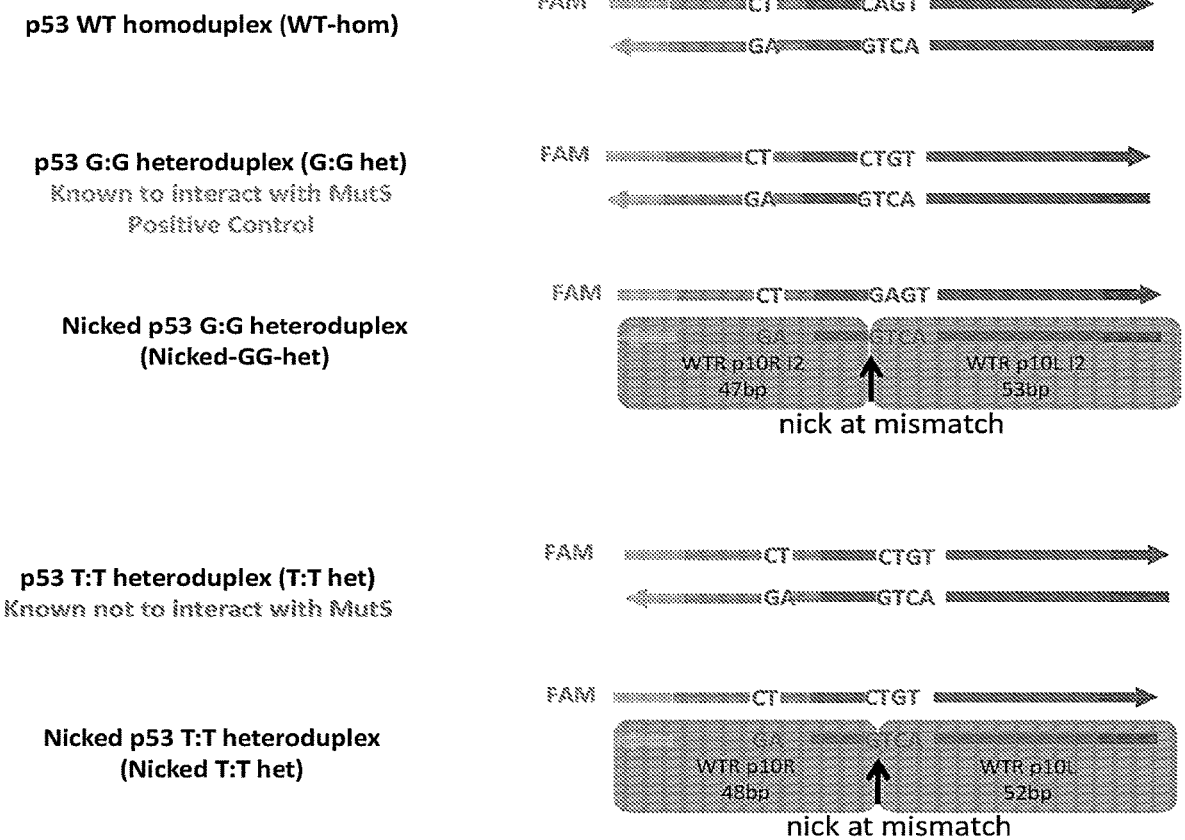
FIG. 23 shows heteroduplex templates, including nicked heteroduplex templates used in the examples.
Figure 24:
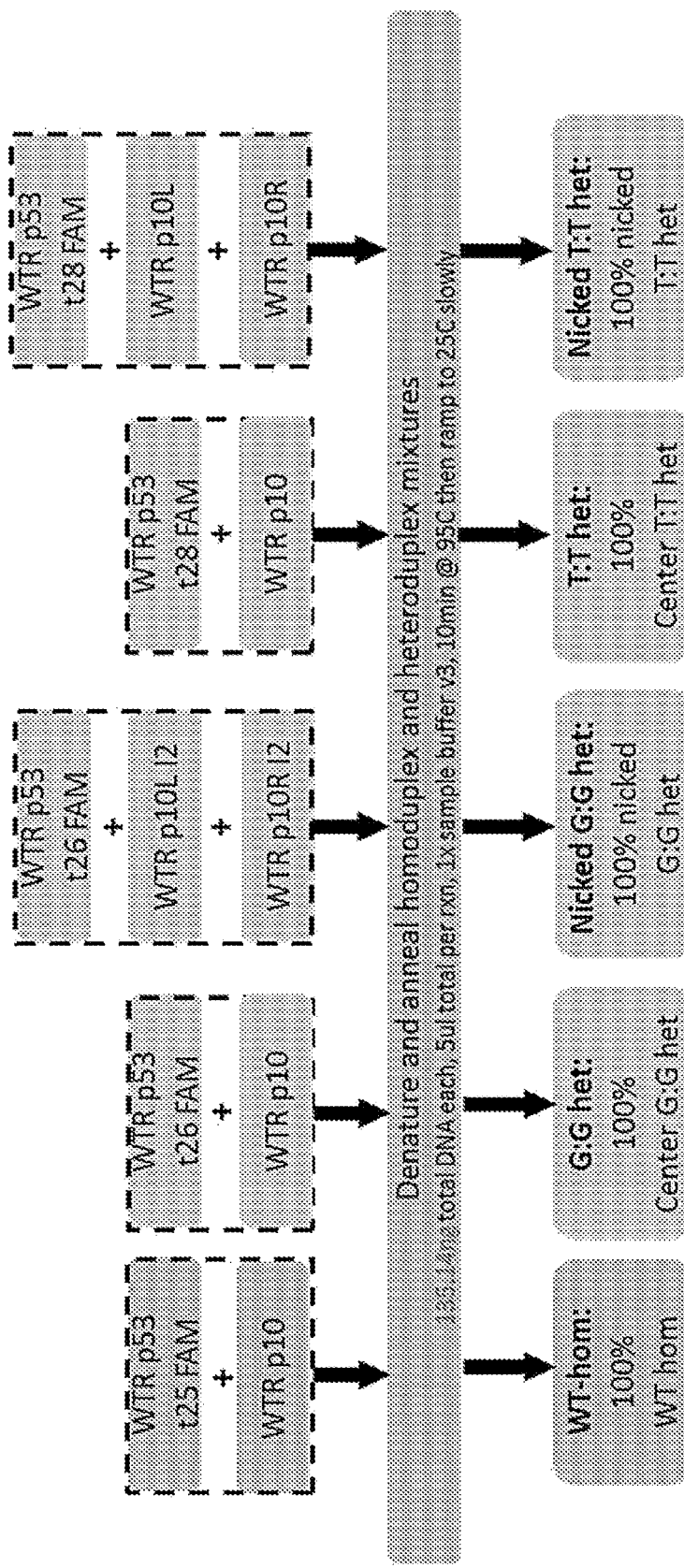
FIG. 24 shows a process used to create heteroduplex templates, including nicked heteroduplex templates used in the examples.
Figure 25:
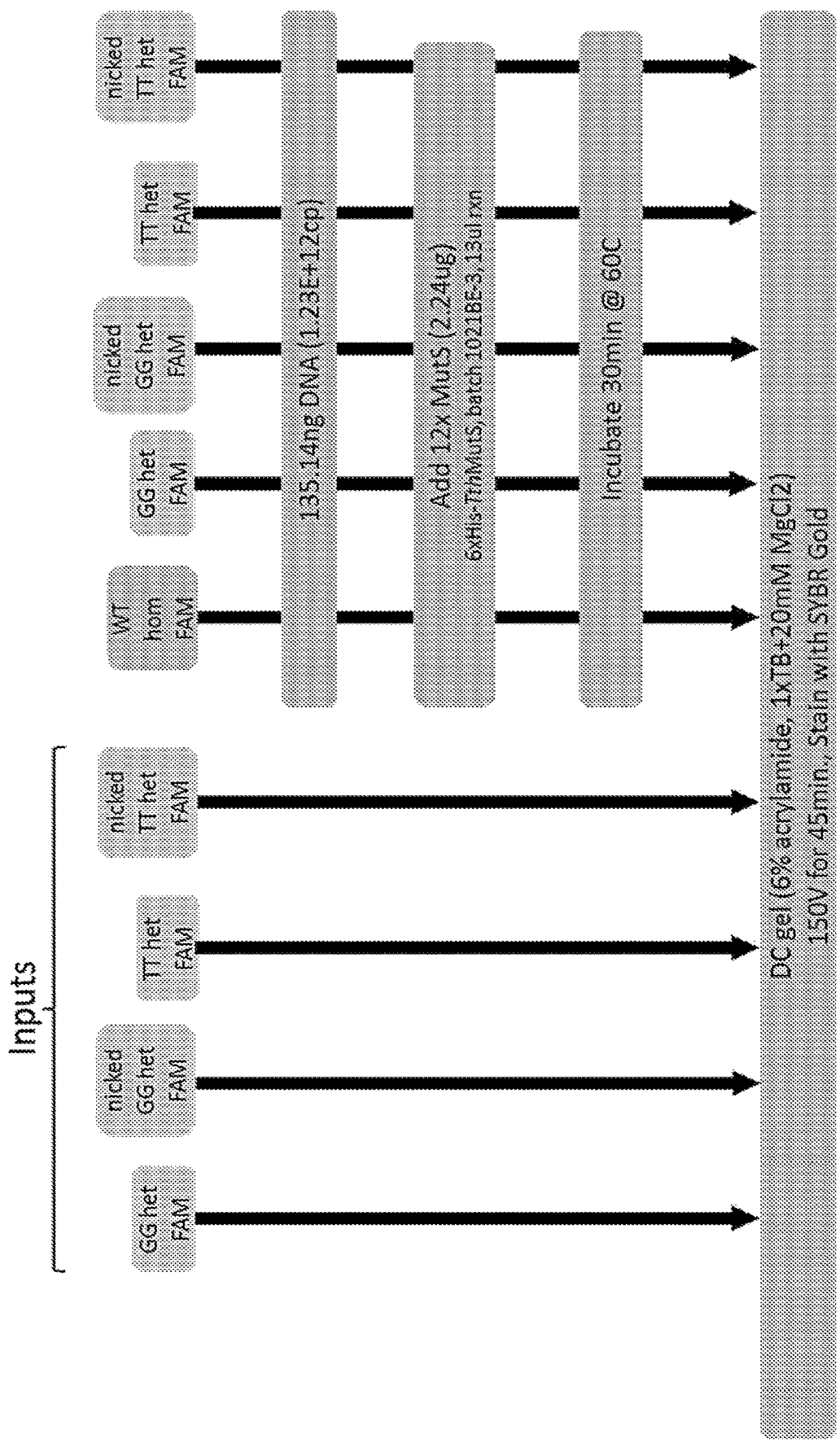
FIG. 25 shows a gel electrophoresis set up used in the examples with heteroduplex templates, including nicked heteroduplex templates.
Figure 26:
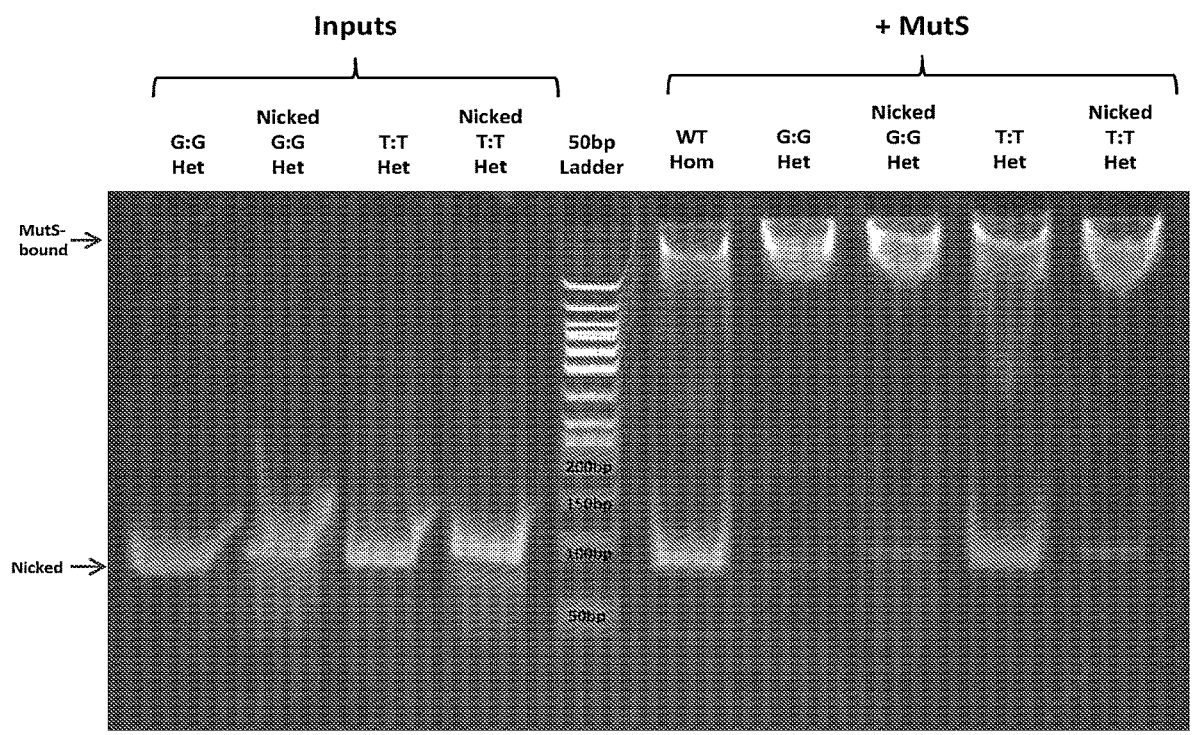
FIG. 26 shows the results of a gel electrophoresis run using heteroduplex templates, including nicked heteroduplex templates described in the examples.

To investigate effects of nicking on heteroduplex recognition by heteroduplex-binding proteins, multiple homoduplex and nicked and un-nicked heteroduplex 100 bp p53 duplexes as shown in FIG. 23 were prepared as shown in FIG. 24. The 1× sample buffer used in duplex preparation consisted of 50 mM Tris-HCL, pH8; 100 mM KCl; 0.1 mM EDTA; 20 mM $MgCl_2$; 1 mM DTT; and 10% v/v glycerol. The samples were then run in a gel with and without MutS binding as shown in FIG. 25 with 91,400 g/mol used as MutS molecular weight for the calculations. The results are shown in FIG. 26 run in 6% 1×TB buffer with 20 mM $MgCl_2$ at 150V for 45 minutes and stained with SYBR Gold. As shown in FIG. 26, the nicked T:T heteroduplex template shows significantly more binding affinity for MutS than the un-nicked TT:heteroduplex template.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for separating target heteroduplex nucleic acid from background nucleic acid, comprising;
   nicking the target heteroduplex nucleic acid;
   loading a mixture of nicked target heteroduplex nucleic acid and background homoduplex nucleic acid on a separation medium, wherein the target heteroduplex nucleic acid and the background homoduplex nucleic acid differ by at least one base;
   contacting the mixture of target heteroduplex nucleic acid and background homoduplex nucleic acid with a heteroduplex-binding protein to create a heteroduplex-binding protein-nucleic acid mixture;
   applying a time-varying driving field to the separation medium; and
   applying a time-varying mobility varying field to the separation medium,
   thereby causing the target heteroduplex nucleic acid to be separated from the background homoduplex nucleic acid.

2. The method of claim 1, wherein the separation medium comprises the heteroduplex binding protein.

3. The method of claim 1, wherein the heteroduplex-binding protein comprises a mismatch recognition domain.

4. The method of claim 1, wherein the heteroduplex-binding protein is MutS or a modified MutS protein.

5. The method of claim 1, wherein the amino acid sequence of the heteroduplex-binding protein is at least 85% identical to SEQ ID NO.1, SEQ ID NO. 2, or SEQ ID NO. 3.

6. The method of claim 1, further comprising denaturing the heteroduplex-binding protein.

7. The method of claim 1, wherein the time-varying driving field comprises two or three non-collinear electric fields.

8. The method of claim 1, further comprising sequencing the target heteroduplex nucleic acid.

9. The method of claim 1, wherein the background nucleic acid comprises wild-type nucleic acid and the target nucleic acid comprises a mutation.

10. The method of claim 1, further comprising:
    obtaining a sample comprising nucleic acid;
    denaturing the nucleic acid to produce single-stranded nucleic acid; and
    reannealing the single-stranded nucleic acid with reference to nucleic acids to create the mixture of target heteroduplex nucleic acid and background homoduplex nucleic acid.

11. The method of claim 10, further comprising amplifying the single-stranded nucleic acid.

12. The method of claim 11, further comprising adding an adapter sequence or a barcode sequence to the target heteroduplex nucleic acid and background homoduplex nucleic acid.

13. The method of claim 1, wherein the target heteroduplex nucleic acid to background homoduplex nucleic acid ratio is from 1:1 to 1:1,000,000.

14. The method of claim 1, wherein the target heteroduplex nucleic acid and homoduplex background nucleic acid are recovered from a biological sample, wherein the sample is selected from whole blood, serum, plasma, sputum, tissue, sweat, tears, urine, or aspirate.

15. The method of claim 14, further comprising identifying a ratio of target heteroduplex nucleic acid to background homoduplex nucleic acid in the sample.

16. The method of claim 1, further comprising nicking and then ligating the homoduplex nucleic acid.

* * * * *